United States Patent
Bao et al.

(10) Patent No.: US 7,446,188 B2
(45) Date of Patent: Nov. 4, 2008

(54) PLANT CYCLOPROPANE FATTY ACID SYNTHASE GENES, PROTEINS, AND USES THEREOF

(75) Inventors: Xiaoming Bao, Johnston, IA (US); John B. Ohlrogge, Okemos, MI (US); Michael R. Pollard, Okemos, MI (US)

(73) Assignee: Michigan State University

( * ) Notice: Subject to any disclaimer, the term of this patent is extended or adjusted under 35 U.S.C. 154(b) by 301 days.

(21) Appl. No.: 10/499,246

(22) PCT Filed: Dec. 20, 2002

(86) PCT No.: PCT/US02/41250

§ 371 (c)(1),
(2), (4) Date: Mar. 24, 2005

(87) PCT Pub. No.: WO03/060079

PCT Pub. Date: Jul. 24, 2003

(65) Prior Publication Data

US 2006/0053512 A1     Mar. 9, 2006

Related U.S. Application Data

(60) Provisional application No. 60/345,152, filed on Dec. 21, 2001, provisional application No. 60/393,937, filed on Jul. 3, 2002.

(51) Int. Cl.
*C07H 21/04* (2006.01)
*A61K 36/00* (2006.01)

(52) U.S. Cl. .................. 536/23.2; 536/23.6; 530/370

(58) Field of Classification Search .................. None
See application file for complete search history.

(56) References Cited

U.S. PATENT DOCUMENTS 5,936,139 A * 8/1999 Schmid ................ 800/281

* cited by examiner

*Primary Examiner*—Elizabeth F McElwain
(74) *Attorney, Agent, or Firm*—Medlen & Carroll, LLP

(57) ABSTRACT

The present invention provides cyclopropane fatty acid synthase genes and proteins, and methods of their use. The present invention encompasses both native and recombinant wild-type forms of the synthase, as well as mutants and variant forms, some of which possess altered characteristics relative to the wild-type synthase. The present invention also provides methods of using cyclopropane fatty acid synthase genes and proteins, including in their expression in transgenic organisms and in the production of cyclopropane fatty acids in plant oils, and in particular seed oils.

14 Claims, 21 Drawing Sheets

Nuclear Acid Sequence of Sterculia Fatty Acid Cyclopropane Synthase

```
ATGGGAGTGGCTGTGATCGGTGGTGGGATCCAAGGGCTGGTTTCGGCCTACGTTCTTGC
CAAAGCCGGCGTCAACGTCGTTGTTTACGAGAAAGAGGAGCAAGTAGGTGGCCATGCCA
AGACTGTTAGCTTTGACGCCGTCGATTTGGACCTTGGCCTCTTGTTTCTCAACCCTGCA
AGGTATCCAACAATGTTGGAGCTGTTTGATAGCCTTGAAGTTCATGTGGAGGCAACTGA
TGTTTCATTCTCTGTAAGCCATGACAAAGGCAATGGCTATGAATGGTGCAGCCAGTACG
GTTTTTCGAACTTTTTAGCACACAAGAAGAAATGTTGAATCCTTACAATTGGCAAGAC
CTCAGAGAAACTATCAAGTTCGGAAATGATGTCAATAGTTATCTTGAATCGCTTGAGAA
GAATCCTGACATTGATCGTAATGAAACCTTGGGGCATTTTGTAGGGTCAAAGGGTTACT
CTGAAAATTTTCTGAACACTTACCTGGCTCCAATATGTGGTTCAATGTGGTCCTGCTCC
AAGGAAGAAGTTATGAGCTTTTCAGCCTACTCCATTCTTTCGTTTTGTCGCACTTATCA
TCTGTACCAGCTATTTGGGAATCCACAGTGGCTGACTATTAAAAGGCACTCATATTTAG
TTAAAAAGGTCAGAGATATTCTGGAAAGCAGAGGTTGTCAGTTTAAACTTGGTTGTGAA
GTGCTTTCTGTTTTGCCTGCTGATGATGGTAGCTCCATAGTCTTTGGAGATGGTTTCCA
AGAAACGTACAATGGATGCATAATGGCTGTTAATGCTCCCACAGCCCTAAAAATATTAG
GAAACCAAGCAACATTTGAAGAAATGAGAGTTCTGGGTGCATTCCAATATGCTTCCAGT
GATATTTACCTTCACCGTGACAGCAATTTAATGCCCACAAACAGATCAGGTTGGAGTGC
ACTGAATTTTCTCAGAAGTAGAGAAAATAAAGCAAGCTTAACATACTGGCTCAATGTGC
TACAGAATGTTGGGAAAACAAGTCAGCCCTTTTTTGTGACTCTCAATCCAGACCGTATC
CCAGACAAAATCTTGCTTAAGTGGTCGACTGGACGTCCAATTCCCTCTGTTGCTGCATC
AAAAGCTTCACTTGAGCTAGATCAGATTCAGGGGAAGAGAGGAATCTGGTTCTGTGGCT
ATGACTTCCATGAGGATGAATTAAAGGCTGGTATGGATGCTGCACATCGTATCTTGGGA
AAGCATTTTTCTGTTCTGCACAGTCCAAGGCAAATGTCACCCTCTTTCATGGAAACAAC
GGCACGTCTTCTTGTTACTAAATTCTTTCACCAATATATACAAGTGGGCTGCGTAATAA
TCATAGAGGAAGGTGGCAGAGTTTACACTTTCAAAGGAAGCATGGAAAATTGTTCTCTT
AAAACAGCTCTGAAAGTGCATAATCCTCAGTTTTACTGGAGGATTATGAAAGAAGCTGA
TATAGGCCTTGCTCATGCATATATCCAAGGAGATTTTTCTTTTGTTGACAAGGATGATG
GTCTTCTTAATCTTTTCCGGATACTTATTGCCAATAAAGAGTTGAACTCTGCCTCAGGA
CAGAACAAAAGAAGGACTTGGCTGTCACCTGCACTGTTCACAGCTGGTATATCATCTGC
AAAGTATTTCTTGAAGCATTACATGAGGCAAAATACTGTTACACAGGCTCGCAGGAACA
TTTCTCGTCATTATGACCTGAGTAATGAACTTTTCACTCTATACTTAGGTGAAATGATG
CAATACTCTTCTGGAATTTTTAAGACGGGAGAAGAACATTTGGACGTTGCACAGCGCAG
AAAAATCAGTTCCTTAATTGATAAATCAAGAATAGAGAAGTGGCATGAAGTTCTTGACA
TTGGATGTGGTTGGGGAAGCTTAGCTATGGAAGTTGTCAAAAGAACAGGATGTAAATAC
ACTGGCATCACACTTTCAGAGCAGCAACTGAAATATGCAGAAGAAAAGTGAAGGAAGC
TGGACTTCAGGGAAACATCAAATTTCTTCTCTGTGACTATCGCCAGTTACCCAAGACAT
TCAAATATGACAGAATCATATCTGTTGAGATGGTTGAACATGTTGGTGAAGAATATATT
GAGGAGTTTTTCAGATGCTGTGACTCATTATTGGCAGAGAATGGGCTTTTCGTTCTTCA
GTTCATATCAATTCCAGAGATACTTTCCAAAGAAATCCAGCAAACAGCTGGTTTTCTAA
AGGAATATATCTTCCCTGGTGGAACCCTGCTTTCTCTGGATAGGACTTTGTCAGCCATG
GCTGCTGCATCAAGATTTAGTGTGGAGCATGTGGAAATATAGGAATTAGTTATTATCA
CACACTGAGATGGTGGAGGAAAAATTTCTTGGCAAATGAAAGCAAGTTCTGGCTTTGG
GGTTCGATGAGAAGTTCATGCGGACATGGGAGTATTATTTTGATTACTGCGCAGCTGGT
```

FIG 4

```
TTTAAGACAGGGACACTTATAGATTACCAGGTTGTATTCTCACGGGCTGGCAATTTCGC
TGCACTTGGCGATCCATACATAGGTTTCCCTTCAGCATATTCCTACTCGGATAAT
```

Amino Acid Sequence of Sterculia Cyclopropane Fatty Acid Synthase (864aa)

```
MGVAVIGGGI QGLVSAYVLA KAGVNVVVYE KEEQVGGHAK TVSFDAVDLD
LGLLFLNPAR YPTMLELFDS LEVDVEATDV SFSVSHDKGN GYEWCSQYGF
SNFLAHKKKM LNPYNWQDLR ETIKFGNDVN SYLESLEKNP DIDRNETLGH
FVGSKGYSEN FLNTYLAPIC GSMWSCSKEE VMSFSAYSIL SFCRTYHLYQ
LFGNPQWLTI KRHSYLVKKV RDILESRGCQ FKLGCEVLSV LPADDGSSIV
FGDGFQETYN GCIMAVNAPT ALKILGNQAT FEEMRVLGAF QYASSDIYLH
RDSNLMPTNR SGWSALNFLR SRENKASLTY WLNVLQNVGK TSQPFFVTLN
PDRIPDKILL KWSTGRPIPS VAASKASLEL DQIQGKRGIW FCGYDFHEDE
LKAGMDAAHR ILGKHFSVLL SPRQMSPSFM ETTARLLVTK FFHQYIQVGC
VIIIEEGGRV YTFKGSMENC SLKTALKVHN PQFYWRIMKE ADIGLADAYI
QGDFSFVDKD DGLLNLFRIL IANKELNSAS GQNKRRTWLS PALFTAGISS
AKYFLKHYMR QNTVTQARRN ISRHYDLSNE LFTLYLGEMM QYSSGIFKTG
EEHLDVAQRR KISSLIDKSR IEKWHEVLDI GCGWGSLAME VVKRTGCKYT
GITLSEQQLK YAEEKVKEAG LQGNIKFLLC DYRQLPKTFK YDRIISVEMV
DMVGEEYIEE FFRCCDSLLA ENGLFVLQFI SIPEILSKEI QQTAGFLKEY
IFPGGTLLSL DRTLSAMAAA SRFSVEHVEN IGISYYHTLR WWRKNFLANE
SKVLALGFDE KFMRTWEYYF DYCAAGFKTG TLIDYQVVFS RAGNFAALGD
PYIGFPSAYS YSDN
```

Amino Acid Alignment between Sterculia and Bacterial Cyclopropane Fatty Acid Synthase

```
                    *        20         *        40         *        60         *        80
Sterculia   : MGVAVIGGGIQGLVSAYVLAKAGVNVVVYEKEEGVGGHAKTVSFDAVDLDLGLFFNPARYPTMLELFDSLEVDVEATDVS  : 81
gi|cfa.Eco  : --------------------------------------------------------------------------------  : -
                    *       100         *       120         *       140         *       160
Sterculia   : FSVSFDKGNGYEWCSQYGFSNFLAHKKKMLNPYNWQDLREFIKEGSDVNSYLESLFKNPDIDRNFTLGHFVGSKGYSENEL : 162
gi|cfa.Eco  : --------------------------------------------------------------------------------  : -
                    *       180         *       200         *       220         *       240
Sterculia   : NFYLAFICGSMFWSCSKEEVMSFSAYSILSFCRTYHLYQLFGNFQWLTKRHSYLVKKVRDFLESRGCQFKLGCFVLSVLPA : 243
gi|cfa.Eco  : --------------------------------------------------------------------------------  : -
                    *       260         *       280         *       300         *       320
Sterculia   : DDGSSIVFGDGFQETYNGCIVAVNAPIALKILGNQATFEEMRVLGAFQYASSDIYLHRDSNLMPTNRSGWSALNFLRSREN : 324
gi|cfa.Eco  : --------------------------------------------------------------------------------  : -
                    *       340         *       360         *       380         *       400
Sterculia   : KASLTYVLNVLQNVGKTSQFFFVTLNPDRIPDKFLLKWSTGKFIPSVAASKASLELDQIQGKRGIWFCGYDFHEDELKAGM : 405
gi|cfa.Eco  : --------------------------------------------------------------------------------  : -
                    *       420         *       440         *       460         *       480
Sterculia   : DAAIIRIEGKIIFSVLFISPRQMSFSFMETTARELVFKFFHQYLQVGGVHIFEGGRVYLFKGSMFNGFFKTFLKFENFQFYFR : 486
gi|cfa.Eco  : ------------------------------------------MSSSCIEFVSVFDDNFY                       : 17
                    *       500         *       520         *       540         *       560
Sterculia   : FKFAFFSLFDAYFQFDFSIFVFKDDGFFFFLFFLFFANKFFNSAFGQ------RRTFFLPAFFIAGFSSAKYFLFHYFF    : 560
gi|cfa.Eco  : RFANELFSRFGIAFNFSAEFAFDRVKNPDFEKRVLQEGSFGLGESYMDGWWECFDRFDMFFSKVFRAGLENQLPFHFKDTFLR : 97
                    *       580         *       600         *       620         *       640
Sterculia   : ---------QNFFVTQFRRNFISRFFFFSFEFFFLYFGEMFFFFSGFFTGEEHFDVFFRRFSSFFLDFSRFEKWHFF      : 633
gi|cfa.Eco  : LAGARLFNLQSKKRFAWTVGKEHYDLGNDLFSRMFFDPFMQYSCAYWKDADN-FFSAQQAKFKMFCEKFLGFKPGMRVFDIGCG : 177
                    *       660         *       680         *       700         *       720
Sterculia   : FSFFMEFVKRTFGCKYFFFFFFEFFFFYFFFFFVKFAGLQGNFFKFFFFQFPKFFKFFFFFFFFVFFFFFYLELFFRFF   : 714
gi|cfa.Eco  : WGGLAHYMASSNYDVSVVGVTISAFQQKMAQERCFGLD---VTILFQDYRDFF-DQFDRIVSVGMFTHVGFPKNYDTYFAV  : 252
                    *       740         *       760         *       780         *       800
Sterculia   : CFFSFFAFNFFFFFQFFSFFFLFSKFFQQFFAGFFFKFFFFFTFFFFFDRTFSAMFAAASRFFSFFFHVFFFFISFYFFRWFFRKN : 795
gi|cfa.Eco  : VFDRNFFKPEGFFHLFFHTFGS-KFKF-TDFNFVDPFWINKYFFENGFFIPSVRQF-AQSSEPH-FVMEFWHFFGAFFYFTFFFFFYER : 327
                    *       820         *       840         *       860         *
Sterculia   : FFFFNESKFFLACFGFFDFFFFMFFFFFFYFFAGFFTCTFFDFFFFFFFFAGNFFAALGFDFYFFFPFSAVSYSFDFF     : 864
gi|cfa.Eco  : FLAFAWFDFFADNFYSFFREFKRFFFFFYYFLFNFXFAGAFFRFRDFFQLFWQVVFSRGVFFNGLRVFFR------------ : 382
```

FIG 11

Primer Location in the *Sterculia* Cyclopropane Fatty Acid Synthase

```
ATGGGAGTGGCTGTGATCGGTGGTGGGATCCAAGGGCTGGTTTCGGCCTACGTTCTTGCCAAAGCCGGCGTCAACGTCGTTGTTTACGAGAAAGAGGAG
 M  G  V  A  V  I  G  G  G  I  Q  G  L  V  S  A  Y  V  L  A  K  A  G  V  N  V  V  V  Y  E  K  E  E
CAAGTAGGTGGCCATGCCAAGACTGTTAGCTTTGACGCCGTCGATTTGGACCTTGGCCTCTTGTTTCTCAACCCTGCAAGGTATCCAACAATGTTGGAG
 Q  V  G  G  H  A  K  T  V  S  F  D  A  V  D  L  D  L  G  L  L  F  L  N  P  A  R  Y  P  T  M  L  E
CTGTTTGATAGCCTTGAAGTTGATGTGGAGGCAACTGATGTTTCATTCTCTGTAAGCCATGACAAAGGCAATGGCTATGAATGGTGCAGCCAGTACGGT
 L  F  D  S  L  E  V  D  V  E  A  T  D  V  S  F  S  V  S  H  D  K  G  N  G  Y  E  W  C  S  Q  Y  G
TTTTCGAACTTTTTAGCACACAAGAAGAAAATGTTGAATCCTTACAATTGGCAAGACCTCAGAGAAACTATCAAGTTCGGAAATGATGTCAATAGTTAT
 F  S  N  F  L  A  H  K  K  K  M  L  N  P  Y  N  W  Q  D  L  R  E  T  I  K  F  G  N  D  V  N  S  Y
CTTGAATCGCTTGAGAAGAATCCTGACATTGATCGTAATGAAACCTTGGGCATTTTGTAGGGTCAAAGGGTTACTCTGAAAATTTTCTGAACACTTAC
 L  E  S  L  E  K  N  P  D  I  D  R  N  E  T  L  G  H  F  V  G  S  K  G  Y  S  E  N  F  L  N  T  Y
CTGGCTCCAATATGTGGTTCAATGTGGTCCTGCTCCAAGGAAGAAGTTATGAGCTTTTCAGCCTACTCCATTCTTTCGTTTTGTCGCACTTATCATCTG
 L  A  P  I  C  G  S  M  W  S  C  S  K  E  E  V  M  S  F  S  A  Y  S  I  L  S  F  C  R  T  Y  H  L
TACCAGCTATTTGGGAATCCACAGTGGCTGACTATTAAAAGGCACTCATATTTAGTTAAAAAGGTCAGAGATATTCTGGAAAGCAGAGGTTGTCAGTTT
 Y  Q  L  F  G  N  P  Q  W  L  T  I  K  R  H  S  Y  L  V  K  K  V  R  D  I  L  E  S  R  G  C  Q  F
AAACTTGGTTGTGAAGTGCTTTCTGTTTTGCCTGCTGATGATGGTAGCTCCATAGTCTTTGGAGATGGTTTCCAAGAAACGTACAATGGATGCATAATG
 K  L  G  C  E  V  L  S  V  L  P  A  D  D  G  S  S  I  V  F  G  D  G  F  Q  E  T  Y  N  G  C  I  M
GCTGTTAATGCTCCCACAGCCCTAAAAATATTAGGAAACCAAGCAACATTTGAAGAAATGAGAGTTCTGGGTGCATTCCAATATGCTTCCAGTGATATT
 A  V  N  A  P  T  A  L  K  I  L  G  N  Q  A  T  F  E  E  M  R  V  L  G  A  F  Q  Y  A  S  S  D  I
TACCTTCACCGTGACAGCAATTTAATGCCCACAAACAGATCAGGTTGGAGTGCACTGAATTTTCTCAGAAGTAGAGAAAATAAAGCAAGCTTAACATAC
 Y  L  H  R  D  S  N  L  M  P  T  N  R  S  G  W  S  A  L  N  F  L  R  S  R  E  N  K  A  S  L  T  Y
TGGCTCAATGTGCTGCAGAATGTTGGGAAAACAAGTCAGCCCTTTTTTGTGACTCTCAATCCAGACCGTATCCCAGACAAAATCTTGCTTAAGTGGTCG
 W  L  N  V  L  Q  N  V  G  K  T  S  Q  P  F  F  V  T  L  N  P  D  R  I  P  D  K  I  L  L  K  W  S
ACTGGACGTCCAATTCCCTCTGTTGCTGCATCAAAAGCTTCACTTGAGCTAGATCAGATTCAGGGGAAGAGAGGAATCTGGTTCTGTGGCTATGACTTC
 T  G  R  P  I  P  S  V  A  A  S  K  A  S  L  E  L  D  Q  I  Q  G  K  R  G  I  W  F  C  G  Y  D  F
CATGAGGATGAATTAAAGGCTGGTATGGATGCTGCACATCGTATCTTGGGAAAGCATTTTTCTGTTCTGCACAGTCCAAGGCAAATGTCACCCTCTTTC
 H  E  D  E  L  K  A  G  M  D  A  A  H  R  I  L  G  K  H  F  S  V  L  H  S  P  R  Q  M  S  P  S  F
ATGGAAACAACGGCACGTCTTCTTGTTACTAAATTCTTTCACCAATATATACAAGTGGGCTGCGTAATAATCATAGAGGAAGGTGGCAGAGTTTACACT
 M  E  T  T  A  R  L  L  V  T  K  F  F  H  Q  Y  I  Q  V  G  C  V  I  I  I  E  E  G  G  R  V  Y  T
                            EcoRI
      J0873    CCGGAATTCTGTTCTCTTAAAACAGCTCTGAAAGTGC
TTCAAAGGAAGCATGGAAAATTGTTCTCTTAAAACAGCTCTGAAAGTGCATAATCCTCAGTTTTACTGGAGGATTATGAAAGAAGCTGATATAGGCCTT
 F  K  G  S  M  E  N  C  S  L  K  T  A  L  K  V  H  N  P  Q  F  Y  W  R  I  M  K  E  A  D  I  G  L
GCTGATGCATATATCCAAGGAGATTTTTCTTTTGTTGACAAGGATGATGGTCTTCTTAATCTTTTCCGGATACTTATTGCCAATAAAGAGTTGAACTCT
 A  D  A  Y  I  Q  G  D  F  S  F  V  D  K  D  D  G  L  L  N  L  F  R  I  L  I  A  N  K  E  L  N  S
GCCCTCAGGACAGAACAAAAGAAGGACTTGGCTGTCACCTGCACTGTTCACAGCTGGTATATCATCTGCAAAGTATTTCTTGAAGCATTACATGAGGCAA
 A  S  G  Q  N  K  R  R  T  W  L  S  P  A  L  F  T  A  G  I  S  S  A  K  Y  F  L  K  H  Y  M  R  Q
AATACTGTTACACAGGCTCGCAGGAACATTTCTCGTCATTATGACCTGAGTAATGAACTTTTCACTCTATACTTAGGTGAAATGATGCAATACTCTTCT
 N  T  V  T  Q  A  R  R  N  I  S  R  H  Y  D  L  S  N  E  L  F  T  L  Y  L  G  E  M  M  Q  Y  S  S
GGAATTTTTAAGACGGGAGAAGAACATTTGGACGTTGCACAGCGCAGAAAAATCAGTTCCTTAATTGATAAATCAAGAATAGAGAAGTGGCATGAAGTT
 G  I  F  K  T  G  E  E  H  L  D  V  A  Q  R  R  K  I  S  S  L  I  D  K  S  R  I  E  K  W  H  E  V
CTTGACATTGGATGTGGTTGGGGAAGCTTAGCTATGGAAGTTGTCAAAAGAACAGGATGTAAATACACTGGCATCACACTTTCAGACCAGCAACTGAAA
 L  D  I  G  C  G  W  G  S  L  A  M  E  V  V  K  R  T  G  C  K  Y  T  G  I  T  L  S  E  Q  Q  L  K
TATGCAGAAGAAAAAGTGAAGGAAGCTGGACTTCAGGGAAACATCAAATTTCTTCTTGCTGACTATCGCCAGTTACCCAAGACATTCAAATATGACAGA
 Y  A  E  E  K  V  K  E  A  G  L  Q  G  N  I  K  F  L  L  C  D  Y  R  Q  L  P  K  T  F  K  Y  D  R
ATCATATCTGTTGAGATGGTTGAACATGTTGGTGAAGAATATATTGAGGAGTTTTTCAGATGCTGTGACTCATTATTGGCAGAGAATGGGCTTTTCGTT
 I  I  S  V  E  M  V  E  H  V  G  E  E  Y  I  E  E  F  F  R  C  C  D  S  L  L  A  E  N  G  L  F  V
CTTCAGTTCATATCAATTCCAGAGATACTTTCCAAAGAAATCCAGCAAACAGCTGGTTTTCTAAAGGAATATATCTTCCCTGGTGGAACCCTGCTTTCT
 L  Q  F  I  S  I  P  E  I  L  S  K  E  I  Q  Q  T  A  G  F  L  K  E  Y  I  F  P  G  G  T  L  L  S
CTGGATAGGACTTTGTCAGCCATGGCTGCTGCATCAAGATTTAGTGTGGAGCATGTGGAAAATATAGGAATTAGTTATTATCACACACTGAGATGGTGG
 L  D  R  T  L  S  A  M  A  A  A  S  R  F  S  V  E  H  V  E  N  I  G  I  S  Y  Y  H  T  L  R  W  W
AGGAAAAATTTCTTGGCAAATGAAAGCAAAGTTCTGGCTTTGGGCTTCGATGAGAAGTTCATGCGGACATGGGAGTATTATTTTGATTACTGCGCAGCT
 R  K  N  F  L  A  N  E  S  K  V  L  A  L  G  F  D  E  K  F  M  R  T  W  E  Y  Y  F  D  Y  C  A  A
GGTTTTAAGACAGGGACACTTATAGATTACCAGGTTGTATTCTCACGGGCTGGCAATTTCGCTGCACTTGGCGATCCATACATAGGTTTCCCTTCAGCA
 G  F  K  T  G  T  L  I  D  Y  Q  V  V  F  S  R  A  G  N  F  A  A  L  G  D  P  Y  I  G  F  P  S  A
                        SacI     XhaI
    J0885  GGCTATTAACTTTATCAAAAGTAAATAGCCTCGAGTCTCCC
TATTCCTACTCGGATAATTGAAATAGTTTTCATTTATCCAAGGAAGTAGAGAAAACCACGCCATGATTCCGAATATCCAGATTGAGTCAACCAAGGATC
 Y  S  Y  S  D  N  stop
```

FIG 12

Amino Acid Sequence of the Protein Expressed in BL21 Cells

```
        ATGGGCAGCAGCCATCATCATCATCATCACAGCAGCGGCCTGGTGCCGCGCGGCAGCCATATGGCTAGCATGACTGGTGGACAGCAA
         M  G  S  S  H  H  H  H  H  H  S  S  G  L  V  P  R  G  S  H  M  A  S  M  T  G  G  Q  Q
              EcoRI
ATGGGTCGCGGATCCGAATTCTGTTCTCTTAAAACAGCTCTGAAAGTGCATAATCCTCAGTTTTACTGGAGGATTATGAAAGAAGCTGATATAGGCCTT
 M  G  R  G  S  E  F  C  S  L  K  T  A  L  K  V  H  N  P  Q  F  Y  W  R  I  M  K  E  A  D  I  G  L
GCTGATGCATATATCCAAGGAGATTTTTCTTTTGTTGACAAGGATGATGGTCTTCTTAATCTTTTCCGGATACTTATTGCCAATAAAGAGTTGAACTCT
 A  D  A  Y  I  Q  G  D  F  S  F  V  D  K  D  D  G  L  L  N  L  F  R  I  L  I  A  N  K  E  L  N  S
GCCTCAGGACAGAACAAAAGAAGGACTTGGCTGTCACCTGCACTGTTCACAGCTGGTATATCATCTGCAAAGTATTTCTTGAAGCATTACATGAGGCAA
 A  S  G  Q  N  K  R  R  T  W  L  S  P  A  L  F  T  A  G  I  S  S  A  K  Y  F  L  K  H  Y  M  R  Q
AATACTGTTACACAGGCTCGCAGGAACATTTCTCGTCATTATGACCTGAGTAATGAACTTTTCACTCTATACTTAGGTGAAATGATGCAATACTCTTCT
 N  T  V  T  Q  A  R  R  N  I  S  R  H  Y  D  L  S  N  E  L  P  T  L  Y  L  G  E  M  M  Q  Y  S  S
GGAATTTTTAAGACGGGAGAAGAACATTTGGACGTTGCACAGCGCAGAAAAATCAGTTCCTTAATTGATAAATCAAGAATAGAGAAGTGGCATGAAGTT
 G  I  F  K  T  G  E  E  H  L  D  V  A  Q  R  R  K  I  S  S  L  I  D  K  S  R  I  E  K  W  H  E  V
CTTGACATTGGATGTGGTTGGGGAAGCTTAGCTATGGAAGTTGTCAAAAGAACAGGATGTAAATACACTGGCATCACACTTTCAGAGCAGCAACTGAAA
 L  D  I  G  C  G  W  G  S  L  A  M  E  V  V  K  R  T  G  C  K  Y  T  G  I  T  L  S  E  Q  Q  L  K
TATGCAGAAGAAAAAGTGAAGGAAGCTGGACTTCAGGGAAACATCAAATTTCTTCTCTGTGACTATCGCCAGTTACCCAAGACATTCAAATATGACAGA
 Y  A  E  E  K  V  K  E  A  G  L  Q  G  N  I  K  F  L  L  C  D  Y  R  Q  L  P  K  T  F  K  Y  D  R
ATCATATCTGTTGAGATGGTTGAACATGTTGGTGAAGAATATATTGAGGAGTTTTTCAGATGCTGTGACTCATTATTGGCAGAGAATGGGCTTTTCGTT
 I  I  S  V  E  M  V  E  H  V  G  E  E  Y  I  E  E  F  F  R  C  C  D  S  L  L  A  E  N  G  L  F  V
CTTCAGTTCATATCAATTCCAGAGATACTTTCCAAAGAAATCCAGCAAACAGCTGGTTTTCTAAAGGAATATATTCCCTGGTGGAACCCTGCTTTCT
 L  Q  F  I  S  I  P  E  I  L  S  K  E  I  Q  Q  T  A  G  F  L  K  E  Y  I  F  P  G  G  T  L  L  S
CTGGATAGGACTTTGTCAGCCATGGCTGCTGCATCAAGATTTAGTGTGGAGCATGTGGAAAATATACCGAATTAGTTATTATCACACACTGAGATGGTGG
 L  D  R  T  L  S  A  M  A  A  A  S  R  F  S  V  E  H  V  E  N  I  G  I  S  Y  Y  H  T  L  R  W  W
AGGAAAAATTTCTTGGCAAATGAAAGCAAAGTTCTGGCTTTGGGGTTCGATGAGAAGTTCATGCGGACATGGGAGTATTATTTTGATTACTGCGCAGCT
 R  K  N  F  L  A  N  E  S  K  V  L  A  L  G  F  D  E  K  F  M  R  T  W  E  Y  Y  F  D  Y  C  A  A
GGTTTTAAGACAGGGACACTTATAGATTACCAGGTTGTATTCTCACGGGCTGGCAATTTCGCTGCACTTGGCGATCCATACATAGGTTTCCCTTCAGCA
 G  F  K  T  G  T  L  I  D  Y  Q  V  V  F  S  R  A  G  N  F  A  A  L  G  D  P  Y  I  G  F  P  S  A
TATTCCTACTCGGATAATTGAAATAGTTTTCATTTATCCGAGCTC
 Y  S  Y  S  D  N  *                  SacI
```

FIG 13

DNA Sequences of Cotton ESTs

A. EST1

GTTGAACCCTTTCAATTGGCAAAGCCTCAGAGAGATCATCAAATTCGGCAATGATGTCGAAAGTTACCTTGGATCACTTGAGAACAACC
CAGACATTGATCGTACTGAGACCTTGGGACAGTTTATAAACTCAAAGGGCTACTCTGAAAATTTTCAAAACACTTATCTGGCTCCTATA
TGTGGTTCAATGTGGTCAAGCTCCAAGGAAGATGTTACGAGCTTTTCAGCTTTTTCCATCCTTTCATTTTGCCGTACTCATCATTTGTA
CCAGCTATTTGGGCAGCCACAGTGGTTGACTATCAAAGGGCACTCACATTTTGTTAAAAGGGTTAGGGAAGTGCTGGAGACTAAAGGTT
GTCAATTTAAACTCGGTTGTGAAGTACAATCTGTTTTGCCTGTTGATAATGGTACCGCCATGGTCTGTGGAGATGGTTTCCAAGAAACT
TACAATGGATGCATTATGGCTGTTGATGCTCCCACTGCCCTAAAATTATTAGGAAACCAAGCAACATTTGAAGAAACAAGAGTACTGGG
TGCTTTCCAATATGCTACCAGTGATATTTTCCTTCACCAGGACAGTACTTTAATGCCACAAAACAAATCAGCTTGGAGTGCATTGAATT
TTCTCAATAGTAGCAAAAATAATGCATTCTTAACGTACTGGCTCAATGCACTACAAGATATTGGGGAAACAAGTGAGCCATTTTTTGTG
ACTGTCAATCCAGACCATACCCCAAAGAATACCTTACTTAAGTGGGCAACCGGCATGCAATTCCCTTGTGTGCTGCTCAAAAACTCACT
TGACTTGGTCAGATCAGGGAAGAAAGAATCTGGTCTGGGCTTTACTTCATAGGGAGAATAAAGCTGGATGGTTCTGACATGGAC

B. EST2

GTTCATTTCTCGTCATTATGATCTGAGTAATGAACTTTTCTCTCTATACTTGGGCAAAATGATGCAATACTCTTCTGGAGTCTTTAGGA
CAGGAGAAGAACATTTGGACGTTGCACAGCGAAGAAAAATCAGTTCTCTAATTGAGAAAACAAGGATAGAGAAATGGCATGAAGTTCTC
GACATTGGGTGCGGTTGGGGAAGCTTAGCTATTGAAACTGTGAAAAGAACAGGATGCAAATATACTGGCATCACTCTATCAGAACAGCA
ACTGAAATATGCTCAAGAAAAAGTGAAGGAAGCTGGACTCGAGGATAACATCAAAATACTTCTCTGTGACTATCGCCAGTTACCTAAGG
AACACCAATTTGACAGAATCATATCTGTAGAGATGGTAGAACATGTTGGTGAAGAATATATTGAGGAATTTTACAGATGCTGTGATCAA
TTACTGAAAGAAGATGGACTTTTCGTTCTTCAGTTCATATCAATCCCAGAGGAGCTTTCCAAAGAAATCCAGCAAACAGCTGGTTTTCT
TAAGGAATATATATTCCCTGGTGGAACCCTGCTTTCTTTGGATAGGAATNTATCAGCCATGGCTGCTGCAACAAGATTCAGTGTGGAGC
ACGTGGAAAACATANGAATGAGTTATTACCACACACTGAGATGGTGGA

C. EST3

AGGCCTCCCGCCCCTCACCCCTCCACCCCCTTCCCGCCCCTCACGGTCCACCCCGCCCTTTCCTACCCTACCCTCTAGCAATTTCCCC
CCCTCCCTTCCCCCCCCCCCTCCCTACCCTACGCCCTTTTCCTTCTTACCGTTCACACCAATCCCCCTGGAGCTTTCCCTAGCAATCCC
TAGCAACCCGCTGGTTTTCTTAAGCGTATACAATTTCCCTGGTGGACCCCTGCTTTCTTTGGATAGGCATTTATCAGCCATGGCTGCTG
CCACAAGATTCAGTGTGCAGCAGGTGGAACACATAGGAATGTGTTATTACCACCCACTGAGATGGTGGAGAAAACTTTTCCTGAAAACA
CAAGCAAAGTTCTGGCTTTGGGGTTCCCCCAGAAGTTCATCCGGACATGGGAATACTATTTCGATTACTGTGCTGCTGGTTTAAGACA
GGAACCCTTATAGATTCCCAGGTTGTATTTTCTCGAGCCGGTAATTTCGGTACACTTGGAGATCCATACAAAGGTTTCCCTTCTGCATA
TTCCTTCATGGATGATTGAACAAAGTGTTTGAATATATGATCCCCATACCATGATTCACCCAGCTGGATCCAACTGGTACCAGTGTTTC
CCCAGTCCCCTGCTTTTGTTTAGTTATGGTTTTCGTTTCGTTCCGAAAAAGAAATAAGCCAATAATGTATGTTAATAATGAAATGTTTG
TATCTGGTATATCTATACTGGTTGGATTTTATGTATGGAGATGCTGTTTGCTTTTTGAAGAAGAAACCCCACCACCCCCC

FIG 14

C. Contig1 (EST2_3)

```
GTTCATTTCTCGTCATTATGATCTGAGTAATGAACTTTTCTCTCTATACTTGGGCAAAATGATGCAATACTCTTCTGGAGTCTTTAGGA
CAGGAGAAGAACATTTGGACGTTGCACAGCGAAGAAAAATCAGTTCTCTAATTGAGAAAACAAGGATAGAGAAATGGCATGAAGTTCTC
GACATTGGGTGCGGTTGGGGAAGCTTAGCTATTGAAACTGTGAAAAGAACAGGATGCAAATATACTGGCATCACTCTATCAGAACAGCA
ACTGAAATATGCTCAAGAAAAAGTGAAGGAAGCTGGACTCGAGGATAACATCAAAATACTTCTCTGTGACTATCGCCAGTTACCTAAGG
AACACCAATTTGACAGAATCATATCTGTAGAGATGGTAGAACATGTTGGTGAAGAATATATTGAGGAATTTTACAGATGCTGTGATCAA
TTACTGAAAGAAGATGGACTTTTCGTTCTTCAGTTCATATCAATCCCAGAGGAGCTTTCCAAAGAAATCCAGCAAACAGCTGGTTTTCT
TAAGGAATATATATTCCCTGGTGGAACCCTGCTTTCTTTGGATAGGAAT TATCAGCCATGGCTGCTGCAACAAGATTCAGTGTGGAGC
AGGTGGAACACATAGGAATGTGTTATTACCACCCACTGAGATGGTGGAGAAAACTTTTCCTGAAAACACAAGCAAAGTTCTGGCTTTGG
GGTTCCCCCAGAAGTTCATCCGGACATGGGAATACTATTTCGATTACTGTGCTGCTGGTTTTAAGACAGGAACCCTTATAGATTCCCAG
GTTGTATTTTCTCGAGCCGGTAATTTCGGTACACTTGGAGATCCATACAAAGGTTTCCCTTCTGCATATTCCTTCATGGATGATTGAAC
AAAGTGTTTGAATATATGATCCCCATACCATGATTCACCCAGCTGGATCCAACTGGTACCAGTGTTTCCCCAGTCCCTGCTTTTGTTT
AGTTATGGTTTTCGTTTCGTTCCGAAAAAGAAATAAGCCAATAATGTATGTTAATAATGAAATGTTTGTATCTGGTATATCTATACTGG
TTGGATTTTATGTATGGAGATGCTGTTTGCTTTTTGAAGAAGAAACCCCACCACCCCC
```

FIG 15 CONT

Predicted Amino Acid Sequences

A. *Sterculia* Cyclopropane Fatty Acid Synthase

```
MGVAVIGGGIQGLVSAYVLAKAGVNVVVYEKEEQVGGHAKTVSFDAVDLDLGLLFLNPA
RYPTMLELFDSLEVDVEATDVSFSVSHDKGNGYEWCSQYGFSNFLAHKKKMLNPYNWQD
LRETIKFGNDVNSYLESLEKNPDIDRNETLGHFVGSKGYSENFLNTYLAPICGSMWSCS
KEEVMSFSAYSILSFCRTYHLYQLFGNPQWLTIKRHSYLVKKVRDILESRGCQFKLGCE
VLSVLPADDGSSIVFGDGFQETYNGCIMAVNAPTALKILGNQATFEEMRVLGAFQYASS
DIYLHRDSNLMPTNRSGWSALNFLRSRENKASLTYWLNVLQNVGKTSQPFFVTLNPDRI
PDKILLKWSTGRPIPSVAASKASLELDQIQGKRGIWFCGYDFHEDELKAGMDAAHRILG
KHFSVLLSPRQMSPSFMETTARLLVTKFFHQYIQVGCVIIIEEGGRVYTFKGSMENCSL
KTALKVHNPQFYWRIMKEADIGLADAYIQGDFSFVDKDDGLLNLFRILIANKELNSASG
QNKRRTWLSPALFTAGISSAKYFLKHYMRQNTVTQARRNISRHYDLSNELFTLYLGEMM
QYSSGIFKTGEEHLDVAQRRKISSLIDKSRIEKWHEVLDIGCGWGSLAMEVVKRTGCKY
TGITLSEQQLKYAEEKVKEAGLQGNIKFLLCDYRQLPKTFKYDRIISVEMVDMVGEEYI
EEFFRCCDSLLAENGLFVLQFISIPEILSKEIQQTAGFLKEYIFPGGTLLSLDRTLSAM
AAASRFSVEHVENIGISYYHTLRWWRKNFLANESKVLALGFDEKFMRTWEYYFDYCAAG
FKTGTLIDYQVVFSRAGNFAALGDPYIGFPSAYSYSDN
```

B. EST1

```
LNPFNWQSLREIIKFGNDVESYLGSLENNPDIDRTETLGQFINSKGYSENFQNTYLAPI
CGSMWSSSKEDVTSFSAFSILSFCRTHHLYQLFGQPQWLTIKGHSHFVKRVREVLETKG
CQFKLGCEVQSVLPVDNGTAMVCGDGFQETYNGCIMAVDAPTALKLLGNQATFEETRVL
GAFQYATSDIFLHQDSTLMPQNKSAWSALNFLNSSKNNAFLTYWLNALQDIGETSEPFF
VTVNPDHTPKNTLLKWATGMQFPCVLLKNSLDLVRSGKKESGLGFTS
```

C. EST2

```
FISRHYDLSNELFSLYLGKMMQYSSGVFRTGEEHLDVAQRRKISSLIEKTRIEKWHEVL
DIGCGWGSLAIETVKRTGCKYTGITLSEQQLKYAQEKVKEAGLEDNIKILLCDYRQLPK
EHQFDRIISVEMVEHVGEEYIEEFYRCCDQLLKEDGLFVLQFISIPEELSKEIQQTAGF
LKEYIFPGGTLLSLDRNXSAMAAATRFSVEHVENIXMSYYHTLRWW
```

D. EST3

```
FLSVYIFPGGPLLSLDRHLSAMAAATRFSVQQVEHIGMCYYHPLRWWRKLFLKTFPENT
SKVLALGFPQKFIRTWEYYFDYCAAGFKTGTLIDSQVVFSRAGNFGTLGDPYKGFPSAY
SFMDD
```

E. EST2_3 (Contig 1)

FIG 16

```
FISRHYDLSNELFSLYLGKMMQYSSGVFRTGEEHLDVAQRRKISSLIEKTRIEKWHEVL
DIGCGWGSLAIETVKRTGCKYTGITLSEQQLKYAQEKVKEAGLEDNIKILLCDYRQLPK
EHQFDRIISVEMVEHVGEEYIEEFYRCCDQLLKEDGLFVLQFISIPEELSKEIQQTAGF
LKEYIFPGGTLLSLDRNLSAMAAATRFSVEQVEHIGMCYYHPLRWWRKLFLENTSKVLA
LGFPQKFIRTWEYYFDYCAAGFKTGTLIDSQVVFSRAGNFGTLGDPYKGFPSAYSFMDD
```

FIG 16 CONT

Alignment of Amino Acid Sequences

```
                1                                                           60
Sterculia   (1) MGVAVIGGGIQGLVSAYVLAKAGVNVVVYEKEEQVGGHAKTVSFDAVDLDLGLLFLNPAR
EST1        (1) ------------------------------------------------------------
EST2_3      (1) ------------------------------------------------------------
                61                                                          120
Sterculia  (61) YPTMLELFDSLEVDVEATDVSFSVSHDKGNGYEWCSQYGFSNFLAHKKKMLNPYNWQDLR
EST1        (1) ---------------------------------------------LNPFNWQSLR
EST2_3      (1) ------------------------------------------------------------
                121                                                         180
Sterculia (121) ETIKFGNDVNSYLESLEKNPDIDRNETLGHFVGSKGYSENFLNTYLAPICGSMWSCSKEE
EST1       (11) EIIKFGNDVESYLGSLENNPDIDRTETLGQFINSKGYSENFQNTYLAPICGSMWSSSKED
EST2_3      (1) ------------------------------------------------------------
                181                                                         240
Sterculia (181) VMSFSANSILSFCRTYHLYQLFGNPQWLTIKRHSYLVKKVRDILEGRGCQFKLGCEVLSV
EST1       (71) VTSFSANSILSFCRTIHLYQLFGQPQWLTIKGHSHFVKKVREVLEIKGCQFKLGCEVQSV
EST2_3      (1) ------------------------------------------------------------
                241                                                         300
Sterculia (241) LPADDGSSIVFGDGFQETYNGCIMAVNAPTALKILGNQATFEEMRVLGAFQYASSDIYLH
EST1      (131) LPVDNGTAMVCGDGFQETYNGCIMAVDAPTALKILGNQATFEETRVLGAFQYASSDIFLH
EST2_3      (1) ------------------------------------------------------------
                301                                                         360
Sterculia (301) RDSNLMPTNRSGWSALNFLRSRENKASLTYWLNVLQNYGKTSQPFFVTLNPDRIPDKILL
EST1      (191) QDSTLMPQNKSAWSALNFLNSSKNNAFLTYWLNALQDIGETSEPFFVTVNPDHTPKNTLL
EST2_3      (1) ------------------------------------------------------------
                361                                                         420
Sterculia (361) KWSTGRPIFSVAASKASLELDQIQGKRGIWFCGYDFHEDELKAGMDAAHRILGKHFSVLL
EST1      (251) KWATGMQFTCVLLKNSLDLVRSGKKESGLGFTS-GE-SWMVLTW----------------
EST2_3      (1) ------------------------------------------------------------
                421                                                         480
Sterculia (421) SPRQMSPSFMETTARLLVTKFFHQYIQVGCVIIIEEGGRVYTFKGSMENCSLKTALKVHN
EST1      (293) ------------------------------------------------------------
EST2_3      (1) ------------------------------------------------------------
                481                                                         540
Sterculia (481) PQFYWRIMKEADIGLADAYIQGDFSFVDKDDGLLNLFRILIANKELNSASGQNKRRTWLS
EST1      (293) ------------------------------------------------------------
EST2_3      (1) ------------------------------------------------------------
                541                                                         600
Sterculia (541) PALFTAGISSAKYFLKHYMRQNTVTQARRNISRHYDLSNELFTLYLGEMMQYSSGFFKTG
EST1      (293) ------------------------------------------------------------
EST2_3      (1) ---------------------------FISRHYDLSNELFSLYLGKMMQYSSCVFKTG
                601                                                         660
Sterculia (601) EEHLDVAQRRKISSLIDKSRIEKWHEVLDIGCGWGSLAMEVVKRTGCKYTGITLSEQQLK
EST1      (293) ------------------------------------------------------------
EST2_3     (32) EEHLDVAQRRKISSLIEKSRIEKWHEVLDIGCGWGSLAIETVKRTGCKYTGITLSEQQLK
                661                                                         720
Sterculia (661) YAEEKVKEAGLQCNIKFLLCDYRQLPKTFKYDRIISVEMVDMVGEEYIEFFRCCDSLLA
EST1      (293) ------------------------------------------------------------
EST2_3     (92) YAQEKVKEAGLEDNIKILLCDYRQLPKEHQKDRIISVEMVEHVGEEYIEEFYRCCDQLIK
                721                                                         780
Sterculia (721) ENGLFVLQFISIPEILSKEIQQTAGFLKEYIFPGGTLLSLDRTLSAMAAASRFSVEHVEN
EST1      (293) ------------------------------------------------------------
EST2_3    (152) EDGLFVLQFISIPEELSKEIQQTAGFLKEYIFPGGTLLSLDRNLSAMAAADRFSVBQVEH
                781                                                         840
Sterculia (781) IGISYYHTLRWWRKNFLANESKVLALGFDEKFMRTWEYYFDYCAAGFKTGTLIDYQVVFS
EST1      (293) ------------------------------------------------------------
EST2_3    (212) IGMCYYHPLRWWRKLFLENTSKVLALGFPQKFIRTWEYYFDYCAAGFKTGTLIDSQVVFS
                841           864
Sterculia (841) RAGNFSALGDPYIGFPSAYSYSDN
EST1      (293) ------------------------
EST2_3    (272) RAGNFGTLGDPYKGFPSAYSEMDD
```

FIG 17

SEQUENCE LISTING

<160> NUMBER OF SEQ ID NOS: 35

<210> SEQ ID NO 1
<211> LENGTH: 2595

```
<212> TYPE: DNA
<213> ORGANISM: Sterculia cyclopropane fatty acid synthase

<400> SEQUENCE: 1
atgggagtgg ctgtgatcgg tggtgggatc caagggctgg tttcggccta cgttcttgcc      60
aaagccggcg tcaacgtcgt tgtttacgag aaagaggagc aagtaggtgg ccatgccaag     120
actgttagct tgacgccgt cgatttggac cttggcctct tgtttctcaa ccctgcaagg      180
tatccaacaa tgttggagct gtttgatagc cttgaagttg atgtggaggc aactgatgtt     240
tcattctctg taagccatga caaaggcaat ggctatgaat ggtgcagcca gtacggtttt     300
tcgaactttt tagcacacaa gaagaaaatg ttgaatcctt acaattggca agacctcaga     360
gaaactatca agttcggaaa tgatgtcaat agttatcttg aatcgcttga aagaatcct      420
gacattgatc gtaatgaaac cttggggcat tttgtagggt caagggtta ctctgaaaat      480
tttctgaaca cttacctggc tccaatatgt ggttcaatgt ggtcctgctc caaggaagaa     540
gttatgagct tttcagccta ctccattctt tcgttttgtc gcacttatca tctgtaccag     600
ctatttggga atccacagtg gctgactatt aaaaggcact catatttagt taaaaaggtc     660
agagatattc tggaaagcag aggttgtcag tttaaacttg gttgtgaagt gctttctgtt     720
ttgcctgctg atgatggtag ctccatagtc tttggagatg gtttccaaga aacgtacaat     780
ggatgcataa tggctgttaa tgctcccaca gccctaaaaa tattaggaaa ccaagcaaca     840
tttgaagaaa tgagagttct gggtgcattc caatatgctt ccagtgatat ttaccttcac     900
cgtgacagca atttaatgcc cacaaacaga tcaggttgga gtgcactgaa ttttctcaga     960
agtagagaaa ataaagcaag cttaacatac tggctcaatg tgctacagaa tgttgggaaa    1020
acaagtcagc cctttttgt gactctcaat ccagaccgta tcccagacaa aatcttgctt    1080
aagtggtcga ctggacgtcc aattccctct gttgctgcat caaaagcttc acttgagcta    1140
gatcagattc aggggaagag aggaatctgg ttctgtggct atgacttcca tgaggatgaa    1200
ttaaaggctg gtatggatgc tgcacatcgt atcttgggaa agcatttttc tgttctgcac    1260
agtccaaggc aaatgtcacc ctcttttcatg gaaacaacgg cacgtcttct tgttactaaa    1320
ttctttcacc aatatataca gtgggctgc gtaataatca tagaggaagg tggcagagtt    1380
tacactttca aaggaagcat ggaaaattgt tctcttaaaa cagctctgaa agtgcataat    1440
cctcagttttt actggaggat tatgaaagaa gctgatatag ccttgctga tgcatatatc    1500
caaggagatt tttcttttgt tgacaaggat gatggtcttc ttaatctttt ccggatactt    1560
attgccaata aagagttgaa ctctgcctca ggacagaaca aagaaggac ttggctgtca    1620
cctgcactgt tcagctggg tatatcatct gcaaagtatt tcttgaagca ttacatgagg    1680
caaaatactg ttacacaggc tcgcaggaac atttctcgtc attatgacct gagtaatgaa    1740
cttttcactc tatacttagg tgaaatgatg caatactctt ctggaatttt taagacggga    1800
gaagaacatt tggacgttgc acagcgcaga aaaatcagtt ccttaattga taaatcaaga    1860
atagagaagt ggcatgaagt tcttgacatt ggatgtggtt ggggaagctt agctatggaa    1920
gttgtcaaaa gaacaggatg taaatacact ggcatcacac tttcagagca gcaactgaaa    1980
tatgcagaag aaaaagtgaa ggaagctgga cttcagggaa acatcaaatt tcttctctgt    2040
gactatcgcc agttacccaa gacattcaaa tatgacagaa tcatatctgt tgagatggtt    2100
gaacatgttg gtgaagaata tattgaggag ttttcagat gctgtgactc attattggca    2160
gagaatgggc ttttcgttct tcagttcata tcaattccag agatacttc caaagaaatc    2220
```

-continued

```
cagcaaacag ctggttttct aaaggaatat atcttccctg gtggaaccct gctttctctg    2280
gataggactt tgtcagccat ggctgctgca tcaagattta gtgtggagca tgtggaaaat    2340
ataggaatta gttattatca cacactgaga tggtggagga aaaatttctt ggcaaatgaa    2400
agcaaagttc tggctttggg gttcgatgag aagttcatgc ggacatggga gtattatttt    2460
gattactgcg cagctggttt taagacaggg acacttatag attaccaggt tgtattctca    2520
cgggctggca atttcgctgc acttggcgat ccatacatag gtttcccttc agcatattcc    2580
tactcggata attga                                                    2595
```

<210> SEQ ID NO 2
<211> LENGTH: 864
<212> TYPE: PRT
<213> ORGANISM: Sterculia cyclopropane fatty acid synthase

<400> SEQUENCE: 2

```
Met Gly Val Ala Val Ile Gly Gly Ile Gln Gly Leu Val Ser Ala
  1               5                  10                  15

Tyr Val Leu Ala Lys Ala Gly Val Asn Val Val Tyr Glu Lys Glu
                 20                  25                  30

Glu Gln Val Gly Gly His Ala Lys Thr Val Ser Phe Asp Ala Val Asp
                 35                  40                  45

Leu Asp Leu Gly Leu Leu Phe Leu Asn Pro Ala Arg Tyr Pro Thr Met
 50                  55                  60

Leu Glu Leu Phe Asp Ser Leu Glu Val Asp Val Glu Ala Thr Asp Val
 65                  70                  75                  80

Ser Phe Ser Val Ser His Asp Lys Gly Asn Gly Tyr Glu Trp Cys Ser
                 85                  90                  95

Gln Tyr Gly Phe Ser Asn Phe Leu Ala His Lys Lys Lys Met Leu Asn
                100                 105                 110

Pro Tyr Asn Trp Gln Asp Leu Arg Glu Thr Ile Lys Phe Gly Asn Asp
                115                 120                 125

Val Asn Ser Tyr Leu Glu Ser Leu Glu Lys Asn Pro Asp Ile Asp Arg
                130                 135                 140

Asn Glu Thr Leu Gly His Phe Val Gly Ser Lys Gly Tyr Ser Glu Asn
145                 150                 155                 160

Phe Leu Asn Thr Tyr Leu Ala Pro Ile Cys Gly Ser Met Trp Ser Cys
                165                 170                 175

Ser Lys Glu Glu Val Met Ser Phe Ser Ala Tyr Ser Ile Leu Ser Phe
                180                 185                 190

Cys Arg Thr Tyr His Leu Tyr Gln Leu Phe Gly Asn Pro Gln Trp Leu
                195                 200                 205

Thr Ile Lys Arg His Ser Tyr Leu Val Lys Lys Val Arg Asp Ile Leu
                210                 215                 220

Glu Ser Arg Gly Cys Gln Phe Lys Leu Gly Cys Glu Val Leu Ser Val
225                 230                 235                 240

Leu Pro Ala Asp Asp Gly Ser Ser Ile Val Phe Gly Asp Gly Phe Gln
                245                 250                 255

Glu Thr Tyr Asn Gly Cys Ile Met Ala Val Asn Ala Pro Thr Ala Leu
                260                 265                 270

Lys Ile Leu Gly Asn Gln Ala Thr Phe Glu Glu Met Arg Val Leu Gly
                275                 280                 285

Ala Phe Gln Tyr Ala Ser Ser Asp Ile Tyr Leu His Arg Asp Ser Asn
                290                 295                 300
```

```
Leu Met Pro Thr Asn Arg Ser Gly Trp Ser Ala Leu Asn Phe Leu Arg
305                 310                 315                 320

Ser Arg Glu Asn Lys Ala Ser Leu Thr Tyr Trp Leu Asn Val Leu Gln
                325                 330                 335

Asn Val Gly Lys Thr Ser Gln Pro Phe Phe Val Thr Leu Asn Pro Asp
            340                 345                 350

Arg Ile Pro Asp Lys Ile Leu Leu Lys Trp Ser Thr Gly Arg Pro Ile
        355                 360                 365

Pro Ser Val Ala Ala Ser Lys Ala Ser Leu Glu Leu Asp Gln Ile Gln
    370                 375                 380

Gly Lys Arg Gly Ile Trp Phe Cys Gly Tyr Asp Phe His Glu Asp Glu
385                 390                 395                 400

Leu Lys Ala Gly Met Asp Ala Ala His Arg Ile Leu Gly Lys His Phe
                405                 410                 415

Ser Val Leu Leu Ser Pro Arg Gln Met Ser Pro Ser Phe Met Glu Thr
            420                 425                 430

Thr Ala Arg Leu Leu Val Thr Lys Phe Phe His Gln Tyr Ile Gln Val
        435                 440                 445

Gly Cys Val Ile Ile Ile Glu Glu Gly Arg Val Tyr Thr Phe Lys
    450                 455                 460

Gly Ser Met Glu Asn Cys Ser Leu Lys Thr Ala Leu Lys Val His Asn
465                 470                 475                 480

Pro Gln Phe Tyr Trp Arg Ile Met Lys Glu Ala Asp Ile Gly Leu Ala
                485                 490                 495

Asp Ala Tyr Ile Gln Gly Asp Phe Ser Phe Val Asp Lys Asp Asp Gly
            500                 505                 510

Leu Leu Asn Leu Phe Arg Ile Leu Ile Ala Asn Lys Glu Leu Asn Ser
        515                 520                 525

Ala Ser Gly Gln Asn Lys Arg Arg Thr Trp Leu Ser Pro Ala Leu Phe
    530                 535                 540

Thr Ala Gly Ile Ser Ser Ala Lys Tyr Phe Leu Lys His Tyr Met Arg
545                 550                 555                 560

Gln Asn Thr Val Thr Gln Ala Arg Arg Asn Ile Ser Arg His Tyr Asp
                565                 570                 575

Leu Ser Asn Glu Leu Phe Thr Leu Tyr Leu Gly Glu Met Met Gln Tyr
            580                 585                 590

Ser Ser Gly Ile Phe Lys Thr Gly Glu Glu His Leu Asp Val Ala Gln
        595                 600                 605

Arg Arg Lys Ile Ser Ser Leu Ile Asp Lys Ser Arg Ile Glu Lys Trp
    610                 615                 620

His Glu Val Leu Asp Ile Gly Cys Gly Trp Gly Ser Leu Ala Met Glu
625                 630                 635                 640

Val Val Lys Arg Thr Gly Cys Lys Tyr Thr Gly Ile Thr Leu Ser Glu
                645                 650                 655

Gln Gln Leu Lys Tyr Ala Glu Glu Lys Val Lys Glu Ala Gly Leu Gln
            660                 665                 670

Gly Asn Ile Lys Phe Leu Leu Cys Asp Tyr Arg Gln Leu Pro Lys Thr
        675                 680                 685

Phe Lys Tyr Asp Arg Ile Ile Ser Val Glu Met Val Asp Met Val Gly
    690                 695                 700

Glu Glu Tyr Ile Glu Glu Phe Arg Cys Cys Asp Ser Leu Leu Ala
705                 710                 715                 720

Glu Asn Gly Leu Phe Val Leu Gln Phe Ile Ser Ile Pro Glu Ile Leu
```

```
                725             730             735
Ser Lys Glu Ile Gln Gln Thr Ala Gly Phe Leu Lys Glu Tyr Ile Phe
            740                 745                 750

Pro Gly Gly Thr Leu Leu Ser Leu Asp Arg Thr Leu Ser Ala Met Ala
        755                 760                 765

Ala Ala Ser Arg Phe Ser Val Glu His Val Glu Asn Ile Gly Ile Ser
    770                 775                 780

Tyr Tyr His Thr Leu Arg Trp Trp Arg Lys Asn Phe Leu Ala Asn Glu
785                 790                 795                 800

Ser Lys Val Leu Ala Leu Gly Phe Asp Glu Lys Phe Met Arg Thr Trp
            805                 810                 815

Glu Tyr Tyr Phe Asp Tyr Cys Ala Ala Gly Phe Lys Thr Gly Thr Leu
        820                 825                 830

Ile Asp Tyr Gln Val Val Phe Ser Arg Ala Gly Asn Phe Ala Ala Leu
    835                 840                 845

Gly Asp Pro Tyr Ile Gly Phe Pro Ser Ala Tyr Ser Tyr Ser Asp Asn
850                 855                 860
```

<210> SEQ ID NO 3
<211> LENGTH: 885
<212> TYPE: DNA
<213> ORGANISM: Gossypium arboreum

<400> SEQUENCE: 3

```
gttgaaccct tcaattggc aaagcctcag agagatcatc aaattcggca atgatgtcga      60
aagttacctt ggatcacttg agaacaaccc agacattgat cgtactgaga ccttgggaca     120
gtttataaac tcaaagggct actctgaaaa ttttcaaaac acttatctgg ctcctatatg     180
tggttcaatg tggtcaagct ccaaggaaga tgttacgagc ttttcagctt tttccatcct    240
ttcattttgc cgtactcatc atttgtacca gctatttggg cagccacagt ggttgactat     300
caaagggcac tcacattttg ttaaaagggt tagggaagtg ctggagacta aggttgtca     360
atttaaactc ggttgtgaag tacaatctgt tttgcctgtt gataatggta ccgccatggt     420
ctgtggagat ggtttccaag aaacttacaa tggatgcatt atggctgttg atgctcccac    480
tgccctaaaa ttattaggaa ccaagcaac atttgaagaa caagagtac tgggtgcttt     540
ccaatatgct accagtgata tttccttca ccaggacagt actttaatgc acaaaacaa      600
atcagcttgg agtgcattga ttttctcaa tagtagcaaa ataatgcat tcttaacgta     660
ctggctcaat gcactacaag atattgggga acaagtgag ccatttttg tgactgtcaa    720
tccagaccat accccaaaga ataccttact taagtgggca accggcatgc aattcccttg     780
tgtgctgctc aaaaactcac ttgacttggt cagatcaggg aagaaagaat ctggtctggg     840
ctttacttca tagggagaat aaagctggat ggttctgaca tggac                    885
```

<210> SEQ ID NO 4
<211> LENGTH: 671
<212> TYPE: DNA
<213> ORGANISM: Gossypium arboreum
<220> FEATURE:
<221> NAME/KEY: misc_feature
<222> LOCATION: (584)..(584)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t

<400> SEQUENCE: 4

```
gttcatttct cgtcattatg atctgagtaa tgaactttc tctctatact tgggcaaaat      60
gatgcaatac tcttctggag tctttaggac aggagaagaa catttggacg ttgcacagcg    120
aagaaaaatc agttctctaa ttgagaaaac aaggatagag aaatggcatg aagttctcga    180
cattgggtgc ggttggggaa gcttagctat tgaaactgtg aaaagaacag gatgcaaata    240
tactggcatc actctatcag aacagcaact gaaatatgct caagaaaaag tgaaggaagc    300
tggactcgag ataacatca aaatacttct ctgtgactat cgccagttac ctaaggaaca    360
ccaatttgac agaatcatat ctgtagagat ggtagaacat gttggtgaag aatatattga    420
ggaattttac agatgctgtg atcaattact gaaagaagat ggacttttcg ttcttcagtt    480
catatcaatc ccagaggagc tttccaaaga aatccagcaa acagctggtt ttcttaagga    540
atatatattc cctggtggaa ccctgctttc tttggatagg aatntatcag ccatggctgc    600
tgcaacaaga ttcagtgtgg agcacgtgga aaacatanga atgagttatt accacacact    660
gagatggtgg a                                                          671

<210> SEQ ID NO 5
<211> LENGTH: 792
<212> TYPE: DNA
<213> ORGANISM: Gossypium arboreum

<400> SEQUENCE: 5
aggcctcccg cccctcaccc ctccaccccc ttcccgcccc tcacggtcca ccccgccct     60 ttcctacccct accctctagc aatttccccc cctcccttcc ccccccccct ccctacccta    120 cgccctttc cttcttaccg ttcacaccaa tcccctggaa gctttcccta gcaatccta     180 gcaacccgct ggttttctta agcgtataca atttccctgg tggacccctg ctttctttgg    240
ataggcattt atcagccatg gctgctgcca caagattcag tgtgcagcag gtggaacaca    300
taggaatgtg ttattaccac ccactgagat ggtggagaaa actttcctg aaaacacaag    360 caaagttctg gctttggggt tccccagaa gttcatccgg acatgggaat actatttcga    420
ttactgtgct gctggttta agacaggaac ccttatagat tcccaggttg tatttctcg     480 agccggtaat ttcggtacac ttggagatcc atacaaaggt ttcccttctg catattcctt    540
catggatgat tgaacaaagt gtttgaatat atgatcccca taccatgatt cacccagctg    600
gatccaactg gtaccagtgt ttccccagtc ccctgctttt gtttagttat ggttttcgtt    660
tcgttccgaa aaagaaataa gccaataatg tatgttaata atgaaatgtt tgtatctggt    720
atatctatac tggttggatt ttatgtatgg agatgctgtt tgcttttga agaagaaacc     780 ccaccaccccc cc                                                        792

<210> SEQ ID NO 6
<211> LENGTH: 1126
<212> TYPE: DNA
<213> ORGANISM: Gossypium arboreum

<400> SEQUENCE: 6
gttcatttct cgtcattatg atctgagtaa tgaactttc tctctatact tgggcaaaat      60
gatgcaatac tcttctggag tctttaggac aggagaagaa catttggacg ttgcacagcg    120
aagaaaaatc agttctctaa ttgagaaaac aaggatagag aaatggcatg aagttctcga    180
cattgggtgc ggttggggaa gcttagctat tgaaactgtg aaaagaacag gatgcaaata    240
tactggcatc actctatcag aacagcaact gaaatatgct caagaaaaag tgaaggaagc    300
```

```
tggactcgag gataacatca aaatacttct ctgtgactat cgccagttac ctaaggaaca    360
ccaatttgac agaatcatat ctgtagagat ggtagaacat gttggtgaag aatatattga    420
ggaattttac agatgctgtg atcaattact gaaagaagat ggacttttcg ttcttcagtt    480
catatcaatc ccagaggagc tttccaaaga aatccagcaa acagctggtt ttcttaagga    540
atatatattc cctggtggaa ccctgctttc tttggatagg aatttatcag ccatggctgc    600
tgcaacaaga ttcagtgtgg agcaggtgga acacatagga atgtgttatt accacccact    660
gagatggtgg agaaaacttt tcctgaaaac acaagcaaag ttctggcttt ggggttcccc    720
cagaagttca tccggacatg gaatactat ttcgattact gtgctgctgg ttttaagaca    780 ggaacccta tagattccca ggttgtattt tctcgagccg gtaatttcgg tacacttgga    840
gatccataca aaggtttccc ttctgcatat tccttcatgg atgattgaac aaagtgtttg    900
aatatatgat ccccatacca tgattcaccc agctggatcc aactggtacc agtgtttccc    960
cagtcccctg cttttgttta gttatggttt tcgtttcgtt ccgaaaaaga aataagccaa   1020
taatgtatgt taataatgaa atgtttgtat ctggtatatc tatactggtt ggattttatg   1080
tatggagatg ctgtttgctt tttgaagaag aaaccccacc accccc               1126
```

<210> SEQ ID NO 7
<211> LENGTH: 283
<212> TYPE: PRT
<213> ORGANISM: Gossypium arboreum

<400> SEQUENCE: 7

```
Leu Asn Pro Phe Asn Trp Gln Ser Leu Arg Glu Ile Ile Lys Phe Gly
1               5                   10                  15

Asn Asp Val Glu Ser Tyr Leu Gly Ser Leu Glu Asn Asn Pro Asp Ile
            20                  25                  30

Asp Arg Thr Glu Thr Leu Gly Gln Phe Ile Asn Ser Lys Gly Tyr Ser
        35                  40                  45

Glu Asn Phe Gln Asn Thr Tyr Leu Ala Pro Ile Cys Gly Ser Met Trp
    50                  55                  60

Ser Ser Ser Lys Glu Asp Val Thr Ser Phe Ala Phe Ser Ile Leu
65                  70                  75                  80

Ser Phe Cys Arg Thr His His Leu Tyr Gln Leu Phe Gly Gln Pro Gln
                85                  90                  95

Trp Leu Thr Ile Lys Gly His Ser His Phe Val Lys Arg Val Arg Glu
            100                 105                 110

Val Leu Glu Thr Lys Gly Cys Gln Phe Lys Leu Gly Cys Glu Val Gln
        115                 120                 125

Ser Val Leu Pro Val Asp Asn Gly Thr Ala Met Val Cys Gly Asp Gly
    130                 135                 140

Phe Gln Glu Thr Tyr Asn Gly Cys Ile Met Ala Val Asp Ala Pro Thr
145                 150                 155                 160

Ala Leu Lys Leu Leu Gly Asn Gln Ala Thr Phe Glu Glu Thr Arg Val
                165                 170                 175

Leu Gly Ala Phe Gln Tyr Ala Thr Ser Asp Ile Phe Leu His Gln Asp
            180                 185                 190

Ser Thr Leu Met Pro Gln Asn Lys Ser Ala Trp Ser Ala Leu Asn Phe
        195                 200                 205

Leu Asn Ser Ser Lys Asn Asn Ala Phe Leu Thr Tyr Trp Leu Asn Ala
    210                 215                 220

Leu Gln Asp Ile Gly Glu Thr Ser Glu Pro Phe Phe Val Thr Val Asn
```

```
                   225                 230                 235                 240

Pro Asp His Thr Pro Lys Asn Thr Leu Leu Lys Trp Ala Thr Gly Met
                        245                 250                 255

Gln Phe Pro Cys Val Leu Leu Lys Asn Ser Leu Asp Leu Val Arg Ser
                260                 265                 270

Gly Lys Lys Glu Ser Gly Leu Gly Phe Thr Ser
            275                 280

<210> SEQ ID NO 8
<211> LENGTH: 223
<212> TYPE: PRT
<213> ORGANISM: Gossypium arboreum
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid

<400> SEQUENCE: 8

Phe Ile Ser Arg His Tyr Asp Leu Ser Asn Glu Leu Phe Ser Leu Tyr
1               5                   10                  15

Leu Gly Lys Met Met Gln Tyr Ser Ser Gly Val Phe Arg Thr Gly Glu
            20                  25                  30

Glu His Leu Asp Val Ala Gln Arg Lys Ile Ser Ser Leu Ile Glu
        35                  40                  45

Lys Thr Arg Ile Glu Lys Trp His Glu Val Leu Asp Ile Gly Cys Gly
50                  55                  60

Trp Gly Ser Leu Ala Ile Glu Thr Val Lys Arg Thr Gly Cys Lys Tyr
65                  70                  75                  80

Thr Gly Ile Thr Leu Ser Glu Gln Gln Leu Lys Tyr Ala Gln Glu Lys
                85                  90                  95

Val Lys Glu Ala Gly Leu Glu Asp Asn Ile Lys Ile Leu Leu Cys Asp
            100                 105                 110

Tyr Arg Gln Leu Pro Lys Glu His Gln Phe Asp Arg Ile Ile Ser Val
        115                 120                 125

Glu Met Val Glu His Val Gly Glu Glu Tyr Ile Glu Glu Phe Tyr Arg
130                 135                 140

Cys Cys Asp Gln Leu Leu Lys Glu Asp Gly Leu Phe Val Leu Gln Phe
145                 150                 155                 160

Ile Ser Ile Pro Glu Glu Leu Ser Lys Glu Ile Gln Gln Thr Ala Gly
                165                 170                 175

Phe Leu Lys Glu Tyr Ile Phe Pro Gly Gly Thr Leu Leu Ser Leu Asp
            180                 185                 190

Arg Asn Xaa Ser Ala Met Ala Ala Thr Arg Phe Ser Val Glu His
        195                 200                 205

Val Glu Asn Ile Xaa Met Ser Tyr Tyr His Thr Leu Arg Trp Trp
210                 215                 220

<210> SEQ ID NO 9
<211> LENGTH: 123
<212> TYPE: PRT
<213> ORGANISM: Gossypium arboreum

<400> SEQUENCE: 9

Phe Leu Ser Val Tyr Ile Phe Pro Gly Gly Pro Leu Leu Ser Leu Asp
1               5                   10                  15
```

```
Arg His Leu Ser Ala Met Ala Ala Thr Arg Phe Ser Val Gln Gln
            20                  25                  30

Val Glu His Ile Gly Met Cys Tyr Tyr His Pro Leu Arg Trp Trp Arg
        35                  40                  45

Lys Leu Phe Leu Lys Thr Phe Pro Glu Asn Thr Ser Lys Val Leu Ala
    50                  55                  60

Leu Gly Phe Pro Gln Lys Phe Ile Arg Thr Trp Glu Tyr Tyr Phe Asp
65                  70                  75                  80

Tyr Cys Ala Ala Gly Phe Lys Thr Gly Thr Leu Ile Asp Ser Gln Val
                85                  90                  95

Val Phe Ser Arg Ala Gly Asn Phe Gly Thr Leu Gly Asp Pro Tyr Lys
            100                 105                 110

Gly Phe Pro Ser Ala Tyr Ser Phe Met Asp Asp
            115                 120
```

<210> SEQ ID NO 10
<211> LENGTH: 295
<212> TYPE: PRT
<213> ORGANISM: Gossypium arboreum

<400> SEQUENCE: 10

```
Phe Ile Ser Arg His Tyr Asp Leu Ser Asn Glu Leu Phe Ser Leu Tyr
1               5                   10                  15

Leu Gly Lys Met Met Gln Tyr Ser Ser Gly Val Phe Arg Thr Gly Glu
            20                  25                  30

Glu His Leu Asp Val Ala Gln Arg Arg Lys Ile Ser Ser Leu Ile Glu
        35                  40                  45

Lys Thr Arg Ile Glu Lys Trp His Glu Val Leu Asp Ile Gly Cys Gly
    50                  55                  60

Trp Gly Ser Leu Ala Ile Glu Thr Val Lys Arg Thr Gly Cys Lys Tyr
65                  70                  75                  80

Thr Gly Ile Thr Leu Ser Glu Gln Gln Leu Lys Tyr Ala Gln Glu Lys
                85                  90                  95

Val Lys Glu Ala Gly Leu Glu Asp Asn Ile Lys Ile Leu Leu Cys Asp
            100                 105                 110

Tyr Arg Gln Leu Pro Lys Glu His Gln Phe Asp Arg Ile Ile Ser Val
            115                 120                 125

Glu Met Val Glu His Val Gly Glu Glu Tyr Ile Glu Glu Phe Tyr Arg
130                 135                 140

Cys Cys Asp Gln Leu Leu Lys Glu Asp Gly Leu Phe Val Leu Gln Phe
145                 150                 155                 160

Ile Ser Ile Pro Glu Glu Leu Ser Lys Glu Ile Gln Gln Thr Ala Gly
                165                 170                 175

Phe Leu Lys Glu Tyr Ile Phe Pro Gly Gly Thr Leu Leu Ser Leu Asp
            180                 185                 190

Arg Asn Leu Ser Ala Met Ala Ala Thr Arg Phe Ser Val Glu Gln
            195                 200                 205

Val Glu His Ile Gly Met Cys Tyr Tyr His Pro Leu Arg Trp Trp Arg
210                 215                 220

Lys Leu Phe Leu Glu Asn Thr Ser Lys Val Leu Ala Leu Gly Phe Pro
225                 230                 235                 240

Gln Lys Phe Ile Arg Thr Trp Glu Tyr Tyr Phe Asp Tyr Cys Ala Ala
            245                 250                 255

Gly Phe Lys Thr Gly Thr Leu Ile Asp Ser Gln Val Val Phe Ser Arg
```

```
                  260                 265                 270
Ala Gly Asn Phe Gly Thr Leu Gly Asp Pro Tyr Lys Gly Phe Pro Ser
            275                 280                 285

Ala Tyr Ser Phe Met Asp Asp
            290             295

<210> SEQ ID NO 11
<211> LENGTH: 431
<212> TYPE: PRT
<213> ORGANISM: Sterculia cyclopropane fatty acid synthase

<400> SEQUENCE: 11

Met Gly Ser Ser His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Cys Ser Leu Lys Thr Ala Leu Lys Val His Asn Pro
        35                  40                  45

Gln Phe Tyr Trp Arg Ile Met Lys Glu Ala Asp Ile Gly Leu Ala Asp
    50                  55                  60

Ala Tyr Ile Gln Gly Asp Phe Ser Phe Val Asp Lys Asp Asp Gly Leu
65                  70                  75                  80

Leu Asn Leu Phe Arg Ile Leu Ile Ala Asn Lys Glu Leu Asn Ser Ala
                85                  90                  95

Ser Gly Gln Asn Lys Arg Arg Thr Trp Leu Ser Pro Ala Leu Phe Thr
            100                 105                 110

Ala Gly Ile Ser Ser Ala Lys Tyr Phe Leu Lys His Tyr Met Arg Gln
        115                 120                 125

Asn Thr Val Thr Gln Ala Arg Arg Asn Ile Ser Arg His Tyr Asp Leu
    130                 135                 140

Ser Asn Glu Leu Phe Thr Leu Tyr Leu Gly Glu Met Met Gln Tyr Ser
145                 150                 155                 160

Ser Gly Ile Phe Lys Thr Gly Glu Glu His Leu Asp Val Ala Gln Arg
                165                 170                 175

Arg Lys Ile Ser Ser Leu Ile Asp Lys Ser Arg Ile Glu Lys Trp His
            180                 185                 190

Glu Val Leu Asp Ile Gly Cys Gly Trp Gly Ser Leu Ala Met Glu Val
        195                 200                 205

Val Lys Arg Thr Gly Cys Lys Tyr Thr Gly Ile Thr Leu Ser Glu Gln
    210                 215                 220

Gln Leu Lys Tyr Ala Glu Glu Lys Val Lys Glu Ala Gly Leu Gln Gly
225                 230                 235                 240

Asn Ile Lys Phe Leu Leu Cys Asp Tyr Arg Gln Leu Pro Lys Thr Phe
                245                 250                 255

Lys Tyr Asp Arg Ile Ile Ser Val Glu Met Val Glu His Val Gly Glu
            260                 265                 270

Glu Tyr Ile Glu Glu Phe Phe Arg Cys Cys Asp Ser Leu Leu Ala Glu
        275                 280                 285

Asn Gly Leu Phe Val Leu Gln Phe Ile Ser Ile Pro Glu Ile Leu Ser
    290                 295                 300

Lys Glu Ile Gln Gln Thr Ala Gly Phe Leu Lys Glu Tyr Ile Phe Pro
305                 310                 315                 320

Gly Gly Thr Leu Leu Ser Leu Asp Arg Thr Leu Ser Ala Met Ala Ala
                325                 330                 335
```

```
Ala Ser Arg Phe Ser Val Glu His Val Glu Asn Ile Gly Ile Ser Tyr
                340                 345                 350

Tyr His Thr Leu Arg Trp Trp Arg Lys Asn Phe Leu Ala Asn Glu Ser
            355                 360                 365

Lys Val Leu Ala Leu Gly Phe Asp Glu Lys Phe Met Arg Thr Trp Glu
        370                 375                 380

Tyr Tyr Phe Asp Tyr Cys Ala Ala Gly Phe Lys Thr Gly Thr Leu Ile
385                 390                 395                 400

Asp Tyr Gln Val Val Phe Ser Arg Ala Gly Asn Phe Ala Ala Leu Gly
                405                 410                 415

Asp Pro Tyr Ile Gly Phe Pro Ser Ala Tyr Ser Tyr Ser Asp Asn
                420                 425                 430

<210> SEQ ID NO 12
<211> LENGTH: 289
<212> TYPE: PRT
<213> ORGANISM: Escherichia coli

<400> SEQUENCE: 12

Asp Thr Leu Arg Ile Ala Gly Ala Arg Leu Phe Asn Leu Gln Ser Lys
1               5                   10                  15

Lys Arg Ala Trp Ile Val Gly Lys Glu His Tyr Asp Leu Gly Asn Asp
                20                  25                  30

Leu Phe Ser Arg Met Leu Asp Pro Phe Met Gln Tyr Ser Cys Ala Tyr
            35                  40                  45

Trp Lys Asp Ala Asp Asn Leu Glu Ser Ala Gln Ala Lys Leu Lys
        50                  55                  60

Met Ile Cys Glu Lys Leu Gln Leu Lys Pro Gly Met Arg Val Leu Asp
65                  70                  75                  80

Ile Gly Cys Gly Trp Gly Gly Leu Ala His Tyr Met Ala Ser Asn Tyr
                85                  90                  95

Asp Val Ser Val Val Gly Val Thr Ile Ser Ala Glu Gln Gln Lys Met
                100                 105                 110

Ala Gln Glu Arg Cys Glu Gly Leu Asp Val Thr Ile Leu Leu Gln Asp
            115                 120                 125

Tyr Arg Asp Leu Asn Asp Gln Phe Asp Arg Ile Val Ser Val Gly Met
        130                 135                 140

Phe Glu His Val Gly Pro Lys Asn Tyr Asp Thr Tyr Phe Ala Val Val
145                 150                 155                 160

Asp Arg Asn Leu Lys Pro Glu Gly Ile Phe Leu Leu His Thr Ile Gly
                165                 170                 175

Ser Lys Lys Thr Asp Leu Asn Val Asp Pro Trp Ile Asn Lys Tyr Ile
                180                 185                 190

Phe Pro Asn Gly Cys Leu Pro Ser Val Arg Gln Ile Ala Gln Ser Ser
            195                 200                 205

Glu Pro His Phe Val Met Glu Asp Trp His Asn Phe Gly Ala Asp Tyr
        210                 215                 220

Asp Thr Thr Leu Met Ala Trp Tyr Glu Arg Phe Leu Ala Ala Trp Pro
225                 230                 235                 240

Glu Ile Ala Asp Asn Tyr Ser Glu Arg Phe Lys Arg Met Phe Thr Tyr
                245                 250                 255

Tyr Leu Asn Ala Cys Ala Gly Ala Phe Arg Ala Arg Asp Ile Gln Leu
                260                 265                 270

Trp Gln Val Val Phe Ser Arg Gly Val Glu Asn Gly Leu Arg Val Ala
            275                 280                 285
```

Arg

<210> SEQ ID NO 13
<211> LENGTH: 287
<212> TYPE: PRT
<213> ORGANISM: Cyclopropane synthase

<400> SEQUENCE: 13

```
Met Pro Asp Glu Leu Lys Pro His Phe Ala Asn Val Gln Ala His Tyr
1               5                   10                  15
Asp Leu Ser Asp Asp Phe Phe Arg Leu Phe Leu Asp Pro Thr Gln Thr
            20                  25                  30
Tyr Ser Cys Ala Tyr Phe Glu Arg Asp Asp Met Thr Leu Gln Glu Ala
        35                  40                  45
Gln Ile Ala Lys Ile Asp Leu Ala Leu Gly Lys Leu Gly Leu Gln Pro
    50                  55                  60
Gly Met Thr Leu Leu Asp Val Gly Cys Gly Trp Gly Ala Thr Met Met
65                  70                  75                  80
Arg Ala Val Glu Lys Tyr Asp Val Asn Val Val Gly Leu Thr Leu Ser
                85                  90                  95
Lys Asn Gln Ala Asn His Val Gln Gln Leu Val Ala Asn Ser Glu Asn
            100                 105                 110
Leu Arg Ser Lys Arg Val Leu Leu Ala Gly Trp Gln Phe Asp Glu
        115                 120                 125
Pro Val Asp Arg Ile Val Ser Ile Gly Ala Phe Glu His Phe Gly His
    130                 135                 140
Glu Arg Tyr Asp Ala Phe Phe Ser Leu Ala His Arg Leu Leu Pro Ala
145                 150                 155                 160
Asp Gly Val Met Leu Leu His Thr Ile Thr Gly Leu His Pro Lys Glu
                165                 170                 175
Ile His Glu Arg Gly Leu Pro Met Ser Phe Thr Phe Ala Arg Phe Leu
            180                 185                 190
Lys Phe Ile Val Thr Glu Ile Phe Pro Gly Gly Arg Leu Pro Ser Ile
        195                 200                 205
Pro Met Val Gln Glu Cys Ala Ser Ala Asn Gly Phe Thr Val Thr Arg
    210                 215                 220
Val Gln Ser Leu Gln Pro His Tyr Ala Lys Thr Leu Asp Leu Trp Ser
225                 230                 235                 240
Ala Ala Leu Gln Ala Asn Lys Gly Gln Ala Ile Ala Leu Gln Ser Glu
                245                 250                 255
Glu Val Tyr Glu Arg Tyr Met Lys Tyr Leu Thr Gly Cys Ala Glu Met
            260                 265                 270
Phe Arg Ile Gly Tyr Ile Asp Val Asn Gln Phe Thr Cys Gln Lys
        275                 280                 285
```

<210> SEQ ID NO 14
<211> LENGTH: 302
<212> TYPE: PRT
<213> ORGANISM: Cyclopropane synthase

<400> SEQUENCE: 14

```
Met Thr Ser Gln Gly Asp Thr Thr Ser Gly Thr Gln Leu Lys Pro Pro
1               5                   10                  15
Val Glu Ala Val Arg Ser His Tyr Asp Lys Ser Asn Glu Phe Phe Lys
            20                  25                  30
```

Leu Trp Leu Asp Pro Ser Met Thr Tyr Ser Cys Ala Tyr Phe Glu Arg
         35                  40                  45

Pro Asp Met Thr Leu Glu Glu Ala Gln Tyr Ala Lys Arg Lys Leu Ala
 50                  55                  60

Leu Asp Lys Leu Asn Leu Glu Pro Gly Met Thr Leu Leu Asp Ile Gly
 65                  70                  75                  80

Cys Gly Trp Gly Ser Thr Met Arg His Ala Val Ala Glu Tyr Asp Val
                 85                  90                  95

Asn Val Ile Gly Leu Thr Leu Ser Glu Asn Gln Tyr Ala His Asp Lys
             100                 105                 110

Ala Met Phe Asp Glu Val Asp Ser Pro Arg Arg Lys Glu Val Arg Ile
         115                 120                 125

Gln Gly Trp Glu Glu Phe Asp Glu Pro Val Arg Ile Val Ser Leu
         130                 135                 140

Gly Ala Phe Glu His Phe Ala Asp Gly Ala Gly Asp Ala Gly Phe Glu
145                 150                 155                 160

Arg Tyr Asp Thr Phe Phe Lys Lys Phe Tyr Asn Leu Thr Pro Asp Asp
                 165                 170                 175

Gly Arg Met Leu Leu His Thr Ile Thr Ile Pro Asp Lys Glu Glu Ala
             180                 185                 190

Gln Glu Leu Gly Leu Thr Ser Pro Met Ser Leu Leu Arg Phe Ile Lys
         195                 200                 205

Phe Ile Leu Thr Glu Ile Phe Pro Gly Gly Arg Leu Pro Arg Ile Ser
         210                 215                 220

Gln Val Asp Tyr Tyr Ser Ser Asn Ala Gly Trp Lys Val Glu Arg Tyr
225                 230                 235                 240

His Arg Ile Gly Ala Asn Tyr Val Pro Thr Leu Asn Ala Trp Ala Asp
                 245                 250                 255

Ala Leu Gln Ala His Lys Asp Glu Ala Ile Ala Leu Lys Gly Gln Glu
             260                 265                 270

Thr Tyr Asp Ile Tyr Met His Tyr Leu Arg Gly Cys Ser Asp Leu Phe
         275                 280                 285

Arg Asp Lys Tyr Thr Asp Val Cys Gln Phe Thr Leu Val Lys
         290                 295                 300

<210> SEQ ID NO 15
<211> LENGTH: 286
<212> TYPE: PRT
<213> ORGANISM: Cyclopropane synthase

<400> SEQUENCE: 15

Met Ala Lys Leu Arg Pro Tyr Tyr Glu Glu Ser Gln Ser Ala Tyr Asp
1                5                  10                  15

Ile Ser Asp Asp Phe Phe Ala Leu Phe Leu Asp Pro Thr Trp Val Tyr
             20                  25                  30

Thr Cys Ala Tyr Phe Glu Arg Asp Asp Met Thr Leu Glu Glu Ala Gln
         35                  40                  45

Leu Ala Lys Val Asp Leu Ala Leu Asp Lys Leu Asn Leu Glu Pro Gly
 50                  55                  60

Met Thr Leu Leu Asp Val Gly Cys Gly Trp Gly Gly Ala Leu Val Arg
 65                  70                  75                  80

Ala Val Glu Lys Tyr Asp Val Asn Val Ile Gly Leu Thr Leu Ser Arg
                 85                  90                  95

Asn His Tyr Glu Arg Ser Lys Asp Arg Leu Ala Ala Ile Gly Thr Gln
             100                 105                 110

```
Arg Arg Ala Glu Ala Arg Leu Gln Gly Trp Glu Glu Phe Glu Glu Asn
            115                 120                 125

Val Asp Arg Ile Val Ser Phe Glu Ala Phe Asp Ala Phe Lys Lys Glu
    130                 135                 140

Arg Tyr Leu Thr Phe Phe Glu Arg Ser Tyr Asp Ile Leu Pro Asp Asp
145                 150                 155                 160

Gly Arg Met Leu Leu His Ser Leu Phe Thr Tyr Asp Arg Arg Trp Leu
                165                 170                 175

His Glu Gln Gly Ile Ala Leu Thr Met Ser Asp Leu Arg Phe Leu Lys
            180                 185                 190

Phe Leu Arg Glu Ser Ile Phe Pro Gly Gly Glu Leu Pro Ser Glu Pro
            195                 200                 205

Asp Ile Val Asp Asn Ala Gln Ala Ala Gly Phe Thr Ile Glu His Val
            210                 215                 220

Gln Leu Leu Gln Gln His Tyr Ala Arg Thr Leu Asp Ala Trp Ala Ala
225                 230                 235                 240

Asn Leu Gln Ala Ala Arg Glu Arg Ala Ile Ala Val Gln Ser Glu Glu
            245                 250                 255

Val Tyr Asn Asn Phe Met His Tyr Leu Thr Gly Cys Ala Glu Arg Phe
            260                 265                 270

Arg Arg Gly Leu Ile Asn Val Ala Gln Phe Thr Met Thr Lys
            275                 280                 285

<210> SEQ ID NO 16
<211> LENGTH: 287
<212> TYPE: PRT
<213> ORGANISM: Cyclopropane synthase

<400> SEQUENCE: 16

Met Val Asn Asp Leu Thr Pro His Phe Glu Asp Val Gln Ala His Tyr
1               5                   10                  15

Asp Leu Ser Asp Asp Phe Phe Arg Leu Phe Leu Asp Pro Thr Gln Thr
            20                  25                  30

Tyr Ser Cys Ala His Phe Glu Arg Glu Asp Met Thr Leu Glu Glu Ala
            35                  40                  45

Gln Ile Ala Lys Ile Asp Leu Ala Leu Gly Lys Leu Gly Leu Gln Pro
    50                  55                  60

Gly Met Thr Leu Leu Asp Ile Gly Cys Gly Trp Gly Ala Thr Met Arg
65                  70                  75                  80

Arg Ala Ile Ala Gln Tyr Asp Val Asn Val Val Gly Leu Thr Leu Ser
            85                  90                  95

Lys Asn Gln Ala Ala His Val Gln Lys Ser Phe Asp Glu Met Asp Thr
            100                 105                 110

Pro Arg Asp Arg Arg Val Leu Leu Ala Gly Trp Glu Gln Phe Asn Glu
            115                 120                 125

Pro Val Asp Arg Ile Val Ser Ile Gly Ala Phe Glu His Phe Gly His
            130                 135                 140

Asp Arg His Ala Asp Phe Phe Ala Arg Ala His Lys Ile Leu Pro Pro
145                 150                 155                 160

Asp Gly Val Leu Leu Leu His Thr Ile Thr Gly Leu Thr Arg Gln Gln
                165                 170                 175

Met Val Asp His Gly Leu Pro Leu Thr Leu Trp Leu Ala Arg Phe Leu
            180                 185                 190

Lys Phe Ile Ala Thr Glu Ile Phe Pro Gly Gly Gln Pro Pro Thr Ile
```

```
                195                 200                 205
Glu Met Val Glu Glu Gln Ser Ala Lys Thr Gly Phe Thr Leu Thr Arg
    210                 215                 220

Arg Gln Ser Leu Gln Pro His Tyr Ala Arg Thr Leu Asp Leu Trp Ala
225                 230                 235                 240

Glu Ala Leu Gln Glu His Lys Ser Glu Ala Ile Ala Ile Gln Ser Glu
                245                 250                 255

Glu Val Tyr Glu Arg Tyr Met Lys Tyr Leu Thr Gly Cys Ala Lys Leu
            260                 265                 270

Phe Arg Val Gly Tyr Ile Asp Val Asn Gln Phe Thr Leu Ala Lys
            275                 280                 285

<210> SEQ ID NO 17
<211> LENGTH: 293
<212> TYPE: PRT
<213> ORGANISM: Cyclopropane synthase

<400> SEQUENCE: 17

Met Ser Asp Asn Ser Thr Gly Thr Thr Lys Ser Arg Ser Asn Val Asp
1               5                   10                  15

Asp Val Gln Ala His Tyr Asp Leu Ser Asp Ala Phe Phe Ala Leu Phe
            20                  25                  30

Gln Asp Pro Thr Arg Thr Tyr Ser Cys Ala Tyr Phe Glu Arg Asp Asp
        35                  40                  45

Met Thr Leu His Glu Ala Gln Val Ala Lys Leu Asp Leu Thr Leu Gly
    50                  55                  60

Lys Leu Gly Leu Glu Pro Gly Met Thr Leu Leu Asp Val Gly Cys Gly
65                  70                  75                  80

Trp Gly Ser Val Met Lys Arg Ala Val Glu Arg Tyr Asp Val Asn Val
                85                  90                  95

Val Gly Leu Thr Leu Ser Lys Asn Gln His Ala Tyr Cys Gln Gln Val
            100                 105                 110

Leu Asp Lys Val Asp Thr Asn Arg Ser His Arg Val Leu Leu Ser Asp
        115                 120                 125

Trp Ala Asn Phe Ser Glu Pro Val Asp Arg Ile Val Thr Ile Glu Ala
    130                 135                 140

Ile Glu His Phe Gly Phe Glu Arg Tyr Asp Asp Phe Lys Phe Ala
145                 150                 155                 160

Tyr Asn Ala Met Pro Ala Asp Gly Val Met Leu Leu His Ser Ile Thr
                165                 170                 175

Gly Leu His Val Lys Gln Val Ile Glu Arg Gly Ile Pro Leu Thr Met
            180                 185                 190

Glu Met Ala Lys Phe Ile Arg Phe Ile Val Thr Asp Ile Phe Pro Gly
        195                 200                 205

Gly Arg Leu Pro Thr Ile Glu Thr Ile Glu Glu His Val Thr Lys Ala
    210                 215                 220

Gly Phe Thr Ile Thr Asp Ile Gln Ser Leu Gln Pro His Phe Ala Arg
225                 230                 235                 240

Thr Leu Asp Leu Trp Ala Glu Ala Leu Gln Ala His Lys Asp Glu Ala
                245                 250                 255

Ile Glu Ile Gln Ser Ala Glu Val Tyr Glu Arg Tyr Met Lys Tyr Leu
            260                 265                 270

Thr Gly Cys Ala Lys Ala Phe Arg Met Gly Tyr Ile Asp Cys Asn Gln
        275                 280                 285
```

```
Phe Thr Leu Ala Lys
    290
```

<210> SEQ ID NO 18
<211> LENGTH: 301
<212> TYPE: PRT
<213> ORGANISM: Cyclopropane synthase

<400> SEQUENCE: 18

```
Met Thr Arg Met Ala Glu Lys Pro Ile Ser Pro Thr Lys Thr Arg Thr
1               5                   10                  15

Arg Phe Glu Asp Ile Gln Ala His Tyr Asp Val Ser Asp Asp Phe Phe
            20                  25                  30

Ala Leu Phe Gln Asp Pro Thr Arg Thr Tyr Ser Cys Ala Tyr Phe Glu
        35                  40                  45

Pro Pro Glu Leu Thr Leu Glu Glu Ala Gln Tyr Ala Lys Val Asp Leu
    50                  55                  60

Asn Leu Asp Lys Leu Asp Leu Lys Pro Gly Met Thr Leu Leu Asp Ile
65                  70                  75                  80

Gly Cys Gly Trp Gly Thr Thr Met Arg Arg Ala Val Glu Arg Phe Asp
                85                  90                  95

Val Asn Val Ile Gly Leu Thr Leu Ser Lys Asn Gln His Ala Arg Cys
            100                 105                 110

Glu Gln Val Leu Ala Ser Ile Asp Thr Asn Arg Ser Arg Gln Val Leu
        115                 120                 125

Leu Gln Gly Trp Glu Asp Phe Ala Glu Pro Val Asp Arg Ile Val Ser
    130                 135                 140

Ile Glu Ala Phe Glu His Phe Gly His Glu Asn Tyr Asp Asp Phe Phe
145                 150                 155                 160

Lys Arg Cys Phe Asn Ile Met Pro Ala Asp Gly Arg Met Thr Val Gln
                165                 170                 175

Ser Ser Val Ser Tyr His Pro Tyr Glu Met Ala Ala Arg Gly Lys Lys
            180                 185                 190

Leu Ser Phe Glu Thr Ala Arg Phe Ile Lys Phe Ile Val Thr Glu Ile
        195                 200                 205

Phe Pro Gly Gly Arg Leu Pro Ser Thr Glu Met Met Val Glu His Gly
    210                 215                 220

Glu Lys Ala Gly Phe Thr Val Pro Glu Pro Leu Ser Leu Arg Pro His
225                 230                 235                 240

Tyr Ile Lys Thr Leu Arg Ile Trp Gly Asp Thr Leu Gln Ser Asn Lys
                245                 250                 255

Asp Lys Ala Ile Glu Val Thr Ser Glu Val Tyr Asn Arg Tyr Met
            260                 265                 270

Lys Tyr Leu Arg Gly Cys Glu His Tyr Phe Thr Asp Glu Met Leu Asp
        275                 280                 285

Cys Ser Leu Val Thr Tyr Leu Lys Pro Gly Ala Ala Ala
    290                 295                 300
```

<210> SEQ ID NO 19
<211> LENGTH: 382
<212> TYPE: PRT
<213> ORGANISM: Bacterial cyclopropane fatty acid synthase

<400> SEQUENCE: 19

```
Met Ser Ser Ser Cys Ile Glu Glu Val Ser Val Pro Asp Asp Asn Trp
1               5                   10                  15
```

```
Tyr Arg Ile Ala Asn Glu Leu Leu Ser Arg Ala Gly Ile Ala Ile Asn
         20                  25                  30
Gly Ser Ala Pro Ala Asp Ile Arg Val Lys Asn Pro Asp Phe Phe Lys
             35                  40                  45
Arg Val Leu Gln Glu Gly Ser Leu Gly Leu Gly Glu Ser Tyr Met Asp
 50                  55                  60
Gly Trp Glu Cys Asp Arg Leu Asp Met Phe Phe Ser Lys Val Leu
 65                  70                  75                  80
Arg Ala Gly Leu Glu Asn Gln Leu Pro His His Phe Lys Asp Thr Leu
                 85                  90                  95
Arg Ile Ala Gly Ala Arg Leu Phe Asn Leu Gln Ser Lys Lys Arg Ala
                100                 105                 110
Trp Ile Val Gly Lys Glu His Tyr Asp Leu Gly Asn Asp Leu Phe Ser
            115                 120                 125
Arg Met Leu Asp Pro Phe Met Gln Tyr Ser Cys Ala Tyr Trp Lys Asp
130                 135                 140
Ala Asp Asn Leu Glu Ser Ala Gln Gln Ala Lys Leu Lys Met Ile Cys
145                 150                 155                 160
Glu Lys Leu Gln Leu Lys Pro Gly Met Arg Val Leu Asp Ile Gly Cys
                165                 170                 175
Gly Trp Gly Gly Leu Ala His Tyr Met Ala Ser Asn Tyr Asp Val Ser
            180                 185                 190
Val Val Gly Val Thr Ile Ser Ala Glu Gln Gln Lys Met Ala Gln Glu
        195                 200                 205
Arg Cys Glu Gly Leu Asp Val Thr Ile Leu Leu Gln Asp Tyr Arg Asp
    210                 215                 220
Leu Asn Asp Gln Phe Asp Arg Ile Val Ser Val Gly Met Phe Glu His
225                 230                 235                 240
Val Gly Pro Lys Asn Tyr Asp Thr Tyr Phe Ala Val Val Asp Arg Asn
                245                 250                 255
Leu Lys Pro Glu Gly Ile Phe Leu Leu His Thr Ile Gly Ser Lys Lys
            260                 265                 270
Thr Asp Leu Asn Val Asp Pro Trp Ile Asn Lys Tyr Ile Phe Pro Asn
        275                 280                 285
Gly Cys Leu Pro Ser Val Arg Gln Ile Ala Gln Ser Ser Glu Pro His
    290                 295                 300
Phe Val Met Glu Asp Trp His Asn Phe Gly Ala Asp Tyr Asp Thr Thr
305                 310                 315                 320
Leu Met Ala Trp Tyr Glu Arg Phe Leu Ala Ala Trp Pro Glu Ile Ala
                325                 330                 335
Asp Asn Tyr Ser Glu Arg Phe Lys Arg Met Phe Thr Tyr Tyr Leu Asn
            340                 345                 350
Ala Cys Ala Gly Ala Phe Arg Ala Arg Asp Ile Gln Leu Trp Gln Val
        355                 360                 365
Val Phe Ser Arg Gly Val Glu Asn Gly Leu Arg Val Ala Arg
    370                 375                 380

<210> SEQ ID NO 20
<211> LENGTH: 324
<212> TYPE: PRT
<213> ORGANISM: Sterculia cyclopropane fatty acid synthase

<400> SEQUENCE: 20

Pro Ala Leu Phe Thr Ala Gly Ile Ser Ser Ala Lys Tyr Phe Leu Lys
1                5                  10                  15
```

His Tyr Met Arg Gln Asn Thr Val Thr Gln Ala Arg Arg Asn Ile Ser
                20                  25                  30

Arg His Tyr Asp Leu Ser Asn Glu Leu Phe Thr Leu Tyr Leu Gly Glu
            35                  40                  45

Met Met Gln Tyr Ser Ser Gly Ile Phe Lys Thr Gly Glu Glu His Leu
        50                  55                  60

Asp Val Ala Gln Arg Arg Lys Ile Ser Leu Ile Asp Lys Ser Arg
65                  70                  75                  80

Ile Glu Lys Trp His Glu Val Leu Asp Ile Gly Cys Gly Trp Gly Ser
                85                  90                  95

Leu Ala Met Glu Val Val Lys Arg Thr Gly Cys Lys Tyr Thr Gly Ile
            100                 105                 110

Thr Leu Ser Glu Gln Gln Leu Lys Tyr Ala Glu Glu Lys Val Lys Glu
        115                 120                 125

Ala Gly Leu Gln Gly Asn Ile Lys Phe Leu Leu Cys Asp Tyr Arg Gln
    130                 135                 140

Leu Pro Lys Thr Phe Lys Tyr Asp Arg Ile Ile Ser Val Glu Met Val
145                 150                 155                 160

Asp Met Val Gly Glu Glu Tyr Ile Glu Glu Phe Arg Cys Cys Asp
                165                 170                 175

Ser Leu Leu Ala Glu Asn Gly Leu Phe Val Leu Gln Phe Ile Ser Ile
            180                 185                 190

Pro Glu Ile Leu Ser Lys Glu Ile Gln Gln Thr Ala Gly Phe Leu Lys
        195                 200                 205

Glu Tyr Ile Phe Pro Gly Gly Thr Leu Leu Ser Leu Asp Arg Thr Leu
    210                 215                 220

Ser Ala Met Ala Ala Ala Ser Arg Phe Ser Val Glu His Val Glu Asn
225                 230                 235                 240

Ile Gly Ile Ser Tyr Tyr His Thr Leu Arg Trp Trp Arg Lys Asn Phe
                245                 250                 255

Leu Ala Asn Glu Ser Lys Val Leu Ala Leu Gly Phe Asp Glu Lys Phe
            260                 265                 270

Met Arg Thr Trp Glu Tyr Tyr Phe Asp Tyr Cys Ala Ala Gly Phe Lys
        275                 280                 285

Thr Gly Thr Leu Ile Asp Tyr Gln Val Val Phe Ser Arg Ala Gly Asn
    290                 295                 300

Phe Ala Ala Leu Gly Asp Pro Tyr Ile Gly Phe Pro Ser Ala Tyr Ser
305                 310                 315                 320

Tyr Ser Asp Asn

<210> SEQ ID NO 21
<211> LENGTH: 37
<212> TYPE: DNA
<213> ORGANISM: Artificial Sequence
<220> FEATURE:
<223> OTHER INFORMATION: Synthetic

<400> SEQUENCE: 21
ccggaattct gttctcttaa aacagctctg aaagtgc                        37

<210> SEQ ID NO 22
<211> LENGTH: 42
<212> TYPE: DNA
<213> ORGANISM: Artificial Sequence
<220> FEATURE:
<223> OTHER INFORMATION: Synthetic

<400> SEQUENCE: 22

```
gcctattaac tttatcaaaa gtaaataggc tcgagatctc cc                42
```

<210> SEQ ID NO 23
<211> LENGTH: 1320
<212> TYPE: DNA
<213> ORGANISM: Sterculia cyclopropane fatty acid synthase

<400> SEQUENCE: 23

```
atgggcagca gccatcatca tcatcatcac agcagcggcc tggtgccgcg cggcagccat    60
atggctagca tgactggtgg acagcaaatg gtcgcggat  ccgaattctg ttctcttaaa   120
acagctctga aagtgcataa tcctcagttt tactggagga ttatgaaaga agctgatata   180
ggccttgctg atgcatatat ccaaggagat ttttcttttg ttgacaagga tgatggtctt   240
cttaatcttt tccggatact tattgccaat aaagagttga actctgcctc aggacagaac   300
aaaagaagga cttggctgtc acctgcactg ttcacagctg gtatatcatc tgcaaagtat   360
ttcttgaagc attacatgag gcaaaatact gttacacagg ctcgcaggaa catttctcgt   420
cattatgacc tgagtaatga acttttcact ctatacttag gtgaaatgat gcaatactct   480
tctggaattt ttaagacggg agaagaacat ttggacgttg cacagcgcag aaaaatcagt   540
tccttaattg ataaatcaag aatagagaag tggcatgaag ttcttgacat tggatgtggt   600
tggggaagct agctatgga agttgtcaaa agaacaggat gtaaatacac tggcatcaca   660
cttttcagag cagcaactga aatatgcaga gaaaaagtaa aggaagctgg acttcaggga   720
aacatcaaat tcttctctg tgactatcgc cagttaccca agacattcaa atatgacaga   780
atcatatctg ttgagatggt tgaacatgtt ggtgaagaat atattgagga gttttcaga   840
tgctgtgact cattattggc agagaatggg cttttcgttc ttcagttcat atcaattcca   900
gagatacttt ccaaagaaat ccagcaaaca gctggttttc taaggaata tatcttccct   960
ggtggaaccc tgctttctct ggataggact tgtcagcca tggctgctgc atcaagattt  1020
agtgtggagc atgtggaaaa tataggaatt agttattatc acacactgag atggtggagg  1080
aaaaatttct tggcaaatga agcaaagtt  ctggctttgg ggttcgatga aagttcatg   1140
cggacatggg agtattattt tgattactgc gcagctggtt taagacagg gacacttata   1200
gattaccagg ttgtattctc acgggctggc aatttcgctg cacttggcga tccatacata  1260
ggtttccctt cagcatattc ctactcggat aattgaaata gttttcattt atccgagctc  1320
```

<210> SEQ ID NO 24
<211> LENGTH: 1144
<212> TYPE: DNA
<213> ORGANISM: Gossypium arboreum

<400> SEQUENCE: 24

```
gttcatttct cgtcattatg atctgagtaa tgaacttttc tctctatact tgggcaaaat    60
gatgcaatac tcttctggag tctttaggac aggagaagaa catttggacg ttgcacagcg   120
aagaaaaatc agttctctaa ttgagaaaac aaggatagag aaatggcatg aagttctcga   180
cattgggtgc ggttgggga  gcttagctat tgaaactgtg aaaagaacag gatgcaaata   240
tactggcatc actctatcag aacagcaact gaaatatgct caagaaaaag tgaaggaagc   300
tggactcgag gataacatca aaatacttct ctagtgmctm ycgccmstya ccccctmagga   360
acaccmmytt sacmgmmyca tcatckgtms asmysstagm acmtgttsst gamsmataym   420
```

```
ctctgagsaa tttymcmsmc tscctgtsmy cmmycccctm cctgammswa satgsmcttt      480
tcsttcttac mgttcayayc aatcccmswg gagcttccm wagmaatccc tagcaamcmg       540
ctggttttct taagcgwata yatatttccc tggtggamcc ctgctttctt tggataggma     600
tttatcagcc atggctgctg cmacaagatt cagtgtgsag casgtggaam acataggaat     660
gwgttattac cacmcactga gatggtggag aaaactttc ctgaaaacac aagcaaagtt      720
ctggctttgg ggttccccca gaagttcatc cggacatggg aatactattt cgattactgt    780
gctgctggtt ttaagacagg aacccttata gattcccagg ttgtattttc tcgagccggt    840
aatttcggta cacttggaga tccatacaaa ggtttcccTT ctgcatattc cttcatggat    900
gattgaacaa agtgtttgaa tatatgatcc ccataccatg attcacccag ctggatccaa    960
ctggtaccag tgtttccca gtcccctgct tttgtttagt tatggttttc gtttcgttcc    1020 gaaaagaaa taagccaata atgtatgtta ataatgaaat gtttgtatct ggtatatcta    1080
tactggttgg attttatgta tggagatgct gtttgctttt tgaagaagaa accccaccac  1140
cccc                                                                1144
```

```
<210> SEQ ID NO 25
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 25

Gly Xaa Gly Xaa Xaa Gly Xaa Xaa Xaa Ala
1               5                   10

<210> SEQ ID NO 26
<211> LENGTH: 9
<212> TYPE: PRT
<213> ORGANISM: Sterculia cyclopropane fatty acid synthase

<400> SEQUENCE: 26

Val Leu Asp Ile Gly Cys Gly Trp Gly
1               5

<210> SEQ ID NO 27
<211> LENGTH: 51
<212> TYPE: DNA
<213> ORGANISM: Artificial Sequence
<220> FEATURE:
<223> OTHER INFORMATION: Synthetic

<400> SEQUENCE: 27
tcctctagac tcgagcccgg gatgggagtg gctgtgatcg gtggtgggat c              51

<210> SEQ ID NO 28
<211> LENGTH: 36
<212> TYPE: DNA
<213> ORGANISM: Artificial Sequence
```

```
<220> FEATURE:
<223> OTHER INFORMATION: Synthetic

<400> SEQUENCE: 28
gttgtaagac gtcgtgtaac tcggtcatac aattcg                              36

<210> SEQ ID NO 29
<211> LENGTH: 36
<212> TYPE: DNA
<213> ORGANISM: Artificial Sequence
<220> FEATURE:
<223> OTHER INFORMATION: Synthetic

<400> SEQUENCE: 29
caatgtgctg cagaatgttg ggaaaacaag tcagcc                              36

<210> SEQ ID NO 30
<211> LENGTH: 42
<212> TYPE: DNA
<213> ORGANISM: Artificial Sequence
<220> FEATURE:
<223> OTHER INFORMATION: Synthetic

<400> SEQUENCE: 30
gggagatctc gagcctattt acttttgata aagttaatag gc                       42

<210> SEQ ID NO 31
<211> LENGTH: 58
<212> TYPE: DNA
<213> ORGANISM: Artificial Sequence
<220> FEATURE:
<223> OTHER INFORMATION: Synthetic

<400> SEQUENCE: 31
gccctcgaga attctaaaat gtctgtggct gtgatcggtg gtgggatcca agggctgg      58

<210> SEQ ID NO 32
<211> LENGTH: 37
<212> TYPE: DNA
<213> ORGANISM: Artificial Sequence
<220> FEATURE:
<223> OTHER INFORMATION: Synthetic

<400> SEQUENCE: 32
ccggaattct gttctcttaa aacagctctg aaagtgc                             37

<210> SEQ ID NO 33
<211> LENGTH: 42
<212> TYPE: DNA
<213> ORGANISM: Artificial Sequence
<220> FEATURE:
<223> OTHER INFORMATION: Synthetic

<400> SEQUENCE: 33
ccctctagag ctcggataaa tgaaaactat ttcaattatc cg                       42

<210> SEQ ID NO 34
<211> LENGTH: 215
<212> TYPE: PRT
<213> ORGANISM: Artificial Sequence
<220> FEATURE:
<223> OTHER INFORMATION: Synthetic

<400> SEQUENCE: 34

Phe Leu Leu Thr Val His Thr Asn Pro Pro Gly Ala Phe Pro Ser Asn
1               5                   10                  15
```

```
Pro Gln Pro Ala Gly Phe Leu Lys Arg Ile His Ile Pro Trp Trp Thr
            20                  25                  30

Pro Ala Phe Phe Gly Ala Phe Ile Ser His Gly Cys Cys His Lys Ile
            35                  40                  45

Gln Cys Ala Ala Gly Gly Thr His Arg Asn Val Leu Leu Pro Pro Thr
 50                  55                  60

Glu Met Val Glu Lys Thr Phe Pro Glu Asn Thr Ser Lys Val Leu Ala
 65                  70                  75                  80

Leu Gly Phe Pro Gln Lys Phe Ile Arg Thr Trp Glu Tyr Tyr Phe Asp
                85                  90                  95

Tyr Cys Ala Ala Gly Phe Lys Thr Gly Thr Leu Ile Asp Ser Gln Val
            100                 105                 110

Val Phe Ser Arg Ala Gly Asn Phe Gly Thr Leu Gly Asp Pro Tyr Lys
            115                 120                 125

Gly Phe Pro Ser Ala Tyr Ser Phe Met Asp Asp Thr Lys Cys Leu Asn
            130                 135                 140

Ile Ser Pro Tyr His Asp Ser Pro Ser Trp Ile Gln Leu Val Pro Val
145                 150                 155                 160

Phe Pro Gln Ser Pro Ala Phe Val Leu Trp Phe Ser Phe Arg Ser Glu
                165                 170                 175

Lys Glu Ile Ser Gln Cys Met Leu Ile Met Lys Cys Leu Tyr Leu Val
            180                 185                 190

Tyr Leu Tyr Trp Leu Asp Phe Met Tyr Gly Asp Ala Val Cys Phe Leu
            195                 200                 205

Lys Lys Lys Pro His His Pro
            210                 215

<210> SEQ ID NO 35
<211> LENGTH: 214
<212> TYPE: PRT
<213> ORGANISM: Artificial Sequence
<220> FEATURE:
<223> OTHER INFORMATION: Synthetic

<400> SEQUENCE: 35

Ser Phe Leu Pro Phe Thr Pro Ile Pro Leu Glu Leu Ser Leu Ala Ile
 1               5                  10                  15

Pro Ser Asn Pro Leu Val Phe Leu Ser Val Tyr Ile Phe Pro Gly Gly
            20                  25                  30

Pro Leu Leu Ser Leu Asp Arg His Leu Ser Ala Met Ala Ala Ala Thr
            35                  40                  45

Arg Phe Ser Val Gln Gln Val Glu His Ile Gly Met Cys Tyr Tyr His
 50                  55                  60

Pro Leu Arg Trp Trp Arg Lys Leu Phe Leu Lys Thr Gln Ala Lys Phe
 65                  70                  75                  80

Trp Leu Trp Gly Ser Pro Arg Ser Ser Gly His Gly Asn Thr Ile
                85                  90                  95

Ser Ile Thr Val Leu Leu Val Leu Arg Gln Glu Pro Leu Ile Pro Arg
            100                 105                 110

Leu Tyr Phe Leu Glu Pro Val Ile Ser Val His Leu Glu Ile His Thr
            115                 120                 125

Lys Val Ser Leu Leu His Ile Pro Ser Trp Met Ile Glu Gln Ser Val
            130                 135                 140

Ile Tyr Asp Pro His Thr Met Ile His Pro Ala Gly Ser Asn Trp Tyr
145                 150                 155                 160
```

```
Gln Cys Phe Pro Ser Pro Leu Leu Leu Phe Ser Tyr Gly Phe Arg Phe
            165                 170                 175

Val Pro Lys Lys Lys Ala Asn Asn Val Cys Asn Val Cys Ile Trp Tyr
            180                 185                 190

Ile Tyr Thr Gly Trp Ile Leu Cys Met Glu Met Leu Phe Ala Phe Arg
            195                 200                 205

Arg Asn Pro Thr Thr Pro
    210
```

PLANT CYCLOPROPANE FATTY ACID SYNTHASE GENES, PROTEINS, AND USES THEREOF

This application claims priority to U.S. Provisional Patent Application Ser. Nos. 60/345,152 and 60/393,937, filed on Dec. 21, 2001 and Jul. 3, 2002, respectively, both pending.

FIELD OF THE INVENTION

The present invention relates to isolated cyclopropane fatty acid synthase genes and polypeptides. The present invention also provides methods for using cyclopropane fatty acid synthase genes, polypeptides, and synthase products.

BACKGROUND OF THE INVENTION

Vegetable oils are utilized not only in the food industry, but also increasingly in the chemical industry. The utility of any particular oil depends upon chemical and physico-chemical properties of the oil, which is determined by the composition of the constituent fatty acids. Plant oils are often modified to meet industrial specifications. Such modification of vegetable oil has typically been achieved by chemical means (fractionation, interesterification, hydrogenation, or other chemical derivatization), but genetic means (plant breeding, mutagenesis and genetic engineering) are increasingly being used to provide novel oil feedstocks.

One class of particular interest is the class of fatty acids containing three carbon carbocyclic rings, which includes the cyclopropane fatty acids (CPA-FAs) and cyclopropene fatty acids (CPE-FAs). The cyclopropene ring confers two unique properties for these fatty acids and oils. First, hydrogenation produces large amounts of methyl-branched fatty acids. These will give the low temperature properties equivalent to unsaturated fatty acids and their esters without the oxidative susceptibility of the double bonds, and therefore may find uses in lubrication and related fields (Kai, Y. (1982) J. Am. Oil Chem. Soc. 59: 300-305). Moreover, the methyl-branched fatty acids may also be viewed as a replacement for isostearic acids formed in dimer acid production, and isostearic is an article of commerce in the oleochemical industry where it is used in applications as diverse as cosmetics and lubricant additives. Second, the cyclopropene ring is highly strained and readily ring opens in an exothermic reaction with electrophiles. Oils with high levels of cyclopropene fatty acid, such as *Sterculia foetida* oil, self-polymerize at elevated temperatures. This property is particularly applicable to the production of coatings and polymers. In the *Sterculia foetida* oil, sterculic acid reacts with acetic acid to produce a variety of acetyl esters, as well as with short or medium chain saturated fatty acids to yield monounsaturated estolide products (Kircher (1964) J. Org Chem. 29:1979-1982); all of these products can be further hydrogenated and saponified or hydrolyzed to form hydroxy fatty acids. Reaction of the oil with dibasic carboxylic acids should result in polymers. Moreover, sterculic acid might also be used as a biocide in fatty acid soap formulation.

On the other hand, CPE-FAs are considered an anti-nutritional factor in food oils. Many seed lipids containing CPE-FAs are extensively consumed by humans, especially in tropical areas (Ralaimanarivo et al. (1982) Lipids 17 (1): 1-10). It is well documented that dietary CPE-FAs lead to the accumulation of hard fats and other physiological disorders in animals (Phelps et al. (1965) Poultry Science 44: 358-394; Page et al. (1997) Comparative Biochemistry And Physiology B-Biochemistry & Molecular Biology 118 (1): 79-84). CPE-FAs are strong inhibitors of variety of desaturases in animals (Cao et al (1993) Biochimica et Biophysica Acta 1210 (1): 27-34; Fabrias et al. (1996) Journal of Lipid Research 37 (7): 1503-1509; Fogerty et al. (1972) Lipids 7(5): 335-338), which might be the cause of at least some of the observed disorders. Because of these health concerns, vegetable oils containing CPE-FAs must be treated with high temperature or hydrogenation before consumption. These treatments add to the oil processing costs, and also result in the presence of a certain percentage of trans fatty acids produced due the hydrogenation; the presence of such trans fatty acids are also undesirable. Therefore, it would be desirable to obtain plant oils with greatly reduced levels of CPE-FAs, as the availability of such oils would significantly reduce the processing costs, decrease the presence of undesirable hydrogenated fatty acids, and enhance the value of the oils for food consumption. Elimination of CPE-FAs would also enhance the value of unprocessed seeds or seed meal, such as cottonseed, as animal feed.

Currently, there are no commercial sources of oils rich in CPE-FAs. It is believed that plant CPE-FAs are synthesized from CPA-FAs via desaturation. *E. coli* and other bacteria have the ability to synthesize fatty acids containing a cyclopropane ring. The reaction is catalyzed by the enzyme cyclopropane fatty acid synthase (also known as cyclopropane synthase or unsaturated phospholipid methyltransferase; E.C. 2.1.1.16) and involves the addition of a methylene group from S-adenosylmethionine across the double bond of phospholipid hexadecenoyl or octadecenoyl groups. CPA-FAs (CFAs), such as dihydrosterculate (DHS) are characterized by a saturated 3-membered ring, as shown by the following structure, where X=OH for a free fatty acid, or an alcohol moiety for an ester:

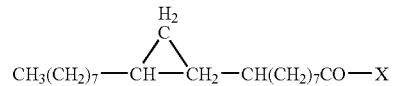

The cyclopropane fatty acid synthase gene in *E. coli* has been cloned and sequenced (Grogan et al. (1997) J. Bacteriol. 158:286-295 and Wang et al. (1992) Biochemistry 31: 11020-11028). No CPE-FAs have been reported in bacteria.

CPA-FAs (CPA-FA) and CPE-FAs (CPE-FA) are not widely distributed in high plants, but they are found in the seed oils of limited families, including the Malvaceae, Sterculiaceae, Bombaceae, Tilaceae, Mimosaceae and Sapindaceae (Smith (1970) *Progress in the Chemistry of Fats and Other Lipids* (Pergamon Press: New York) Vol. 11, pp139-177; Christie (1970) in *Topics in Lipid Chemistry* (Gunstone F D Ed.; Logos Press: London) Vol. 1, pp1-49; Badami and Patil (1981) Prog. Lipid Res. 19: 119-153). The CPA-FAs and CPE-FAs are not confined to seeds. Kuiper and Stuiver ((1972) Plant Physiol. 49: 307-309) have described long-chain CPA-FAs in various polar lipid classes of leaves of early spring plants. Yano et al. ((1972) Lipids 7: 30-34) and Schmid and Patterson ((1988) Phytochem. 27: 2831-2834) report that CPA-FAs and CPE-FAs are found in root, leaf stem and callus tissue in plants of the Malvaceae.

In a few plant species, CPA-FAs can reach high levels, in other words up to 40% in *Litchi chinensis* (Vickery et al. (1980) J. Am. Oil Chem. Soc. 57: 87-91; and Gaydou et al. (1993) J. Ag. Food Chem. 41: 886-890). However, it is more common to find CPE-FAs, particularly in the order Malvales (for example, as in the report by Bohannon and Kleiman (1978) Lipids 13: 270-273), and a biosynthetic pathway of CPE-FAs through CPA-FAs was postulated by Yano et al. ((1972) Lipids 7: 35-45). Thus, in plants, CPE-FAs exist primarily in the form of sterculic and malvalic acids, where malvalic acid is the one carbon homolog of sterculic acid and is obtained by chain shortening at the carboxyl end by ∀-oxidation. The CPE-FAs are usually accompanied with small amount of corresponding CPA-FAs, dihydrosterculic and dihydromalvalic acids. However, there have been no confirmed identified and isolated plant genes which encode proteins which are capable of synthesizing CPA-FAs. Moreover, plants with high levels of cyclopropene are not grown commercially.

Therefore, it would be desirable to be able to generate vegetable oils with high amounts of cyclopropane and CPE-FAs. One route is by identifying and isolating a plant gene which is capable of synthesizing CPA-FAs. Such a gene could then be used to transform oil crop plants. Identification of such a gene could also be used to reduce the levels of CPE-FAs by gene silencing techniques.

SUMMARY OF THE INVENTION

The present invention relates to compositions comprising cyclopropane fatty acid synthase ("CPA-FAS") genes and polypeptides. The present invention is not limited to any particular nucleic acid or amino acid sequence. The present invention also provides methods for using CPA-FAS genes and polypeptides.

Accordingly, in some embodiments, the present invention provides compositions comprising an isolated nucleic acid sequence encoding a plant CPA-FAS or portions thereof. In some embodiments, the plant is from the order Malvales; in some further embodiments, the plant is a *Sterculia* plant or a cotton plant. In some particular embodiments, the nucleic acid sequence encodes a *Sterculia* CPA-FAS or a portion thereof; in some further particular embodiments, the *Sterculia* is *Sterculia foetida*, and in even further particular embodiments, the isolated nucleic acid sequence comprises SEQ ID NO: 1. In other particular embodiments, the nucleic acid sequence encodes a cotton CPA-FAS or a portion thereof; in further particular embodiments, the cotton is *Gossypium arboreum*, and in even further particular embodiments, the isolated nucleic acid sequence comprises at least one of SEQ ID NOs:3, 4, 5, or 6. In other embodiments, the present invention provides an isolated nucleic acid sequence comprising a plant cyclopropane fatty acid synthase gene. In other embodiments, the present invention provides compositions comprising an isolated nucleic acid sequence comprising a nucleic acid sequence encoding an amino terminus of a plant cyclopropane fatty acid synthase; in some particular embodiments, the amino terminus of a plant cyclopropane fatty acid synthase comprises approximately the first about 420 to about 470 amino acids of a plant cyclopropane fatty acid synthase; in other particular embodiments, the amino terminus of a plant cyclopropane fatty acid synthase comprises the first approximately 440 amino acids of SEQ ID NO:2 or the amino acid sequence of SEQ ID NO:7; and in yet other particular embodiments, the coding sequence comprises about the first 1410 nucleotides of SEQ ID NO: 1 or comprises SEQ ID NO:3. In other embodiments, the present invention provides compositions comprising an isolated nucleic acid sequence comprising a nucleic acid sequence encoding an amino acid sequence homologous to an amino terminus of a plant cyclopropane fatty acid synthase; in some particular embodiments, the amino terminus of a plant cyclopropane fatty acid synthase comprises approximately the first about 420 to about 470 amino acids of a plant cyclopropane fatty acid synthase; in other particular embodiments, the amino terminus of a plant cyclopropane fatty acid synthase comprises the first approximately 440 amino acids of SEQ ID NO:2 or the amino acid sequence of SEQ ID NO:7.

The present invention is not limited to nucleic acid sequences encoding a plant CPA-FAS; indeed, it is contemplated that the present invention encompasses isolated nucleic acid sequences encoding homologs, variants, and portions or fragments of a plant CPA-FAS. Accordingly, in some embodiments, the present invention provides compositions comprising an isolated nucleic acid sequence that hybridizes under conditions of low to high stringency to a nucleic sequence comprising SEQ ID NOs: 1, 3, 4, 5, or 6. In some particular embodiments, the isolated nucleic acid hybridizes under conditions of high stringency to a nucleic sequence comprising SEQ ID NOs: 1, 3, 4, 5, or 6. In further embodiments, the hybridizing sequence encodes a polypeptide that catalyzes the addition of a methylene group across an unsaturated center of an unsaturated fatty acid. In other embodiments, the isolated nucleic acid sequences hybridize under conditions of low to high stringency to a nucleic sequence comprising about the first 1410 nucleotides of SEQ ID NO: 1 or comprising SEQ ID NO:3. In some particular embodiments, the isolated nucleic acid hybridizes under conditions of high stringency to a nucleic sequence comprising about the first 1410 nucleotides of SEQ ID NO:1 or comprising SEQ ID NO:3. In further embodiments, the hybridizing sequence encodes a polypeptide that catalyzes the addition of a methylene group across an unsaturated center of an unsaturated fatty acid.

In other embodiments, the present invention provides compositions comprising an isolated nucleic acid sequence encoding a plant CPA-FAS, wherein the synthase competes for binding to an unsaturated fatty acid substrate with a protein encoded by a nucleic acid sequence comprising SEQ ID NOs: 1 or at least one of SEQ ID NOs:3, 4, 5, or 6; in other embodiments, the present invention provides compositions comprising an isolated nucleic acid sequence encoding a plant CPA-FAS, wherein the synthase competes for binding to an unsaturated fatty acid substrate with a protein comprising amino acid sequence SEQ ID NO:2 or at least one of SEQ ID NO:7, 8, 9, or 10.

In other embodiments, the present invention provides compositions comprising an antisense sequence corresponding to any of the nucleic acid sequences encoding a plant CPA-FAS as described above. In yet other embodiments, the present invention provides compositions comprising ribozymes and hairpin loops targeted to any of the plant CPA-FAS coding sequences described above; in further embodiments, the present invention provides compositions comprising a nucleic acid sequence encoding ribozymes and hairpin loops targeted to any of the plant CPA-FAS coding sequences described above. In yet other embodiments, the present invention provides compositions comprising siRNAs targeted to a sequence in an mRNA transcribed from any of the nucleic acid sequences encoding a plant cyclopropane fatty acid synthase as described above; in yet further embodiments, the present invention provides compositions comprising nucleic acid sequences encoding an siRNA targeted to a sequence in an mRNA transcribed from any of the nucleic acid sequences encoding a plant cyclopropane fatty acid synthase as described above.

In some embodiments of the present invention, a nucleic acid sequence described above is operably linked to a heterologous promoter. In further embodiments, the sequence described above linked to a heterologous promoter is contained within a vector.

In other embodiments, the invention provides compositions comprising a purified polypeptide encoded by any of the nucleic acid sequences described above which when transcribed and translated result in expression of a polypeptide; in some embodiments, the polypeptide is purified from a recombinant organism transformed with any of the nucleic sequences described above which when transcribed and translated result in expression of a polypeptide. In other embodiments, the present invention provides compositions comprising a purified plant CPA-FAS or portions thereof. In some embodiments, the plant CPA-FAS is purified from a plant of order Malvales; in other embodiments, the plant CPA-FAS is purified from *Sterculia* ; in other embodiments, the CPA-FAS is purified from *Sterculia foetida*; in yet other embodiments, the plant CPA-FAS comprises amino acid sequence SEQ ID NO:2. In other embodiments, the plant CPA-FAS is purified from cotton; in yet other embodiments, the plant CPA-FAS comprises at least one of amino acid SEQ ID NOs:7, 8, 9, or 10.

In further embodiments, the present invention provides an organism transformed with any of the nucleic acid sequences described above. In other embodiments, the present invention provides an organism transformed with a heterologous gene encoding a plant CPA-FAS or a portion thereof; in some embodiments, the gene is from a Malvales plant; in other embodiments the gene is a *Sterculia* gene; in yet other embodiments, the gene is a *Sterculia foetida* gene; and in yet other embodiments, the gene encodes SEQ ID NO:2. In yet other embodiments, the gene is a cotton gene; in other particular embodiments, the gene encodes a CPA-FAS comprising at least one of amino acid SEQ ID NOs: 7, 8, 9, or 10.

In other embodiments, the present invention provides organisms co-transformed with a first heterologous gene encoding a plant CPA-FAS and with a second heterologous gene encoding a fatty acid desaturase. In yet other embodiments, the present invention provides organisms co-transformed with a heterologous gene encoding a fusion polypeptide comprising a plant CPA-FAS and a fatty acid desaturase.

In other embodiments of the present invention, a transformed organism as described above is either a plant or microorganism. In a preferred embodiment, the organism is a plant. In other embodiments, a plant cell is transformed with any of the nucleic acid sequences described above. In yet other embodiments, a plant seed is transformed with any of the nucleic acid sequences described above. In yet other embodiments, the invention provides oils from plants transformed as described above. In further embodiments, a transformed organism as described above is a bacteria; in other embodiments, the invention provides oils from such transformed bacteria.

In other embodiments, the present provides methods for expressing a plant cyclopropane fatty acid synthase in a plant, comprising providing a vector comprising any of the nucleic acid sequences described above which encode a plant CPA-FAS or portion thereof and plant tissue, and transfecting the plant tissue with the vector under conditions such that the synthase is expressed. In other embodiments, the present invention provides methods for decreasing expression of CPA-FAS in plants, comprising providing a vector comprising a nucleic acid sequence encoding an antisense sequence corresponding to any of the nucleic acid sequences described above which encode a plant CPA-FAS or portion thereof, and plant tissue, and transfecting the plant tissue with the vector under conditions such that the antisense sequence is expressed and the expression of CPA-FAS is decreased. In yet other embodiments, the present invention provides methods for decreasing expression of CPA-FAS in plants, comprising providing a vector encoding an siRNA targeted to any of the nucleic acid sequences described above which encode a plant CPA-FAS or portion thereof, and plant tissue, and transfecting the plant tissue with the vector under conditions such that the siRNA is expressed and the expression of CPA-FAS is decreased.

In further embodiments, the invention provides methods for producing a variant of plant CPA-FAS, comprising providing a nucleic acid sequence encoding a plant CPA-FAS, and mutagenizing the nucleic acid sequence so as to produce a variant; in still other embodiments, the methods further comprise screening the variant for activity. In some embodiments, the variant is a fragment of CPA-FAS which has CPA-FAS activity. In other embodiments, the variant is a mutated CPA-FAS which has altered CPA-FAS activity when compared to the unmutated CPA-FAS.

In other embodiments, the present invention provides methods of producing fatty acids with three carbon carbocyclic rings, such as fatty cyclopropane fatty acids, in vitro, comprising providing a purified plant CPA-FAS and at least one fatty acid substrate of the enzyme, and incubating the synthase with the substrate under conditions such that fatty acids with three carbon carbocyclic rings, such as cyclopropane fatty acids, are produced. In particular embodiments, the substrate of the plant CPA-FAS is an unsaturated fatty acid with variable chain length and from none to one or more additional functional groups comprising acetylenic bonds, conjugated acetylenic and ethylenic bonds, allenic groups, cyclopentene and furan rings, or epoxy-, hydroxy- and keto-groups, wherein the substrates are either free fatty acids, or fatty acids incorporated into a larger molecule; in other particular embodiments, the substrate is oleic or palmitoleic acid.

In other embodiments, the present invention provides methods of producing fatty acids with three carbon carbocyclic rings, such as cyclopropane fatty acids, in vitro, comprising providing an isolated nucleic sequence encoding a plant CPA-FAS and at least one fatty acid substrate of the enzyme, and incubating the sequence with the substrate in a transcription/translation system under conditions such that the sequence is expressed and cyclopropane fatty acids are produced. In particular embodiments, the substrate of the plant CPA-FAS is selected from the group as described above.

In other embodiments, the invention provides methods of producing fatty acids with three carbon carbocyclic rings, such as cyclopropane fatty acids, in vitro, comprising providing a purified plant CPA-FAS, a purified fatty acid desaturase and at least one fatty acid substrate of the desaturase, and incubating the CPA-FAS and the desaturase with the substrate(s) under conditions such that fatty acids with three carbon carbocyclic rings, such as cyclopropane fatty acids, are produced. In preferred embodiments, the fatty acid substrate(s) of the desaturase is any fatty acid to which an additional double bond can be added, which double bond can be the site of addition of a methylene group by the CPA-FAS.

In further embodiments, the present invention provides methods of producing fatty acids with three carbon carbocyclic rings, such as cyclopropane fatty acids, by fermentation, comprising providing a microorganism transformed with a heterologous gene encoding a plant CPA-FAS and at least one substrate of the plant CPA-FAS, and incubating the microorganism with the substrate under conditions such that fatty acids with three carbon carbocyclic rings, such as cyclopropane fatty acids, are produced. In particular embodiments, the fatty acid substrate of the CPA-FAS is a member of the group as described above.

In other embodiments, the present invention provides methods of producing fatty acids with three carbon carbocyclic rings, such as cyclopropane fatty acids, by fermentation, comprising providing a microorganism co-transformed with a first heterologous gene encoding a plant CPA-FAS and with a second heterologous gene encoding a fatty acid desaturase and at least one substrate of the desaturase, and incubating the microorganism with the substrate under conditions such that fatty acids with three carbon carbocyclic rings, such as cyclopropane fatty acids, are produced. In preferred embodiments, the fatty acid substrate of the desaturase is a member of the group described above.

In further embodiments, the present invention provides methods of producing fatty acids with three carbon carbocyclic rings, such as cyclopropane fatty acids, by fermentation, comprising providing a microorganism transformed with a heterologous gene encoding a fusion polypeptide comprising a plant CPA-FAS and a fatty acid desaturase and at least one substrate of the desaturase, and incubating the microorganism with the substrate under conditions such that fatty acids with three carbon carbocyclic rings, such as cyclopropane fatty acids, are produced. In particular embodiments, the fatty acid substrate of the desaturase is a member of the group described above.

In other embodiments, the present invention provides methods of producing fatty acids with three carbon carbocyclic rings, such as cyclopropane fatty acids, in a plant comprising providing a plant and a heterologous gene encoding a plant CPA-FAS, and transforming the plant with the heterologous gene such that fatty acids with three carbon carbocyclic rings, such as cyclopropane fatty acids, are produced. In other embodiments, the present invention provides methods of producing fatty acids with three carbon carbocyclic rings, such as cyclopropane fatty acids, in a plant comprising growing a plant transformed with a heterologous gene encoding a plant CPA-FAS under conditions such that fatty acids with three carbon carbocyclic rings, such as cyclopropane fatty acids, are produced. In yet other embodiments, the present invention provides methods of producing fatty acids with three carbon carbocyclic rings, such as cyclopropane fatty acids, in a plant comprising providing a plant, a first heterologous gene encoding a plant CPA-FAS, and a second heterologous gene encoding a desaturase, and co-transforming the plant with the first heterologous gene and with the second heterologous gene such that fatty acids with three carbon carbocyclic rings, such as cyclopropane fatty acids, are produced. In other embodiments, the present invention provides methods of producing fatty acids with three carbon carbocyclic rings, such as cyclopropane fatty acids, in a plant comprising growing a plant transformed with a first heterologous gene encoding a plant CPA-FAS, and with a second heterologous gene encoding a desaturase, under conditions such that fatty acids with three carbon carbocyclic rings, such as cyclopropane fatty acids, are produced. In still other embodiments, the present invention provides methods of producing fatty acids with three carbon carbocyclic rings, such as cyclopropane fatty acids, in a plant comprising providing a plant and a heterologous gene encoding a fusion polypeptide comprising a plant CPA-FAS and a fatty acid desaturase, and transforming a plant with the heterologous gene, such that fatty acids with three carbon carbocyclic rings, such as cyclopropane fatty acids, are produced. In other embodiments, the present invention provides methods of producing fatty acids with three carbon carbocyclic rings, such as cyclopropane fatty acids, in a plant comprising growing a plant with a heterologous gene encoding a fusion polypeptide comprising a plant CPA-FAS and a fatty acid desaturase under conditions such that fatty acids with three carbon carbocyclic rings, such as cyclopropane fatty acids, are produced.

In other particular embodiments, the present invention provides transgenic plants comprising any of the nucleic acid sequences of the invention described above, where the nucleic acid sequences are under control of promoters that control expression of the nucleic acid sequence in a target tissue of the plant or in a target developmental phase of the plant, or under control of promoters that are inducible. It is contemplated that such transgenic plants may be used for any of the methods described above for producing cyclopropane fatty acids in plants.

In yet other embodiments, the present invention provides methods for screening plant CPA-FASs comprising providing a candidate plant CPA-FAS and analyzing said candidate CPA-FAS for the presence of the S-adenosyl methionine binding motif and catalytic cysteine in the amino acid sequence; preferably, the motif and catalytic cysteine are present in the carboxy-terminus of the plant CPA-FAS.

DESCRIPTION OF THE FIGURES

FIG. 5 shows the deduced amino acid sequence (SEQ ID NO:2) for the *Sterculia* cyclopropane fatty acid synthase (SCPA-FAS) shown in FIG. 4.

FIG. 11 (SEQ ID NOS:2 and 19) shows an amino acid alignment between *Sterculia* and bacterial cyclopropane fatty acid synthase. The portion from about amino acid 470 to amino acid 864 (the conserved carboxyl terminus) was used to prepare antibody to the *Sterculia* enzyme.

FIG. 12 shows the locations of the primers relative to the *Sterculia* cyclopropane fatty acid synthase coding sequence (the primers (SEQ ID NOS:21 and 22) are shown above the coding sequence), where the primers were used for PCR amplification of the coding sequence for the conserved carboxyl terminus.

FIG. 13 (SEQ ID NOS: 11 and 23) shows the protein expressed in BL21 (SEQ ID NO:11). The highlighted portion is derived from the vector, which contains a 6-histidine tag for purification.

FIG. 14 shows nucleic acid sequences of three ESTs discovered in cotton (*Gossypium Arboreum*) by blasting NCBI database with the amino acid sequence from *Sterculia*cyclopropane fatty acid synthase. Panel A shows EST1 (SEQ ID NO:3), panel B shows EST2 (SEQ ID NO:4), and panel C shows EST3 (SEQ ID NO:5).

FIG. 16 shows predicted amino acid sequences for *Sterculia* cyclopropane fatty acid synthase (panel A, SEQ ID NO:2), cotton EST1 (panel B, SEQ ID NO:7), cotton EST2 (panel C, SEQ ID NO:8), cotton EST3 (panel D, SEQ ID NO:9) and cotton Contig 1 (EST2_3, panel E, SEQ ID NO:10).

FIG. 17 shows an alignment of the amino acid sequence of the *Sterculia* cyclopropane fatty acid synthase (SEQ ID NO:2), and the predicted amino acid sequences of two cotton EST sequences, EST1 (SEQ ID NO:7) and the Contig 1 (EST2_3, SEQ ID NO:10).

GENERAL DESCRIPTION OF THE INVENTION

Figure 1:
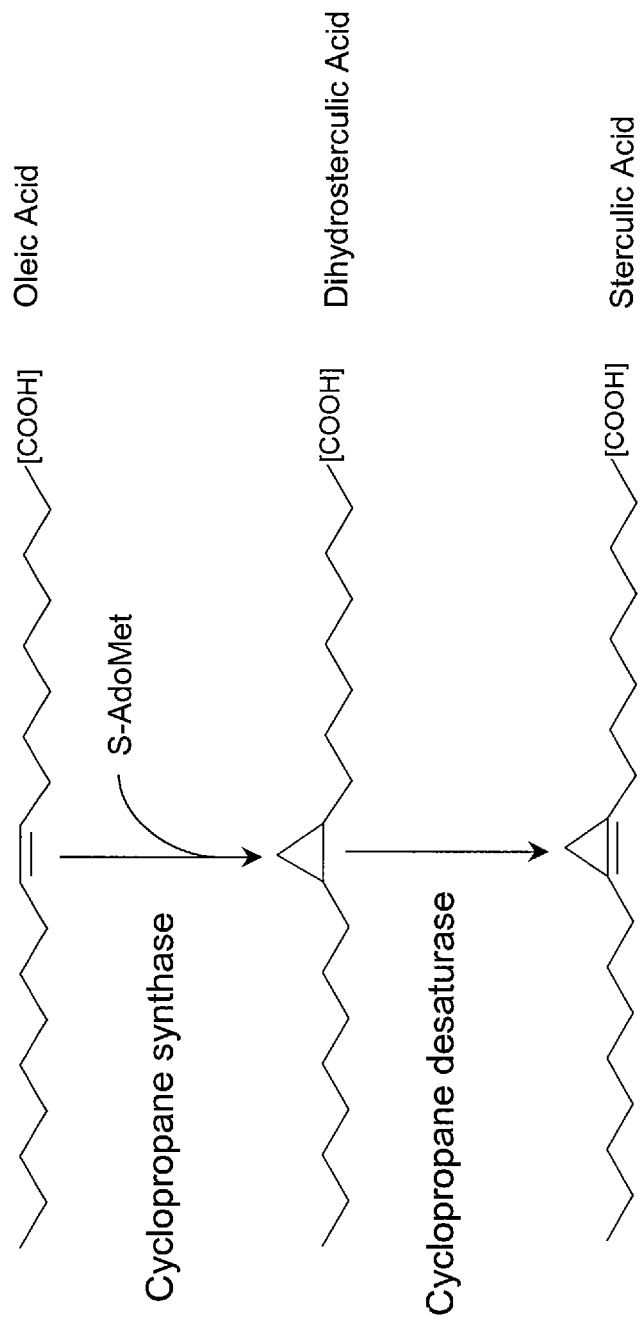
FIG. 1 shows the proposed pathway for the biosynthesis of sterculic acid.

The present invention relates to compositions comprising plant cyclopropane fatty acid (CPA-FAS) genes and polypeptides. The present invention encompasses compositions comprising both native and recombinant forms of the enzyme, as well as mutant and variant forms, some of which possess altered characteristics relative to the wild-type. The present invention also provides methods for using plant CPA-FAS genes, polypeptides, and synthase products.

In some embodiments, the present invention provides novel isolated nucleic acid sequences encoding a plant cyclopropane fatty acid synthase. In other embodiments, the invention provides isolated nucleic acid sequences encoding mutants, variants, homologs, chimeras, and fusions of plant cyclopropane fatty acid synthase. In other embodiments, the present invention provides methods of generating such sequences. In other embodiments, the present invention provides methods of cloning and expressing such sequences, as well as methods of purifying and assaying the expression product of such sequences.

In additional embodiments, the invention provides purified plant CPA-FAS polypeptides. In other embodiments, the present invention provides mutants, variants, homologs, chimeras, and fusion proteins of plant CPA-FAS. In some embodiments, the present invention provides methods of purifying, and assaying the biochemical activity of wild type as well as mutants, variants, homologs, chimeras, and fusions of plant cyclopropane fatty acid synthase polypeptides, as well as methods of generating antibodies to such proteins.

In some embodiments, the present invention provides methods of using novel isolated nucleic acid sequences encoding a plant cyclopropane fatty acid synthase to produce products of the synthase activity. In some embodiments, the methods involve adding the sequences to in vitro transcription and translations systems which include the substrates of the synthase, such that the products of the synthase may be recovered. In other embodiments, the methods involve transforming organisms with the sequences such that the sequences are expressed and products of the synthase are produced. In particular embodiments, the products are recovered. In other embodiments, the products remain in situ.

In some embodiments, the present invention provides methods of using recombinant plant CPA-FAS polypeptides to produce products of the synthase activity. In some embodiments, the methods involve adding the polypeptides to in vitro systems which include the substrates of the synthase, such that the products of the synthase may be recovered.

In other embodiments, the methods involve transforming a plant with a novel isolated nucleic acid sequence encoding a plant cyclopropane fatty acid synthase such that products of the synthase are produced.

In some embodiments, the present invention provides an organism transformed with heterologous gene encoding a plant cyclopropane fatty acid synthase. In some embodiments, the organism is a microorganism. In other embodiments, the organism is a plant.

In some embodiments, the present invention also provides a cell transformed with an heterologous gene encoding a plant cyclopropane fatty acid synthase. In some embodiments, the cell is a microorganism. In other embodiments, the cell is a plant cell.

In other embodiments, the present invention provides a plant seed transformed with a nucleic acid sequence encoding a plant cyclopropane fatty acid synthase. In yet other embodiments, the present invention provides an oil from a plant transformed with a plant cyclopropane fatty acid synthase.

Definitions

To facilitate an understanding of the present invention, a number of terms and phrases as used herein are defined below:

The term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue.

The term "crop" or "crop plant" is used in its broadest sense. The term includes, but is not limited to, any species of plant or algae edible by humans or used as a feed for animals or used, or consumed by humans, or any plant or algae used in industry or commerce.

The term "oil-producing species" refers to plant species which produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids.

The term "*Sterculia*" refers to a plant or plants from the genus *Sterculia* of the family Sterculiaceae of the order Malvales. Non-limiting examples of *Sterculia* include plants from the species *S. foetida, S. oblongata, S. Rinopetala, S. urens, S. villosa*. The term also refers to *S. foetida* plants from which nucleic acid sequence SEQ ID NO: 1 was isolated.

The term "cotton" refers to a cotton plant or plants from the genus *Gossypium* of the family Malvaceae of the order Malvales ; the genus *Gossypium* contains at least 39 species. Non-limiting examples of cotton include plants from the species *G. arboreum, G. hirsutum, G. herbaceum*, and *G. barbadense*. The term also refers to *Gossypium arboreum* plants from which nucleic acid sequences SEQ ID NOs: 3, 4, and 6 were derived.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The term "host cell" refers to any cell capable of replicating and/or transcribing and/or translating a heterologous gene.

The term "methylene-added fatty acid" refers to a fatty acid where a methylene group has been added to the hydrocarbon chain to produce methyl- or methylene-branched or three-member carbocyclic ring structure.

The term "three member carbocyclic ring fatty acid" refers to a fatty acid with a cyclopropane or cyclopropene ring.

The term "cyclopropane fatty acid" (CPA-FA) refers to a fatty acid characterized by a saturated 3-membered ring. The term "cyclopropene fatty acid" (CPE-FA) refers to a fatty acid characterized by an unsaturated 3-membered ring.

The term "cyclopropane fatty acid synthase" (CPA-FAS) or "cyclopropane synthase" refers to a polypeptide with the capacity to synthesize a fatty acid containing a cyclopropane ring. When presented with substrates other than cis-monounsaturated fatty acids, or after modification of just a few amino acids, the polypeptide is contemplated to function more broadly as a three-member carbocyclic ring fatty acid synthase or as a methylene-added fatty acid synthase. The basic reaction involves addition of a methylene group across the double bond. Thus, the polypeptide catalyzes the addition of a methylene group across the unsaturated center of an unsaturated fatty acid, and includes the addition of a methylene group across a double bond of an acyl group. The methionine can be obtained from S-adenosylmethionine. Typically, the acyl group is a hexadecenoyl or octadecenoyl group, although other fatty acyl groups of different chain lengths and degrees of unsaturation are also contemplated as substrates. The fatty acyl group is believed to be esterified to a phospholipid; such phospholipid substrates include phosphatidylcholine, phosphatidylethanolamine, and phospatidylglycerol. The term "recombinant cyclopropane fatty acid synthase" (recombinant CPA-FAS) refers to the expression product of a recombinant nucleic acid molecule or of a heterologous gene encoding CPA-FAS. Having "CPA-FAS activity" refers to having the functionality of a CPA-FAS, or having the capacity to synthesize a fatty acid containing a cyclopropane ring or catalyze the reaction described above. A "plant CPA-FAS" is an enzyme originally obtained from a plant source; the enzyme may be modified where such modifications include but are not limited to truncation, amino acid deletions, additions, and substitutions, and glycosylation, and where the resulting modified enzyme possesses CPA-FAS activity.

The term "competes for binding" is used in reference to a first polypeptide with enzymatic activity which binds to the same substrate as does a second polypeptide with enzymatic activity, where the second polypeptide is variant of the first polypeptide or a related or dissimilar polypeptide. The efficiency (for example, kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferable greater than 75% sequence identity, and still more preferably greater than 90% sequence identity, with a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties (for example, replacement of leucine with isoleucine). More rarely, a variant may have "non-conservative" changes (for example, replacement of a glycine with a tryptophan). Similar minor variations may also include amino acid deletions or insertions (in other words additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on).

The term "gene" refers to a nucleic acid (for example, DNA or RNA) sequence that comprises coding sequences necessary for the production of an RNA, or a polypeptide or its precursor (for example, proinsulin). A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "heterologous gene" refers to a gene encoding a factor that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "an oligonucleotide having a nucleotide sequence encoding a gene" or "a nucleic acid sequence encoding" a specified polypeptide refers to a nucleic acid sequence comprising the coding region of a gene or in other words the nucleic acid sequence which encodes a gene product The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described infra.

Low stringency conditions when used in reference to nucleic acid hybridization comprise conditions equivalent to binding or hybridization at 42EC in a solution consisting of 5×SSPE (43.8 g/l NaCl, 6.9 g/l NaH$_2$PO$_4$XH$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 :g/ml denatured salmon sperm DNA followed by washing in a solution comprising 5×SSPE, 0.1% SDS at 42EC when a probe of about 500 nucleotides in length is employed.

High stringency conditions when used in reference to nucleic acid hybridization comprise conditions equivalent to binding or hybridization at 42EC in a solution consisting of 5×SSPE (43.8 g/l NaCl, 6.9 g/l NaH$_2$PO$_4$XH$_2$O and 1.85 g/l EDTA, pH adjusted to 7.4 with NaOH), 0.5% SDS, 5× Denhardt's reagent and 100 :g/ml denatured salmon sperm DNA followed by washing in a solution comprising 0.1×SSPE, 1.0% SDS at 42EC when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (in other words, it is the complement of) the single-stranded nucleic acid sequence under conditions of low to high stringency as described above.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+ 0.41 (% G+C), when a nucleic acid is in aqueous solution at 1 M NaCl (See for example, Anderson and Young, Quantitative Filter Hybridization (1985) in Nucleic Acid Hybridization). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q $\exists$replicase, MDV-1 RNA is the specific template for the replicase (Kacian et al. (1972) Proc. Natl. Acad. Sci. USA, 69:3038).

Other nucleic acid will not be replicated by this amplification enzyme. Similarly, in the case of T7 RNA polymerase, this amplification enzyme has a stringent specificity for its own promoters (Chamberlin et al (1970) Nature, 228:227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics, 4:560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) *PCR Technology*, Stockton Press).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (for example, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (in other words precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605, incorporated herein by reference), mannopine synthase, octopine synthase (ocs), superpromoter (see for example, WO 95/14098), and ubi3 (see for example, Garbarino and Belknap (1994) Plant Mol. Biol. 24:119-127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (for example, heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) *Molecular Cloning: A Laboratory Manual,* 2nd ed., Cold Spring Harbor Laboratory Press, New York, pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "selectable marker" refers to a gene which encodes an enzyme having an activity that confers resistance to an antibiotic or drug upon the cell in which the selectable marker is expressed, or which confers expression of a trait which can be detected for example, luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "vector refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (for example, particle bombardment) and the like.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacteriuti*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" *Agrobacteria; Agrobacterium* strains which cause production of octopine (for example, strain LBA4404, Ach5, B6) are referred to as "octopine-type" *Agrobacteria*; and *Agrobacterium* strains which cause production of agropine (for example, strain EHA105, EHA101, A281) are referred to as "agropine-type" *Agrobacteria*.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807, the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgenic" when used in reference to a plant or fruit or seed (in other words, a "transgenic plant" or "transgenic fruit" or a "transgenic seed") refers to a plant or fruit or seed that contains at least one heterologous gene in one or more of its cells. The term "transgenic plant material" refers broadly to a plant, a plant structure, a plant tissue, a plant seed or a plant cell that contains at least one heterologous gene in one or more of its cells.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in, the originally transformed cell are included in the definition of transformants.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (in other words, altered characteristics) when compared to the wild-type gene or gene product. It is noted that naturally-occurring mutants can be isolated; these are identified by the fact that they have altered characteristics when compared to the wild-type gene or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, which link the two strands of the double strand, as well as stem and other folded structures, which may be present within the linking sequence. siRNAs appear to function as key intermediaries in triggering RNA interference in invertebrates and in vertebrates, and in triggering sequence-specific RNA degradation during posttranscriptional gene silencing in plants.

The term "target RNA molecule" refers to an RNA molecule to which at least one strand of the short double-stranded region of an siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector which is not integrated into the genome. The expression of the gene is either completely or partially inhibited. RNAi may also be considered to inhibit the function of a target RNA; the function of the target RNA may be complete or partial.

The term "posttranscriptional gene silencing" or "PTGS" refers to silencing of gene expression in plants after transcription, and appears to involve the specific degradation of mRNAs synthesized from gene repeats.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. The term "altered levels" refers to the production of gene product(s) in transgenic organisms in amounts or proportions that differ from that of normal or non-transformed organisms.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31-9.58).

The term "Northern blot analysis" and "Northern blot" and "Northern" as used herein refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The terms "protein" and "polypeptide" refer to compounds comprising amino acids joined via peptide bonds and are used interchangeably.

As used herein, where "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule; furthermore, an "amino acid sequence" can be deduced from the nucleic acid sequence encoding the protein.

The term "portion" when used in reference to a protein (as in "a portion of a given protein") refers to fragments of that protein. The fragments may range in size from four amino acid residues to the entire amino sequence minus one amino acid.

The term "homology" when used in relation to amino acids refers to a degree of similarity or identity. There may be partial homology or complete homology (in other words, identity). "Sequence identity" refers to a measure of relatedness between two or more proteins, and is given as a percentage with reference to the total comparison length. The identity calculation takes into account those amino acid residues that are identical and in the same relative positions in their respective larger sequences. Calculations of identity may be performed by algorithms contained within computer programs.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a plant CPA-FAS includes, by way of example, such nucleic acid in cells ordinarily expressing a DES, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. The term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

DETAILED DESCRIPTION OF THE INVENTION

The presently claimed invention provides compositions comprising isolated plant CPA-FAS genes and polypeptides, and in particular to compositions comprising isolated *Sterculia* and cotton CPA-FAS genes and polypeptides. The present invention also provides methods for using plant CPA-FAS genes, polypeptides, and synthase products; such methods include but are not limited to plant CPA-FAS genes and polypeptides in the production of cyclopropane fatty acids. The description below provides specific, but not limiting, illustrative examples of embodiments of the present invention.

I. Plant Cyclopropane Fatty Acid Synthase Genes and Polypeptides

The biosynthetic pathway of CPA-FAs in bacteria is well characterized (Grogan and Cronan (1997) Microbiol Molecular Biol Rev 61 (4): 429-441). The first cyclopropane synthase gene was cloned from *E. coli*, based upon its ability to complement CPA-FA deficient mutant (Grogan and Cronan (1984) J Bacteriol 158 (1): 286-295). It was clearly demonstrated that bacterial CPA-FAs were directly synthesized from mono-unsaturated fatty acids by addition of a methylene group, derived from S-adenosylmethionine, cross the double bond. However, the substrates of the enzyme appear to be mono-unsaturated fatty acids esterified to phospholipids, most likely phosphatidylethanolamine (Grogan and Cronan (1997) Microbiol Molecular Biol Rev 61 (4): 429-441). After the identification of bacterial cyclopropane synthase, three genes from *M tuberculosis* were found with the ability to introduce a cyclopropane ring onto mycolic acids (Yuan and Barry (1996) Proc Nat'l Acad Sci USA 93 (23): 12828-12833; Yuan et al. (1995) Proc Nat'l Acad Sci USA 92 (14): 6630-6634).

Even though the existence of CPE-FAs in plants has been known for at least several decades, the biosynthesis of this particular kind of fatty acids has received very little attention to date. In attempt to understand the biosynthesis of CPE-FAs, Yano et al ((1972) Lipids 7: 35-45) conducted in vivo labeling experiments with several species of Malvaceae. The authors concluded that the pathway of CPE-FA synthesis involved an initial formation of dihydrosterculic acid from oleic acid and a subsequent desaturation of dihydrosterculic acid to sterculic acid, and they postulated that the methylene group was derived from methionine through S-adenosyl-methionine (see FIG. 1). They also indicated that sterculic acid was unlikely to be derived directly by methylene addition across the 9,10-triple bond of stearolic acid, because no conversion of $[1-^{14}C]$ stearolic acid to sterculic acid was observed from the labeling experiments. Subsequently, there has been essentially no further research into plant cyclopropane fatty acid synthases.

It has been reported that, in *Sterculia foetida* seeds, total CPE-FA levels were over 68% of total fatty acids, with small amounts of dihydrosterculic acid also present (Badami and Patil (1981) Prog. Lipid Res. 19: 119-153; Christie (1970) in *Topics in Lipid Chemistry* (Gunstone F D Ed.; Logos Press: London) Vol. 1, pp 1-49; Sebedio and Gradgirard (1989) Prog. Lipid Res. 28:303). With oil content about 55% of its dry weight, *Sterculia* developing seeds appeared to be an ideal tissue to study the biosynthesis of CPE-FAs. Moreover, based upon several assumptions, it was reasoned that *Sterculia* seed would be a good source of a plant cyclopropane fatty acid synthase (CPA-FAS). It was inferred that the biosynthesis of sterculic acid occurs by a two step reaction, catalyzed by two separate enzymes, namely cyclopropane synthase and cyclopropane desaturase; this inference is based upon the in vivo labeling experiments (Yano et al (1972) Lipids 7: 35-45), and the knowledge of cyclopropane synthesis in bacteria. It was also inferred that the cyclopropane synthase from *Sterculia* would share certain some degree of similarity with bacterial cyclopropane synthase. Moreover, because *Sterculia* seeds have high levels of oil, and the oil has high levels of high CPE-FAs, it was inferred that the transcript levels of the enzymes responsible for the synthesis of CPE-FAs should be reasonably high in developing seed tissue as well.

The first line of evidence that *Sterculia* seeds contained high levels of the enzymes required for CPA-FA and CPE-FA synthesis was based upon in vivo labeling studies of developing *Sterculia* seed homogenates (see Example 2). When samples of these homogenates were incubated with labeled S-adenosyl methionine (SAM) and the lipid products saponified, labeled free fatty acid was the major constituent in the saponified product (greater than 90%). When analyzed after derivatization with ethereal diazomethane and separation by C18 reversed-phase TLC, a single radioactive spot co-eluted with the methyl dihycrosterculate standard. Thus, it was shown the a cell-free extract from developing *Sterculia foetida* seeds could add a labeled methylene group from S-adenosyl-methionine to oleate to produce dihydrosterculate. This reaction has not been reported previously in plant extracts. Additional experiments indicated that the enzyme synthesizing CFA-FA was either a membrane-associated or an integral membrane protein, and that oleoyl-phosphatidylcholine was the substrate for the enzyme. Thus, these results indicated that the enzyme synthesizing CPA-FA was a CPA-FAS with some characteristics similar to that of the *E. coli* CPA-FAS.

Based upon this evidence, a strategy for identifying a plant CPA-FAS was developed. This strategy begins with the observation of the presence of CPA-FAs or CPE-FAs in a plant tissue. The next step is labeling studies of tissue homogenates, to confirm that the ability to synthesize CPA-FAs and/or CPE-FAs is in fact present in the tissue. The next step is obtaining a large number of seed-specific ESTs by utilizing a cDNA library prepared from the tissue (which for *Sterculia* is the developing seeds) which synthesize cyclopropane fatty acid, preferably to a relatively high level. For *Sterculia*, the fatty acid profiles of developing seeds were analyzed, to determine the developmental stage when CPE-FAs accumulated at the highest rate; seeds obtained at this developmental stage are then used to prepare a cDNA library. A small first subset of the initial set of clones (about 10%) are sequenced, from which a smaller subset (about 7%) are obtained with an average reading length of about 500 bp. This smaller subset is BLAST searched to discover and select abundant sequences (which for *Sterculia* cDNA library represented about 30% of the clones), which are then subtracted out of the remaining clones. The subtracted clones are then sequenced, and a second subset selected with an average reading length of 500 bp. These are also subjected to BLAST searches, resulting in a smaller set of ESTs which show a certain degree of similarity with bacterial cyclopropane synthase. These EST sequences are then compiled to identify at least one putative plant CPA-FAS.

Next, at least one complete cDNA clone encoding a putative plant CPA-FAS is compiled from overlapping clones, and used to confirm the identity of the encoded sequence as a plant CPA-FAS. Confirmation is obtained by expression of the clone in either an in vitro or in vivo system, such that either CPA-FAs are produced only upon expression of the clone, or increased amounts of CPA-FAs are produced only upon expression of the clone. Preferably, the system is in vivo, and the clone transfected into and expressed in a host organism. More preferably, the system in one in which CPA-FAs are not normally produced, such as when the host organism is a yeast strain. Even more preferably, the system possesses a suitable substrate, such as oleic acid, and is able to tolerate the presence of unusual fatty acids, such as when the host organism is cultured tobacco cells.

Figure 3:
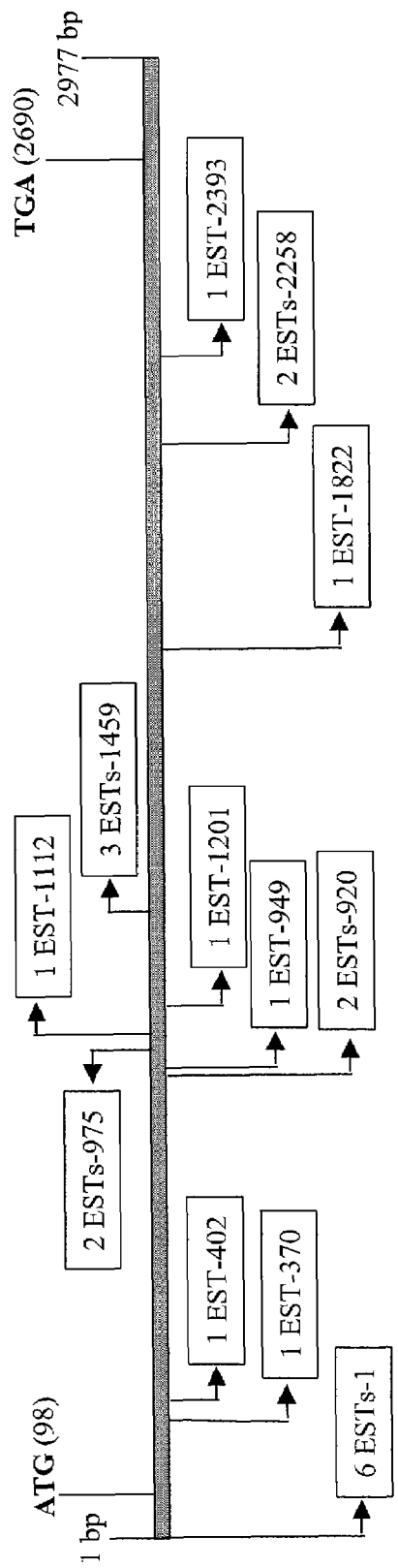
FIG. 3 shows the distribution of *Sterculia* seed ESTs along the putative *Sterculia* cyclopropane synthase cDNA derived from clones R50D5 and R15C3. The start codon is located at 98 bp and the stop codon is locate at 2690 bp. In each box, the first number is the number of ESTs, and the second number is the location where the EST(s), starts. The arrow indicates the direction and region covered by the given EST(s).
Figure 4:
FIG. 4 shows a nucleic acid sequence (SEQ ID NO: 1) for *Sterculia* cyclopropane fatty acid synthase (SCPA-FAS).

This strategy was utilized for developing *Sterculia* seeds, as described in the Examples, and resulted in the identification of 23 ESTs derived from the same gene which were found to share some similarity with bacterial cyclopropane synthase; the distribution of these ESTs along the gene is shown in FIG. 3. The relative transcript abundance of this gene is 0.36%, which is consistent with the 68% of CPE-FA content in *Sterculia* seeds. A full length clone was assembled from the ESTs comprising SEQ ID NO:1 (as shown in FIG. 4). The predicted protein is 864 amino acids long (SEQ ID NO:2, as shown in FIG. 5). Thus, this protein is about 470 amino acids longer than the *E. coli* CPA-FAS. The *Sterculia* CPA-FAS is 49% similar to and 32% identical to the *E. coli* sequence over the region of overlap, which is the carboxy terminus. The *Sterculia* CPA-FAS thus has an additional approximately 470 amino acids at the amino terminus.

Expression of the plant CPA-FAS in yeast and tobacco suspension cells resulted in the synthesis of dihydrosterculic acid in both systems, and especially in tobacco cells, where the amount of CPA-FA was high as 6.3% of total fatty acids. The radioactivity from both [1-$^{14}$C] oleic acid and L-[methyl-$^{14}$C] methionine were effectively incorporated into dihydrosterculic acids in the transgenic tobacco cells (see Example 3). These labeling results show that the biosynthesis of dihydrosterculic acid is through the addition a methylene group to the oleic acid across the double bond. The methylene group is derived from methionine, most likely through S-adenosyl-methionine. In summary, these data clearly confirm that the identified *Sterculia* gene encodes a protein which functions as a cyclopropane synthase.

Although it is not necessary to understand the mechanism to practice the present invention, and the invention is not intended to be limited to any particular mechanism, the following discussion of CPA-FAS and its protein structure and proposed and hypothetical functions provides further insight into the biology of the newly discovered protein. So far, one cyclopropane synthase from *Escherichia coli* (Wang et al (1992) Biochem 31 (45): 11020-11028) and three (cma1, cma2, and mma2) closely related from mycobacterial (George et al. (1995) J Biol Chem 270 (45): 27292-27298; and Yuan and Barry (1995) Proc Nat'l Acad Sci USA 92 (14): 6630-6634) have been functionally proven to catalyze the transfer of a methylene group from S-adenosyl-L-methionine to the double bond of certain fatty acid. The *Sterculia* CPA-FAS reported here is the first enzyme of this kind that has been isolated from plants. Another set of genes (mma1, mma3, and mma4) of mycobacteria is also highly homologous to *E. coli* CFA synthase. But these enzymes convert a double bond to one of several structures (Yuan et al. (1997) J. Biol. Chem. 272: 10041-10049), namely an alpha-methyl-branched trans-olefin —CH(CH3)CH:CH— (mmas-1) or an alpha-hydroxymethyl (mmas-4) —CH(OH)CH(CH3)—. The alpha-hydroxymethyl structure can be converted to an alpha-methoxymethyl group —CH(OCH3)CH(CH3)— by addition of another methylene group, this time to the hydroxyl oxygene atom and not to an unsaturated carbon atom. Furthermore 10-methylstearate, or tuberculostearate, is a well known fatty acid of mycobacteria and is produced by a 10-methylene stearate intermediate. The mechanistic similarities of these reactions are described by Grogan and Cronan (1997, Microbiol. Mol. Biol. Rev. 61: 429-441). They are readily understood at the chemical level because the intermediate carbocation formed by addition of the methyl group from S-adenosyl-methionine can readily rearrange, such that small changes in the active site configuration can result in different structures of products.

A comparison of the amino acid sequence of *Sterculia* CPA-FAS with other CPA-FASs and the related methoxy mycolic acid synthases is shown in FIG. 10(A). All the bacterial amino acid sequences are about half the size of *Sterculia* cyclopropane synthase and share significant degree of similarity with the carboxy terminus of *Sterculia* gene. The proposed S-adenosyl-methionine binding motif (amino acid residues 171-179, using the *E. coli* numbering, and amino residues 627-635 in the *Sterculia* enzyme) and the catalytically important cysteine 354 (amino residue 822 in the *Sterculia* enzyme) are absolutely conserved for all the proteins. FIG. 10(B) shows the phylogenetic relationship among these enzymes. The *Sterculia* and *E. coli* enzymes are more closely related to each other than to those enzymes from mycobacteria, which might reflect the fact that both enzymes act on monounsaturated fatty acids esterified to phospholipids (Ohlrogge et al. (1976) Biochim. Biophys. Acta 431: 257-267). However, the fact that a highly related set of microbial genes encode a series of different methylene-added fatty acid synthases suggests that the plant CPA-FAS gene could be modified to produce an equal diversity of products, thus enhancing its utility.

The amino terminal portion of the *Sterculia* CPA-FAS polypeptide (amino acids 1-438) is unique to the *Sterculia* cyclopropane synthase, in that no other known cyclopropane synthases possess this portion. It also does not share a significant similarity with any known proteins. However, the N-terminal half of *Sterculia* cyclopropane synthase shares significant homology with Arabidopsis gene At3g23500, and to a lesser extent with At3g23520. These putative genes encode products tentatively identified as tryptophan 2-monooxygenases. Tryptophan 2-monooxygenases belong to a flavin-containing group of oxidases. The tryptophan 2-monooxygenase (IaaM) gene product itself produces indole acetamide, which can be converted to the auxin indole acetic acid by hydrolysis. Most of flavin-containing proteins have a highly conserved motif located the N-terminus of the protein and involved in binding of the ADP moiety of FAD (Eggink et al., 1990; Eberhardt et al., 1996; Haigler et al., 1996). The proposed motif (G-X-G-X-X-G-X-X-X-A (SEQ ID NO:25)) is preceded by 3 or 4 hydrophobic residues (Russel, M and Model, P (1988) J. Biol. Chem. 263: 9015-9019.). The conserved FAD binding motif is present in the first 15 amino acid of *Sterculia* cyclopropane synthase (MGVAV-IGGGIQGLVSAYVLAKAGVNVVVYE (SEQ ID NO:2). Since the mechanism of the cyclopropane ring formation is believed to proceed via a carbocation mechanism, with the proposed intermediate (-CHCH$_3$—CH$^+$—) formed by addition of the methyl group from S-adenosylmethionine, it is unlikely that a redox system such as a FAD-containing protein is involved in the catalytic reaction of methylene addition. Therefore, it is unlikely that the amino terminal portion of the *Sterculia* CPA-FAS is involved in cyclopropane ring formation. It appears that the CPA-FA synthase polypeptide contains a fused redox protein at its amino terminus (approximately amino acids 1-438), which is probably an oxidase. It is contemplated that the redox protein domain functions either in the desaturation of dihydrosterculic acid to sterculic acid, or more likely in the ∀-oxidation that accompanies the formation of sterculic acid.

It is believed that dihydrosterculic acid is converted to sterculic acid by desaturation (FIG. 1). In labeling studies with developing *Sterculia* seed tissue, added [$^{14}$C]stearolate, the 9,10-acetylenic analog of oleate, was not converted to [$^{14}$C]sterculate. On the other hand, dihydrosterculate was clearly desaturated to sterculate, but the conversion rates were slow. Nonetheless, taken together, these data support the proposed pathway for the synthesis of sterculic acid by desaturation of dihydrosterculic acid. However, an unusual feature associated with sterculic acid biosynthesis in both seeds and other plant tissues is substantial ∀-oxidation. Often malvalic acid is the major CPE-FA. Although other non-carbocyclic fatty acids show a small amount of ∀-oxidation products, the CPE-FA are often chain-shortened to a much greater proportion. Such extensive ∀-oxidation seems unique to CPE-FA biosynthesis. However, in the tobacco cell lines transformed with the coding sequence for *Sterculia* CPA-FAS, no 17- or 18-carbon CPA-FAs were found in any independent transgenic tobacco cell line screened. The lack of 17 carbon CPA-FAs is thought to be due to the lack of 16:1 substrate. The lack of 18 carbon CPA-FAs is an indication that the *Sterculia* CPA-FAS did not induce ∀-oxidation, despite the presence of the apparent redox fusion protein, which is contemplated to be involved in ∀-oxidation. However, it is contemplated that the substrate of ∀-oxidation is the unsaturated CPE-FA, rather than the saturated CPA-FA. Support is provided by the observation that in Litchi, the only seed known where CPA-FAs accumulate without CPE-FA, there are no ∀-oxidation products of dihydrosterculic acid (though traces of 17- and 5-carbon ∃-oxidation products are seen; Gaydou et al. (1993) J. Agric. Food Chem. 41: 886-890).

Thus, it is contemplated that the *Sterculia* CPA-FAS comprises a natural fusion product of two catalytic activities; one catalyzes the cyclopropane fatty acid synthesis (the carboxy terminal, at about amino acids 439-864), and the other catalyzes an ∀-oxidation shortening of a fatty acid with a cyclic carbon functional group, most likely an unsaturated cyclic carbon ring or a cyclopropene ring (the amino terminal, at about amino acids 1-438). Examples of fusion proteins, and in particular of fusion of proteins involved in lipid synthesis, are known (for example, a single polypeptide with two enzymatic activities was reported to occur naturally in coral, where a fusion protein contains both lipoxygenase and allene oxide synthase (Koljak et al. (1997) Science 277: 1994-1996; Boutand and Brash (1999) J. Biol. Chem. 274: 33764-33770)

The *Sterculia* CPA-FAS is the first confirmed identification of a plant CPA-FAS, despite one recent report of the putative identification of plant nucleic acid sequences which purportedly encode cyclopropane synthetase (or CFA synthase) (WO 99/43827). The application describes nucleic acid fragments reportedly encoding at least a portion of several cyclopropane synthetases; these fragments were isolated and identified by comparison of random plant cDNA sequences to public databases containing nucleotide and protein sequences using BLAST algorithms. The encoded proteins were discovered based upon their similarity to cyclopropane synthetase from *Mycobacterium tuberculosis* or from *E. coli*. The results are a set of five nucleotide sequences, one of which is a contig from corn (assembled from three clones), the next three of which are clones from *Phaseolus*, rice and soybean, and the last of which is a contig from wheat (assembled from two clones); only the first two sequences appear to encode a "complete" protein of about 386 amino acids. The first "complete" protein is described as containing a signal sequence of amino acids 1-28 (though how this signal sequence was identified was not described) and a mature protein of amino acids 29-386. The *E. coli* CFA synthase amino acid sequence is also described as 19.95% and 19.2% similar to the two "complete" proteins, respectively. The application does not provide any evidence that the sequences in fact encode a plant CPA-FAS, other than the homology the amino acid sequences (as predicted from the nucleic acid sequences) exhibit to the bacterial enzymes.

However, it appears that WO 99/43827 describes nucleic acid sequences which do not actually encode plant CFA synthases. This is based upon several lines of reasoning. First, the predicted amino acid sequence of the *Sterculia* CFA synthase is 864 amino acids long, or more than twice as long as the "complete" proteins described in WO 99/43827. The amino acid sequence of the *Sterculia* enzyme appears to have a higher degree of homology to the *E. coli* sequence, at the region of overlap, than do the "complete" sequences described WO 99/43827. The present inventors have provided evidence in Example 3 that transformation of the *Sterculia* nucleic acid sequence into yeast and plant cells results in the production of CPA-FAs in a tissue which does not normally have such fatty acids; this is in contrast to WO 99/43827, which does not provide any evidence at all that expression of such sequences can result in the appearance of CPA-FAs. The source from which the *Sterculia* nucleic acid sequence was isolated was predicted to be an abundant source of the enzyme, based upon the presence of CPE-FAs of up to 60% in *sterculia* seed oil, and based upon the assumption that CPE-FAs are derived from CPA-FAs. This is in contrast to the sources from which the cDNA libraries were prepared in WO 99/43827, which were corn, *Phaseolus*, rice, soybean, and wheat, and which are not known to contain CPA-FAs. Finally, there are many S-adenosyl methionine dependent methyl transferases with similar DNA and protein sequences (as described, for example, in Wang et al. (1992) Biochemistry 31: 11020-11028). Therefore sequence similarity alone is not sufficient to demonstrate protein function and identity.

However, the *Sterculia* CPA-FAS amino acid sequence can be used to discover other plant CPA-FASs, as is described further below; in one embodiment, coding sequences for cotton CPA-FAS are discovered by the methods described below, and as is described in further detail in Example 5.

A. Plant Cyclopropane Fatty Acid Synthase Genes

The present invention provides compositions comprising isolated nucleic acid sequences encoding plant CPA-FAS. In some embodiments, the sequences encode a Malvaceae CPA-FAS; in other embodiments, the sequences encode a *Sterculia* CPA-FAS; in yet other embodiments, the sequences encode a cotton CPA-FAS. In some embodiments, the sequences comprise the sequence shown in FIG. 4 (SEQ ID NO: 1); in other embodiments, the sequences encode the amino acid sequence shown in FIG. 5 (SEQ ID NO:2). In yet other embodiments, the sequences comprise at least one of the sequences shown in FIGS. 14 and 15 (SEQ ID NOs:3, 4, 5, and 6); in other embodiments, the sequences encode at least one of the amino acid sequences shown in FIG. 16 (SEQ ID NOs:7, 8, 9, and 10). In preferred embodiments, the CPA-FAS encoded by the nucleic acid sequences of the invention are functional, or possess CPA-FAS activity.

In yet other embodiments, the present invention provides compositions comprising isolated nucleic acid sequences which encode a portion of a plant CPA-FAS which retains some functional characteristic of a CPA-FAS. Examples of functional characteristics include the ability to act as an immunogen to produce an antibody which recognizes a CPA-FAS (see, for example, Example 4); in particular embodiments, the nucleic acid sequences encode the amino acid sequence shown in FIG. 13 (SEQ ID NO: 11) Other examples include nucleic acid sequences which encode either the amino terminal or the carboxy terminal of a plant CPA-FAS, which are hypothesized to possess separate and distinct enzymatic capabilities; in these embodiments, the nucleic acid sequences encode either the amino terminal of a plant CPA-FAS (which in *Sterculia* is about amino acids 1-438) or the carboxy terminal of a plant CPA-FAS (which in *Sterculia* is about amino acids 439-864); in particular embodiments, these protein fragments retain the enzymatic activity associated with it in the native or complete CPA-FAS protein. In other particular embodiments, the nucleic acid fragments encode SEQ ID NOs:7, 8, 9, or 10.

In yet other embodiments, the present invention provides compositions comprising isolated nucleic acid sequences encoding a plant CPA-FAS, where the encoded CPA-FAS comprises at least one fragment of SEQ ID NOs:2, 7, 8, 9, or 10, and wherein the encoded CPA-FAS is cross-reactive with an antibody against a *Sterculia* CPA-FAS and is about the same size as a *Sterculia* CPA-FAS (about 864 amino acids long). An exemplary antibody to CPA-FAS is described in Example 4. The range of sizes of a *Sterculia* CPA-FAS is from about 800-900 amino acids long. A fragment of an amino acid sequence comprises at least 10, more preferably 20, even more preferably 30, and most preferably 40 or more amino acid residues present anywhere within the amino acid sequence. Alternatively, a fragment comprises at least 20, more preferably about 30, even more preferably about 40, and most preferably about 50 or more amino acid residues present anywhere within the amino acid sequence, wherein the fragment further comprises at least one amino acid deletion or addition or substitution, where the number of total amino acid additions, deletions, or substitutions in any one fragment comprise up to about 10% of the total number of amino acids in the fragment. If more than one amino acid deletion, addition, or substitution exist, they may be contiguous or non-contiguous. Preferably, amino acid substitutions are conservative.

B. Plant Cyclopropane Fatty Acid Synthase Polypeptides

The present invention provides compositions comprising purified plant CPA-FAS polypeptides as well as compositions comprising variants, including homologs, mutants or fragments, or fusion proteins thereof. In some embodiments, the polypeptide comprises a Malvaceae CPA-FAS; in other embodiments, the polypeptide comprises a *Sterculia* CPA-FAS; in yet other embodiments, the polypeptide comprises a cotton CPA-FAS. In one embodiment, the polypeptide is encoded by the sequence shown in FIG. 4 (SEQ ID NO: 1); in other embodiments, the polypeptide comprises the amino acid sequence shown in FIG. 5 (SEQ ID NO:2). In other embodiments, the polypeptide is encoded by a sequence comprising at least one of the sequences shown in FIGS. 14 and 15 (SEQ ID NOs:3, 4, and 6); in other embodiments, the polypeptide comprises at least one of the amino acid sequences shown in FIG. 16 (SEQ ID NOs:7 and 8).

The polypeptide catalyzes the addition of a methylene group across the unsaturated center of an unsaturated fatty acid, and includes the addition of a methylene group across a double bond of an acyl group. Thus, a plant CPA-FAS of the present invention is a polypeptide with the capacity to synthesize a fatty acid containing a cyclopropane ring.

Thus, plant CPA-FAS catalyzes the following reaction:

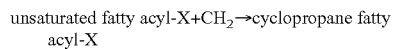

unsaturated fatty acyl-X+CH$_2$→cyclopropane fatty acyl-X where X is preferably a glycerolipid, and most likely a phospholipid, such as phosphatidylcholine. The enzyme in situ most likely acts on a fatty acid such as oleic or palmitoleic acid esterified to a lipid, and uses S-adenosyl methionine (SAM) as a methyl donor. Moreover, the enzyme may utilize different substrates under different conditions to differing degrees of activity, and may produce other substrates as well. Thus, other substrates may accept a methylene group, and the resulting fatty acyl group may have an unsaturated carbocyclic ring.

In some embodiments of the present invention, the polypeptide is a purified product, obtained from expression of a native gene in a cell, while in other embodiments it may be a product of chemical synthetic procedures, and in still other embodiments it may be produced by recombinant techniques using a prokaryotic or eukaryotic host (for example, by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

Assay of Plant Cyclopropane Fatty Acid Synthase

The activity of plant CPA-FAS may be assayed in a number of ways. In one aspect, the activity is determined by expressing a nucleic acid sequence encoding the synthase in a transgenic organism and then analyzing the composition of the total fatty acids. Thus, the activity is measured as the presence of or increase in the amount of endogenous cyclopropane fatty acid in a transgenic organism which comprises an exogenous nucleic acid sequence comprising SEQ ID NO: 1 or encoding a polypeptide comprising the amino acid sequence shown in SEQ ID NO:2; such transgenic organisms are obtained as described elsewhere The amount of cyclopropane fatty acid in a transgenic organism is compared to that present in a non-transgenic organism. The fatty acids are typically analyzed from lipids extracted from samples of a transgenic organism; the samples are homogenized in methanol/chloroform (2:1, v/v) and the lipids extracted as described by Bligh and Dyer (1959).

In another aspect, the enzyme activity is determined in tissue samples obtained from a organism which may or may not be transgenic. For example, in plants, tissue samples include but are not limited to leaf samples (such as discs), stem and root samples, and developing and mature seed embryonic or endosperm tissue. Typically, tissue samples are incubated with either precursors of fatty acid synthesis, such as $^{14}$C-acetate, or with fatty acid substrates, such as ammonium salts of $^{14}$C-fatty acids, which can be taken up and incorporated into tissue lipids, or with labeled substrates, such as $^{14}$C-methionine. Additional co-factors for lipid synthesis, as required, are present during the incubation; such co-factors include but are not limited to ATP, CoA, $Mgl_2$, and SAM. Alternatively, tissue samples are incubated with labeled SAM: Incubations generally proceed at room temperature in a buffered solution, such as 0.1M potassium phosphate at pH 7.2, for a suitable period of time. The samples are then washed in buffer, and the tissue samples homogenized in methanol/chloroform (2:1, v/v) and the lipids extracted as described by Bligh and Dyer (1959).

In another aspect, the enzyme activity is determined in a sub-cellular fraction obtained from an organism which may or may not be transgenic (transgenic organisms are described elsewhere), where the tissue is disrupted to result in cell-free fractions. For example, in plants, subcellular fractions may be obtained from any of the types of tissues described above, and include whole cell and microsomal membranes, plastids, and plastidial membrane fractions. Preparation of such fractions are well-known in the art. The subcellular fraction is then incubated with fatty acids, such as ammonium salts of $^{14}$C-fatty acids, which can be taken up and incorporated into tissue lipids. Alternatively, the subcellular fraction is incubated with labeled SAM. Additional co-factors for lipid synthesis, as required, are present during the incubation; such co-factors include but are not limited to ATP, CoA, $MgCl_2$, lyso-phospholipids, such as lysoPC, and SAM. Other reagents which may enhance lipid synthesis may also be added; such reagents include phospholipid liposomes (for example, containing phosphatidylcholine) and lipid transfer proteins. The samples are incubated and the lipids extracted as described above.

In another aspect, the enzyme activity is determined from an in-vitro nucleic acid expression system, in which a nucleic acid sequence comprising SEQ ID NO: 1 or encoding a polypeptide comprising the amino acid sequence shown in SEQ ID NO:2 is added and the encoded enzyme expressed. Such expression systems are well-known in the art, for example reticulocyte lysate or wheat germ. Because the enzyme is likely to be an unstable protein which is stabilized by the presence of glycerolipids, micellar or membrane structures are included in the mixture into which the enzyme may be incorporated during or after protein synthesis. Moreover, because the enzyme in situ is likely to act on a fatty acid esterified to a lipid, it is preferable that such micellar structures are obtained from sources which contain related lipid synthetic capabilities, such as from microsomes from plant tissues where the plant does not contain an endogenous cyclopropane fatty acid synthase but which does possess the ability to incorporate a labeled fatty acid substrate into a glycerolipid. Direct and quantitative measurements require the incorporation of labeled lipids into the micellar or membrane structures and the assurance that the incorporation of a fatty acid substrate is not limiting. The newly-expressed enzyme is then analyzed as described above for subcellular fractions.

The extracted lipid products of the plant CPA-FAS are analyzed by methods well-known in the art. For example, fatty acid methyl esters are prepared from an aliquot of the extracted lipid fraction by evaporating the solvent from the aliquot under $N_2$, and resuspending the lipids in equal volumes of 1% sodium methoxide in methanol (w/w) and heptane. Cyclopropane and cyclopropene groups in fatty acids are disrupted by acidic conditions, and lipid samples containing such acids are best transesterified with basic reagents; the free fatty acids can be methylated safely with diazomethane (Christie (1982) in Lipid Analysis, 2nd Ed., p 55). The fatty acid methyl esters are then extracted into hexane and separated, and for radioactive samples the radioactivity in each separated fraction determined, by TLC, GC, or GC/MS (see, for example, described in Example 1).

Purification of Plant Cyclopropane Fatty Acid Synthase

In some embodiments of the present invention, a plant CPA-FAS polypeptide purified from organisms is provided; such organisms may be transgenic organism, comprising a heterologous plant CPA-FAS gene. The present invention provides a purified plant CPA-FAS polypeptide as well as a variant, homolog, mutant or fusion protein thereof, as described elsewhere.

The present invention also provides methods for recovering and purifying plant CPA-FAS from an organism; such organisms include single and multi-cellular organisms. Typically, the cells are first disrupted and fractionated before subsequent enzyme purification; disruption and fractionation methods are well-known. Purification methods are also well-known, and include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

It is anticipated that plant CPA-FAS is unstable, by analogy with *E. coli* cyclopropane fatty acid synthase (CFA synthase) (Grogan, D W and Cronan, J W Jr. (1997) Microbiol Molec Biol Reviews 61(4): 429-441). The *E. coli* enzyme is extremely unstable, such that when crude extracts of *E. coli* were freed of endogenous lipid by ultracentrifugation, less than 1% of the initial CFA synthase activity remained after a 30-min incubation at 30"C, and that this instability has severely hampered purification and detailed studies of the enzyme. It was noted that the enzyme associates reversibly with membrane fragments and with phospholipid vesicles, and that this association is the only generally effective means of stabilizing CFA synthase identified at the time the reference was published. Therefore, it is contemplated that in one embodiment, a plant CPA-FAS of the present invention is purified as described for bacterial CFA synthase (Grogan, D W and Cronan, J W Jr. (1997) Microbiol Molec Biol Reviews 61(4): 429-441). This scheme involves disruption of cells (as for example by passage through a French press or by homogenization), centrifugation at high speeds to remove cellular debris (as for example at 150,000 g for about 2 hours), precipitation of protein from the resulting supernatant, as for example by adding ammonium sulfate to about 40% saturation, collecting the precipitated protein by centrifugation (as for example at 10,000 g for about 15 min), removal of residual ammonium sulfate from the resuspended protein pellet (as for example by gel filtration), and liposome flotation of the enzyme and subsequent purification of the lipid layer by sucrose gradient centrifugation.

The present invention further provides nucleic acid sequences having a coding sequence of the present invention (for example, SEQ ID NO: 1) fused in frame to a marker sequence that allows for expression alone or both expression and purification of the polypeptide of the present invention. A non-limiting example of a marker sequence is a hexahistidine tag that may be supplied by a vector, for example, a pQE-30 vector which adds a hexahistidine tag to the N terminal of a plant CPA-FAS and which results in expression of the polypeptide in the case of a bacterial host, and more preferably by vector PT-23B, which adds a hexahistidine tag to the C terminal of a plant CPA-FAS and which results in improved ease of purification of the polypeptide fused to the marker in the case of a bacterial host, or, for example, the marker sequence may be a hemagglutinin (HA) tag when a mammalian host is used. The HA tag corresponds to an epitope derived from the influenza hemagglutinin protein (Wilson et al. (1984) Cell, 37:767).

Chemical Synthesis of Plant Cyclopropane Fatty Acid Synthase

In an alternate embodiment of the invention, the coding sequence of a plant CPA-FAS is synthesized, whole or in part, using chemical methods well known in the art (See for example, Caruthers et al. (1980) Nucl. Acids Res. Symp. Ser., 7:215-233; Crea and Horn (1980) Nucl. Acids Res., 9:2331; Matteucci and Caruthers (1980) Tetrahedron Lett., 21:719; and Chow and Kempe (1981) Nucl. Acids Res., 9:2807-2817). In other embodiments of the present invention, the protein itself is produced using chemical methods to synthesize either an entire plant CPA-FAS amino acid sequence or a portion thereof. For example, peptides are synthesized by solid phase techniques, cleaved from the resin, and purified by preparative high performance liquid chromatography (See for example, Creighton (1983) *Proteins Structures And Molecular Principles*, W H Freeman and Co, New York N.Y.). In other embodiments of the present invention, the composition of the synthetic peptides is confirmed by amino acid analysis or sequencing (See for example, Creighton, supra).

Direct peptide synthesis can be performed using various solid-phase techniques (Roberge et al. (1995) Science, 269: 202-204) and automated synthesis may be achieved, for example, using ABI 431A Peptide Synthesizer (Perkin Elmer) in accordance with the instructions provided by the manufacturer. Additionally, an amino acid sequence of a plant CPA-FAS, or any part thereof, may be altered during direct synthesis and/or combined using chemical methods with other sequences to produce a variant polypeptide.

Generation of Plant Cyclopropane Fatty Acid Synthase Antibodies

In some embodiments of the present invention, antibodies are generated to allow for the detection and characterization of a plant CPA-FAS protein. The antibodies may be prepared using various immunogens. In one embodiment, the immunogen is a *Sterculia* CPA-FAS peptide (for example, an amino acid sequence as depicted in SEQ ID NO:2, or fragments thereof) to generate antibodies that recognize *Sterculia* CPA-FAS. Such antibodies include, but are not limited to polyclonal, monoclonal, chimeric, single chain, Fab fragments, and Fab expression libraries.

Various procedures known in the art may be used for the production of polyclonal antibodies directed against a plant CPA-PAS. For the production of antibody, various host animals can be immunized by injection with the peptide corresponding to a plant CPA-FAS epitope including but not limited to rabbits, mice, rats, sheep, goats, etc. In a preferred embodiment, the peptide is conjugated to an immunogenic carrier (for example, diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (for example, aluminum hydroxide), surface active substances (for example, lysolecithin, pluronic polyols, polyanions, peptides, oil emulsions, keyhole limpet hemocyanins, dinitrophenol, and potentially useful human adjuvants such as BCG (Bacille Calmette-Guerin) and Corynebacterium parvum).

For preparation of monoclonal antibodies directed toward a plant CPA-FAS, it is contemplated that any technique that provides for the production of antibody molecules by continuous cell lines in culture finds use with the present invention (See for example, Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein (1975) Nature,256: 495-497), as well as the trioma technique, the human B-cell hybridoma technique (See for example, Kozbor et al. (1983) Immunol. Tod., 4:72), and the EBV-hybridoma technique to produce human monoclonal antibodies (Cole et al. (1985) in *Monoclonal Antibodies and Cancer Therapy*, Alan R. Liss, Inc., pp. 77-96).

In addition, it is contemplated that techniques described for the production of single chain antibodies (U.S. Pat. No. 4,946, 778) find use in producing a plant CPA-FAS-specific single chain antibodies. An additional embodiment of the invention utilizes the techniques described for the construction of Fab expression libraries (Huse et al. (1989) Science, 246:1275-1281) to allow rapid and easy identification of monoclonal Fab fragments with the desired specificity for a plant CPA-FAS.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (for example, radioimmunoassay, ELISA (enzyme-linked immunosorbant assay), "sandwich" immunoassays, immunoradiometric assays, gel diffusion precipitin reactions, immunodiffusion assays, in situ immunoassays (for example, using colloidal gold, enzyme or radio-isotope labels, for example), Western blots, precipitation reactions, agglutination assays (for example, gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In some embodiments of the present invention, the foregoing antibodies are used in methods known in the art relating to the expression of plant CPA-FAS (for example, for Western blotting), measuring levels thereof in appropriate biological samples, etc. The antibodies can be used to detect plant CPA-FAS in a biological sample from a plant. The biological sample can be an extract of a tissue, or a sample fixed for microscopic examination.

The biological samples are then be tested directly for the presence of plant CPA-FAS using an appropriate strategy (for example, ELISA or radioimmunoassay) and format (for example, microwells, dipstick (for example, as described in International Patent Publication WO 93/03367), etc. Alternatively, proteins in the sample can be size separated (for example, by polyacrylamide gel electrophoresis (PAGE), in the presence or not of sodium dodecyl sulfate (SDS), and the presence of plant CPA-FAS detected by immunoblotting (Western blotting). Immunoblotting techniques are generally more effective with antibodies generated against a peptide corresponding to an epitope of a protein, and hence, are particularly suited to the present invention.

II. Methods of Identifying Plant CPA-FAS Genes and Related Plant Genes

Some embodiments of the present invention contemplate methods to isolate nucleic acid sequences encoding plant CPA-FAS, based upon the hypothesis that the presence of CPA-FAs and/or CPE-FAs in plant tissue, preferably seed tissue, is indicative of the presence of CPA-FAS. The methods involve first preparation of a cDNA library from tissue in which CPA-FAs or CPE-FAs are produced to relatively high levels. The methods involve next subtracting highly abundant sequences from the library, sequencing the remaining library clones, and comparing the encoded amino acid sequences to the amino acid sequence of either *E. coli* CPA-FAS or *Sterculia* CPA-FAS to select putative CPA-FAS candidate ESTs. The methods involve next assembling a clone encoding a complete putative plant CPA-FAS, and characterizing the expression products of such sequences so discovered.

Alternatively, the methods involve first an examination of a plant expressed sequence tag (EST) database, in order to discover novel potential CPA-FAS encoding sequences. Preferably, the plant source of the EST database comprises CPA-FAs and/or CPE-FAs in its plant tissue, such as its seed tissue. In some embodiments, examination of a plant EST database involves blasting the database with the amino acid sequence of the *Sterculia* CPA-FAS (for example, SEQ ID NO:2), in order to discover ESTs encoding amino acid sequences with homology to the *Sterculia* CPA-FAS protein. In some further embodiments, the methods involve next assembling a clone encoding a complete putative plant CPA-FAS, and characterizing the expression products of such sequences so discovered. In other further embodiments, these methods next involve sequencing likely candidate sequences, and characterizing the expression products of such sequences so discovered.

Employing these methods resulted in the discovery of a *Sterculia* CPA-FAS, as described in illustrative Examples. The isolated novel coding sequence was demonstrated to encode plant cyclopropane fatty acid synthase, as described in the illustrative Examples. It is contemplated that these methods can also be used to discover other CPA-FASs from plants which are known to possess CPA-FAs and CPE-FAs. Exemplary plants include those from the families Malvaceae, sterculiaceae, Bombaceae, Tilaceae, Mimosaceae and Sapindaceae. In particular, it is contemplated that a CPA-FAS from cotton is identified and isolated by these methods. Thus, employing these methods resulted in the discovery of cotton CPA-FAS coding sequences, as described in illustrative Examples. Cotton tissues were demonstrated to contain cyclopropane and cyclopropene fatty acids (CPA-FAs and CPE-FAs), where certain tissues (such as root and stem) contained relatively high levels of these fatty acids (up to about 30% and about 35%, respectively). Moreover, cotton tissues were demonstrated to contain a protein which cross-reacts with antibody prepared to the *Sterculia* CPA-FAS, where the protein is about the same size as the *Sterculia* CPA-FAS, and where the protein has a tissue distribution which generally corresponds to the amounts of CPA-FAs and CPE-FAs present in the tissues.

The nucleotide sequence encoding the *Sterculia* CPA-FAS, and the deduced amino acid sequence of the *Sterculia* CPA-FAS, are shown in FIG. 4 (SEQ ID NOs 1 and 2, respectively). The *Sterculia* CPA-FAS coding sequence can be used to locate and isolate the *Sterculia* CPA-FAS genes, by methods well known in the art; thus, plant CPA-FAS coding sequences, discovered by the methods of the present invention, can also be used to locate and isolate other plant genes by these same methods. To isolate the gene, a $^{32}$P-radiolabeled CPA-FAS coding sequence (or cDNA) is used to screen, by DNA-DNA hybridization, a genomic or cDNA library constructed from *Sterculia* genomic DNA. Single isolated clones that test positive for hybridization are proposed to contain part or all of the CPA-FAS gene, and are sequenced. The sequence of these positive cloned *Sterculia* genomic DNA is used to confirm the identity of the gene as a plant CPA-FAS. If a particular clone encodes only part of the gene, additional clones that test positive for hybridization to the CPA-FAS coding sequence (or cDNA) are isolated and sequenced. Comparison of the full-length sequence of the CPA-FAS gene to the cDNA are used to determine the location of introns, if they are present.

The *Sterculia* CPA-FAS can also be used to identify and isolate related plant genes. As an example, it is believed that CPE-FA is synthesized via desaturation of CPA-FA. Although tobacco cell lines transformed with *Sterculia* CPA-FAS produce CPA-FA (dihydrosterculic acid), they do not appear to produce CPE-FA (sterculic acid). Therefore, it appears that the identified *Sterculia* CPA-FAS does not desaturate CPA-FA to CPE-FA, and that another *Sterculia* polypeptide is responsible for desaturating CPA-FA. A nucleic acid sequence for this activity is identified and isolated according to the methods described above for identifying CPA-FAS coding sequences, except that desaturase amino acid sequences are used as the basis for homology comparisons. It is contemplated that the desaturase is homologous to a FAD2 or a P450 enzyme. Candidate sequences are then co-transformed into tobacco cell lines already transformed with *Sterculia* CPA-FAS, as for example is described in the Examples, and the fatty acid products analyzed, as for example is described in the Examples. The presence of CPE-FA in the transgenic cell lines confirms that the candidate sequence is a CPA-FA desaturase.

III. Additional Plant Cyclopropane Fatty Acid Synthase Genes

The present invention provides isolated nucleic acid sequences encoding a plant CPA-FAS. For example, some embodiments of the present invention provide isolated polynucleotide sequences that are capable of hybridizing to SEQ ID NOs: 1, 3, and/or 6 under conditions of low to high stringency as long as the polynucleotide sequence capable of hybridizing encodes a protein that retains a desired biological activity of a plant CPA-FAS. In preferred embodiments, hybridization conditions are based on the melting temperature ($T_m$) of the nucleic acid binding complex and confer a defined "stringency" as explained above (See for example, Wahl et al. (1987) Meth. Enzymol., 152:399-407, incorporated herein by reference).

In other embodiments, an isolated nucleic acid sequence encoding a plant CPA-FAS which is homologous to the *Sterculia* CPA-FAS is provided; in some embodiments, the sequence is obtained from a plant from the family Malvaceae, sterculiaceae, Bombaceae, Tilaceae, Mimosaceae or Sapindaceae. In particular embodiments, such sequences are obtained from cotton; these sequences comprise at least one of SEQ ID NOs:3, 4 and 6.

In other embodiments of the present invention, alleles of a plant CPA-FAS are provided. In preferred embodiments, alleles result from a mutation, (in other words, a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In other embodiments of the present invention, the polynucleotide sequence encoding a plant CPA-FAS is extended utilizing the nucleotide sequences for example, SEQ ID NO: 1) in various methods known in the art to detect upstream sequences such as promoters and regulatory elements. For example, it is contemplated that polymerase chain reaction (PCR) finds use in the present invention. This is a direct method that uses universal primers to retrieve unknown sequence adjacent to a known locus (Gobinda et al. (1993) PCR Methods Applic., 2:318-322). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia et al (1988) Nucleic Acids Res., 16:8186). The primers may be designed using Oligo 4.0 (National Biosciences Inc, Plymouth Minn.), or another appropriate program, to be, for example, 22-30 nucleotides in length, to have a GC content of 50% or more, and to anneal to the target sequence at temperatures about 68-72 EC. The method uses several restriction enzymes to generate a suitable fragment in the known region of a gene. The fragment is then circularized by intramolecular ligation and used as a PCR template. In yet another embodiment of the present invention, capture PCR (Lagerstrom et al. (1991) PCR Methods Applic., 1:111-119) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking that permits retrieval of unknown sequence (Parker et al. (1991) Nucleic Acids Res., 19:3055-60). The PROMOTERFINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (Lui and Whittier, (1995); Lui et al. (1995)).

Preferred libraries for screening for full length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

IV. Variant Plant Cyclopropane Fatty Acid Synthases

In some embodiments, the present invention provides isolated variants of the disclosed nucleic acid sequence encoding plant CPA-FAS, and the polypeptides encoded thereby; these variants include mutants, fragments, fusion proteins or functional equivalents of plant CPA-FAS. Thus, nucleotide sequences of the present invention are engineered in order to alter a plant CPA-FAS coding sequence for a variety of reasons, including but not limited to alterations that modify the cloning, processing and/or expression of the gene product (such alterations include inserting new restriction sites, altering glycosylation patterns, and changing codon preference) as well as varying the enzymatic activity (such changes include but are not limited to differing substrate affinities, differing substrate preferences and utilization, differing inhibitor affinities or effectiveness, differing reaction kinetics, varying subcellular localization, and varying protein processing and/or stability). For example, mutations are introduced which alter the substrate specificity, such that the preferred substrate is changed.

In other embodiments, the present invention provides isolated nucleic acid sequences encoding a plant CPA-FAS, where the encoded synthase competes for binding to an unsaturated fatty acid substrate with a protein comprising the amino acid sequence of SEQ ID NO:2.

Mutants of a Plant Cyclopropane Synthase

Some embodiments of the present invention provide mutant forms of a plant CPA-FAS (in other words, muteins). In preferred embodiments, variants result from mutation, (in other words, a change in the nucleic acid sequence) and generally produce altered mRNAs or polypeptides whose structure or function may or may not be altered. Any given gene may have none, one, or many mutant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that is possible to modify the structure of a peptide having an activity (for example, a plant CPA-FAS activity) for such purposes as increasing synthetic activity or altering the affinity of the plant CPA-FAS for a particular fatty acid substrate. Such modified peptides are considered functional equivalents of peptides having an activity of a plant CPA-FAS as defined herein. A modified peptide can be produced in which the nucleotide sequence encoding the polypeptide has been altered, such as by substitution, deletion, or addition. In some preferred embodiments of the present invention, the alteration increases synthetic activity or alters the affinity of the plant CPA-FAS for a particular fatty acid substrate. In particularly preferred embodiments, these modifications do not significantly reduce the synthetic activity of the modified enzyme. In other words, construct "X" can be evaluated in order to determine whether it is a member of the genus of modified or variant plant CPA-FAS of the present invention as defined functionally, rather than structurally. In preferred embodiments, the activity of variant plant CPA-FAS is evaluated by the methods described in Example 3. Accordingly, in some embodiments the present invention provides nucleic acids encoding a plant CPA-FAS that complement the coding region of SEQ ID NO: 1. In other embodiments, the present invention provides nucleic acids encoding a plant CPA-FAS that compete for the binding of fatty acid substrates with the protein encoded by SEQ ID NO: 1.

In one embodiment, site-specific mutagenesis is performed to modify the catalytic activity of a plant CPA-FAS from a methylene addition across the double bond to a methylene addition at the 10-position, as is known to occur for the synthesis of tubercuolic acid. The modified enzyme will produce fatty acids that have pendant vinyl groups, which is a valuable platform for industrial derivatization. Moreover, hydrogenation of the fatty acid products will give quantitative conversion to methyl-branched saturates.

As described above, mutant forms of a plant CPA-FAS are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (in other words, conservative mutations) will not have a major effect on the biological activity of the resulting molecule. Accordingly, some embodiments of the present invention provide variants of a plant CPA-FAS disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (for example, Stryer ed. (1981) *Biochemistry* pg. 17-21, 2nd ed, WH Freeman and Co.). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (for example, replacement of a glycine with a tryptophan). Analogous minor variations can also include amino acid deletions or insertions, or both. Guidance in determining which amino acid residues can be substituted, inserted, or deleted without abolishing biological activity can be found using computer programs (for example, LASERGENE software, DNASTAR Inc., Madison, Wis.).

Mutants of a plant CPA-FAS can be generated by any suitable method well known in the art, including but not limited to site-directed mutagenesis, randomized "point" mutagenesis, and domain-swap mutagenesis in which portions of the *Sterculia* CPA-FAS cDNA are "swapped" with the analogous portion of other plant or bacterial CPA-FAS-encoding cDNAs (Back and Chappell (1996) PNAS 93: 6841-6845).

Variants may be produced by methods such as directed evolution or other techniques for producing combinatorial libraries of variants. Thus, the present invention further contemplates a method of generating sets of combinatorial mutants of the present plant CPA-FAS proteins, as well as truncation mutants, and is especially useful for identifying potential variant sequences (in other words, homologs) that possess the biological activity of a CPA-FAS (for example, synthesis of CPA-FAs). In addition, screening such combinatorial libraries is used to generate, for example, novel plant CPA-FAS homologs that possess novel substrate specificities or other biological activities all together; examples of substrate specificities are described subsequently.

It is contemplated that the plant CPA-FAS nucleic acids (for example, SEQ ID NO: 1, and fragments and variants thereof) can be utilized as starting nucleic acids for directed evolution. These techniques can be utilized to develop plant CPA-FAS variants having desirable properties such as increased synthetic activity or altered affinity for a particular fatty acid substrate.

In some embodiments, artificial evolution is performed by random mutagenesis (for example, by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech., 14, 458-67; Leung et al. (1989) Technique, 1:11-15; Eckert and Kunkel (1991) PCR Methods Appl., 1:17-24; Caldwell and Joyce (1992) PCR Methods Appl., 2:28-33; and Zhao and Arnold (1997) Nuc. Acids. Res., 25:1307-08). After mutagenesis, the resulting clones are selected for desirable activity (for example, screened for CPA-FAS activity as described subsequently). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (for example, Smith (1994) Nature, 370:324-25; U.S. Pat. Nos. 5,837,458; 5,830,721; 5,811,238; 5,733,731). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences.

Multiple cycles of selection and shuffling have led to the functional enhancement of several enzymes (Stemmer (1994) Nature, 370:398-91; Stemmer (1994) Proc. Natl. Acad. Sci. USA, 91, 10747-10751; Crameri et al. (1996) Nat. Biotech., 14:315-319; Zhang et al. (1997) Proc. Natl. Acad. Sci. USA, 94:4504-09; and Crameri et al. (1997) Nat. Biotech., 15:436-38). Variants produced by directed evolution can be screened for CPA-FAS activity by the methods described subsequently (see Example 3).

Homologs

Still other embodiments of the present invention provide isolated nucleic acid sequence encoding plant CPA-FAS homologs, and the polypeptides encoded thereby. Some homologs of plant CPA-FAS have intracellular half-lives dramatically different than the corresponding wild-type protein. For example, the altered protein are rendered either more stable or less stable to proteolytic degradation or other cellular process that result in destruction of, or otherwise inactivate plant CPA-FAS. Such homologs, and the genes that encode them, can be utilized to alter the activity of plant CPA-FAS by modulating the half-life of the protein. For instance, a short half-life can give rise to more transient plant CPA-FAS biological effects. Other homologs have characteristics which are either similar to wild-type plant CPA-FAS, or which differ in one or more respects from wild-type plant CPA-FAS.

Figure 10:
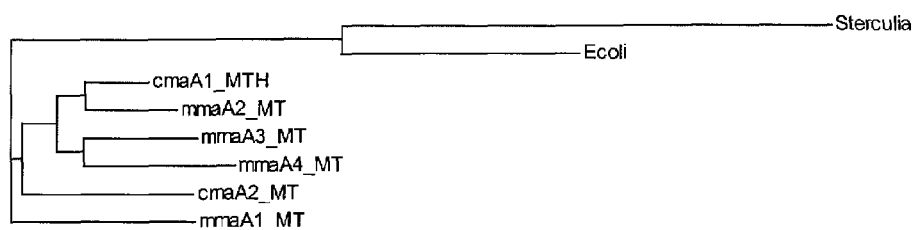
FIG. 10 Panel (A) shows an alignment of the carboxy terminal portion of the *Sterculia* cyclopropane synthase (SEQ ID NO:20) with other cyclopropane synthases and cyclopropane synthase-like enzymes (SEQ ID NOS:12-18). The — line indicates the S-adenosyl-methionine binding site, and the * is the catalytic important Cysteine. Panel (B) shows the phylogenetic relationship among these enzymes.

The cDNA deduced amino acid sequence of *Sterculia* CPA-FAS is compared to the cDNA deduced amino acid sequences of other known bacterial CPA-FAS or CPA-FAS -like proteins, as shown in FIG. 10. The proposed S-adenosyl methionine binding motif (amino acid residues 171-179, using the *E. coli* numbering, and amino residues 627-635 in the *Sterculia* enzyme) and the catalytically important cysteine (amino acid residue 354, using the *E. coli* numbering, and amino residue 822 in the *Sterculia* enzyme) are conserved for all proteins. Accordingly, in some embodiments, the present invention provides a plant CPA-FAS comprising at least the amino acid motif V-L-D-I-G-C-G-W-G (SEQ ID NO:26) (the S-adenosyl methionine binding motif, corresponding to amino acid residues 627-635 in the *Sterculia* enzyme), or the nucleic acid sequences corresponding thereto. In yet other embodiments of the present invention, it is contemplated that nucleic acid sequences suspected of encoding a plant CPA-FAS homolog is screened by comparing motifs. In some embodiments, the deduced amino acid sequence can be analyzed for the presence of the amino acid motif V-L-D-I-G-C-G-W-G (SEQ ID NO:26) (the S-adenosyl methionine binding motif, corresponding to amino acid residues 627-635 in the *Sterculia* enzyme).

In some embodiments of the combinatorial mutagenesis approach of the present invention, the amino acid sequences for a population of plant CPA-FAS homologs are aligned, preferably to promote the highest homology possible. Such a population of variants can include, for example, plant CPA-FAS homologs from one or more species, or plant CPA-FAS homologs from the same species but which differ due to mutation. Amino acids that appear at each position of the aligned sequences are selected to create a degenerate set of combinatorial sequences.

In a preferred embodiment of the present invention, the combinatorial plant CPA-FAS library is produced by way of a degenerate library of genes encoding a library of polypeptides that each include at least a portion of candidate plant CPA-FAS-protein sequences. For example, a mixture of synthetic oligonucleotides is enzymatically ligated into gene sequences such that the degenerate set of candidate plant CPA-FAS sequences are expressible as individual polypeptides, or alternatively, as a set of larger fusion proteins (for example, for phage display) containing the set of plant CPA-FAS sequences therein.

There are many ways by which the library of potential plant CPA-FAS homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential plant CPA-FAS sequences. The synthesis of degenerate oligonucleotides is well known in the art (See for example, Narang (1983) Tetrahedron Lett., 39:3-9; Itakura et al. (1981) Recombinant DNA, in Walton (ed.), Proceedings of the 3rd Cleveland Symposium on Macromolecules, Elsevier, Amsterdam, pp 273-289; Itakura et al. (1984) Annu. Rev. Biochem., 53:323; Itakura et al. (1984) Science 198:1056; Ike et al. (1983) Nucl. Acid Res., 11:477). Such techniques have been employed in the directed evolution of other proteins (See for example, Scott et al. (1980) Science, 249:386-390; Roberts et al. (1992) Proc. Natl. Acad. Sci. USA, 89:2429-2433; Devlin et al. (1990) Science, 249: 404-406; Cwirla et al. (1990) Proc. Natl. Acad. Sci. USA, 87: 6378-6382; as well as U.S. Pat. Nos. 5,223,409, 5,198,346, and 5,096,815).

Truncation Mutants of Plant Cyclopropane Fatty Acid Synthase

In addition, the present invention provides isolated nucleic acid sequences encoding fragments of plant CPA-FAS (for example, truncation mutants), and the polypeptides encoded by such nucleic acid sequences. In preferred embodiments, the plant CPA-FAS fragment is biologically active. As described above, *Sterculia* CPA-FAS is contemplated to be a natural fusion of two polypeptide fragments possessing different catalytic activities; these two fragments catalyze either the formation of CPA-FA (the carboxy terminus, or the fragment from about amino acids 397 ∀ about 20 amino acids to the end) or ∀-oxidation or a similar reaction (the amino terminus, or the fragment from the beginning to about amino acid 397 ∀ about 20 amino acids). Therefore, it is contemplated that the *Sterculia* CPA-FAS can be truncated into a carboxy terminus fragment and an amino terminus fragment (although each truncation fragment might overlap the other by a number of amino acids), by methods well known. It is contemplated that the truncation site between the two domains is in the region of amino acids 393-401. It is further contemplated that these separate fragments will possess the assigned catalytic activity.

In some embodiments of the present invention, when expression of a portion of a plant CPA-FAS protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) J. Bacteriol., 169:751-757) and *Salmonella typhimurium* and its in vitro activity has been demonstrated on recombinant proteins (Miller et al. (1990) Proc. Natl. Acad. Sci. USA, 84:2718-1722). Therefore, removal of an N-terminal methionine, if desired, can be achieved either in vivo by expressing such recombinant polypeptides in a host that produces MAP (for example, *E. coli* or CM89 or *S. cerevisiae*), or in vitro by use of purified MAP.

Fusion Proteins Containing Plant Cyclopropane Fatty Acid Synthase

The present invention also provides nucleic acid sequences encoding fusion proteins incorporating all or part of plant CPA-FAS, and the polypeptides encoded by such nucleic acid sequences. In some embodiments, the fusion proteins have a plant CPA-FAS functional domain with a fusion partner. Accordingly, in some embodiments of the present invention, the coding sequences for the polypeptide (for example, a plant CPA-FAS functional domain) is incorporated as a part of a fusion gene including a nucleotide sequence encoding a different polypeptide. In one embodiment, a single fusion product polypeptide converts an unsaturated fatty acid to a CPA-FA (one fusion partner possesses the ability to synthesize CPA-FA). In another embodiment, a single fusion product polypeptide converts an unsaturated fatty acid to a CPA-FA of an even carbon number (one fusion partner possesses the ability to synthesize CPA-FA, and a second fusion partner possess the ability to remove a single carbon from the CPA-FA). In yet another embodiment, a single fusion product polypeptide converts an unsaturated fatty acid to a CPE-FA (one fusion partner possesses the ability to synthesize CPA-FA, and a second fusion partner possess the ability to desaturate the CPA-FA). In still another embodiment, a single fusion product polypeptide converts an unsaturated fatty acid to a CPE-FA of an even carbon number (one fusion partner possesses the ability to synthesize CPA-FA, a second fusion partner possess the ability to desaturate the CPA-FA, and a third fusion partner possess the ability to remove a single carbon from the CPA-FA).

In some embodiments of the present invention, chimeric constructs code for fusion proteins containing a portion of a plant CPA-FAS and a portion of another gene. In some embodiments, the fusion proteins have biological activity similar to the wild type plant CPA-FAS (for example, have at least one desired biological activity of plant CPA-FAS). In other embodiments, the fusion protein have altered biological activity.

In other embodiments of the present invention, chimeric constructs code for fusion proteins containing a plant CPA-FAS gene or portion thereof and a leader or other signal sequences which direct the protein to targeted subcellular locations. Such sequences are well known in the art, and direct proteins to locations such as the chloroplast, the mitochondria, the endoplasmic reticulum, the tonoplast, the golgi network, and the plasmalemma.

In addition to utilizing fusion proteins to alter biological activity, it is widely appreciated that fusion proteins can also facilitate the expression and/or purification of proteins, such as a plant CPA-FAS protein of the present invention. Accordingly, in some embodiments of the present invention, a plant CPA-FAS is generated as a glutathione-S-transferase (in other words, GST fusion protein). It is contemplated that such GST fusion proteins enables easy purification of a plant CPA-FAS, such as by the use of glutathione-derivatized matrices (See for example, Ausabel et al. (eds.) (1991) Current Protocols in Molecular Biology, John Wiley & Sons, NY).

In another embodiment of the present invention, a fusion gene coding for a purification leader sequence, such as a poly-(His)/enterokinase cleavage site sequence at the N-terminus of the desired portion of a plant CPA-FAS allows purification of the expressed plant CPA-FAS fusion protein by affinity chromatography using a $Ni^{2+}$ metal resin. In still another embodiment of the present invention, the purification leader sequence is then subsequently removed by treatment with enterokinase (See for example, Hochuli et al. (1987) J. Chromatogr., 411:177; and Janknecht et al. Proc. Natl. Acad. Sci. USA, 88:8972). In yet other embodiments of the present invention, a fusion gene coding for a purification sequence appended to either the N (amino) or the C (carboxy) terminus allows for affinity purification; one example is addition of a hexahistidine tag to the carboxy terminus of a plant CPA-FAS which was optimal for affinity purification.

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See for example, Current Protocols in Molecular Biology, supra).

Screening Gene Products

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of plant CPA-FAS homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate plant CPA-FAS gene products are displayed on the surface of a cell or viral particle, and the ability of particular cells or viral particles to synthesize CPA-FAs is assayed using the techniques described in the Examples. In other embodiments of the present invention, the gene library is cloned into the gene for a surface membrane protein of a bacterial cell, and the resulting fusion protein detected by panning (WO 88/06630; Fuchs et al. (1991) BioTechnol., 9:1370-1371; and Goward et al. (1992) TIBS 18:136-140). In other embodiments of the present invention, fluorescently labeled molecules that bind plant CPA-FAS can be used to score for potentially functional plant CPA-FAS homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical E. coli filamentous phages M13, fd, and fl are most often used in phage display libraries, as either of the phage gIII or gVIII coat proteins can be used to generate fusion proteins without disrupting the ultimate packaging of the viral particle (See for example, WO 90/02909; WO 92/09690; Marks et al. (1992) J. Biol. Chem., 267:16007-16010; Griffths et al. (1993) EMBO J., 12:725-734; Clackson et al. (1991) Nature, 352:624-628; and Barbas et al. (1992) Proc. Natl. Acad. Sci., 89:4457-4461).

In another embodiment of the present invention, the recombinant phage antibody system (for example, RPAS, Pharmacia Catalog number 27-9400-01) is modified for use in expressing and screening of plant CPA-FAS combinatorial libraries. The pCANTAB 5 phagemid of the RPAS kit contains the gene that encodes the phage gIII coat protein. In some embodiments of the present invention, the plant CPA-FAS combinatorial gene library is cloned into the phagemid adjacent to the gIII signal sequence such that it is expressed as a gIII fusion protein. In other embodiments of the present invention, the phagemid is used to transform competent E. coli TG1 cells after ligation. In still other embodiments of the present invention, transformed cells are subsequently infected with M13KO7 helper phage to rescue the phagemid and its candidate plant CPA-FAS gene insert. The resulting recombinant phage contain phagemid DNA encoding a specific candidate plant CPA-FAS-protein and display one or more copies of the corresponding fusion coat protein. In some embodiments of the present invention, the phage-displayed candidate proteins that are capable of, for example, metabolizing a hydroperoxide, are selected or enriched by panning. The bound phage is then isolated, and if the recombinant phage express at least one copy of the wild type gIII coat protein, they will retain their ability to infect E. coli. Thus, successive rounds of reinfection of E. coli and panning will greatly enrich for plant CPA-FAS homologs, which can then be screened for further biological activities in order to differentiate agonists and antagonists.

In light of the present disclosure, other forms of mutagenesis generally applicable will be apparent to those skilled in the art in addition to the aforementioned rational mutagenesis based on conserved versus non-conserved residues. For example, plant CPA-FAS homologs can be generated and screened using, for example, alanine scanning mutagenesis and the like (Ruf et al. (1994) Biochem., 33:1565-1572; Wang et al. (1994) J. Biol. Chem., 269:3095-3099; Balint (1993) Gene 137:109-118; Grodberg et al. (1993) Eur. J. Biochem., 218:597-601; Nagashima et al. (1993) J. Biol. Chem., 268: 2888-2892; Lowman et al. (1991) Biochem., 30:10832-10838; and Cunningham et al. (1989) Science, 244:1081-1085), by linker scanning mutagenesis (Gustin et al. (1993) Virol., 193:653-660; Brown et al. (1992) Mol. Cell. Biol., 12:2644-2652; McKnight et al. Science, 232:316); or by saturation mutagenesis (Meyers et al. (1986) Science, 232:613).

IV. Expression of Cloned Plant Cyclopropane Fatty Acid Synthase

In other embodiment of the present invention, nucleic acid sequences corresponding to the plant CPA-FAS genes, homologs and mutants as described above may be used to generate recombinant DNA molecules that direct the expression of the encoded protein product in appropriate host cells.

As will be understood by those of skill in the art, it may be advantageous to produce plant CPA-FAS-encoding nucleotide sequences possessing non-naturally occurring codons. Therefore, in some preferred embodiments, codons preferred by a particular prokaryotic or eukaryotic host (Murray et al. (1989) Nucl. Acids Res., 17) can be selected, for example, to increase the rate of plant CPA-FAS expression or to produce recombinant RNA transcripts having desirable properties, such as a longer half-life, than transcripts produced from naturally occurring sequence.

A. Vectors for Production of Plant Cyclopropane Fatty Acid Synthase

The nucleic acid sequences of the present invention may be employed for producing polypeptides by recombinant techniques. Thus, for example, the nucleic acid sequence may be included in any one of a variety of expression vectors for expressing a polypeptide. In some embodiments of the present invention, vectors include, but are not limited to, chromosomal, nonchromosomal and synthetic DNA sequences (for example, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the nucleic sequences as broadly described above (for example, SEQ ID NO:1). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, a nucleic acid sequence of the present invention within an expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (for example, dihydrofolate reductase or neomycin resistance for eukaryotic cell culture, or tetracycline or ampicillin resistance in *E. coli*).

In some embodiments of the present invention, transcription of the DNA encoding polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

B. Host Cells for Production of Plant Cyclopropane Fatty Acid Synthase

In a further embodiment, the present invention provides host cells containing any of the above-described constructs. In some embodiments of the present invention, the host cell is a higher eukaryotic cell (for example, a plant cell). In other embodiments of the present invention, the host cell is a lower eukaryotic cell (for example, a yeast cell). In still other embodiments of the present invention, the host cell can be a prokaryotic cell (for example, a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerivisiae, Schizosaccharomycees pombe, Drosophila* S2 cells, Spodoptera Sf9 cells, Chinese hamster ovary (CHO) cells, COS-7 lines of monkey kidney fibroblasts, (Gluzman (1981) Cell 23:175), 293T, C127, 3T3, HeLa and BHK cell lines, NT-1 (tobacco cell culture line), root cell and cultured roots in rhizosecretion (Gleba et al. (1999) Proc Natl Acad Sci USA 96: 5973-5977). Other examples include microspore-derived cultures of oilseed rape. (Weselake R J and Taylor D C (1999) Prog. Lipid Res. 38: 401), and transformation of pollen and microspore culture systems. Further examples are described in the Examples.

The constructs in host cells can be used in a conventional manner to produce the gene product encoded by any of the recombinant sequences of the present invention described above. In some embodiments, introduction of the construct into the host cell can be accomplished by calcium phosphate transfection, DEAE-Dextran mediated transfection, or electroporation (See for example, Davis et al. (1986) Basic Methods in Molecular Biology). Alternatively, in some embodiments of the present invention, a polypeptide of the invention can be synthetically produced by conventional peptide synthesizers.

Proteins can be expressed in eukaryotic cells, yeast, bacteria, or other cells under the control of appropriate promoters. Cell-free translation systems can also be employed to produce such proteins using RNAs derived from a DNA construct of the present invention. Appropriate cloning and expression vectors for use with prokaryotic and eukaryotic hosts are described by Sambrook, et al. (1989) *Molecular Cloning: A Laboratory Manual*, Second Edition, Cold Spring Harbor, N.Y.

In some embodiments of the present invention, following transformation of a suitable host strain and growth of the host strain to an appropriate cell density, the selected promoter is induced by appropriate means (for example, temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

VI. Production of Large Quantities of Cyclopropane Fatty Acids

In one aspect of the present invention, methods are provided for producing large quantities of CPA-FAs. In some embodiments, CPA-FAs are produced in vivo, in organisms transformed with a heterologous gene encoding a polypeptide exhibiting plant cyclopropane fatty acid synthase activity and grown under conditions sufficient to effect production of CPA-FAs. In other embodiments, CPA-FAs are produced in vitro, from either nucleic acid sequences encoding a plant CPA-FAS or from polypeptides exhibiting plant cyclopropane fatty acid synthase activity.

A. In Vivo in Transgenic Organism

In some embodiments of the present invention, CPA-FAs are produced in vivo, by providing an organism transformed with a heterologous gene encoding a plant CPA-FAS activity and growing the transgenic organism under conditions sufficient to effect production of CPA-FAs. In other embodiments of the present invention, CPA-FAs are produced in vivo by transforming an organism with a heterologous gene encoding a plant CPA-FAS and growing the transgenic organism under conditions sufficient to effect production of CPA-FAs. Illustrative examples of transgenic organisms are provided in the Examples.

Organisms which are transformed with a heterologous gene encoding a plant CPA-FAS include preferably those which naturally synthesize and store in some manner fatty acids, and those which are commercially feasible to grow and suitable for harvesting large amounts of the fatty acid products. Such organisms include but are not limited to bacteria, oleaginous yeast and algae, and plants. Examples of bacteria include *E. coli* and related bacteria which can be grown in commercial-scale fermenters. Examples of plants include preferably oil-producing plants, such as soybean, rapeseed and canola, sunflower, cotton, corn, cocoa, safflower, oil palm, coconut palm, flax, castor, and peanut. Many commercial cultivars can be transformed with heterologous genes. In cases where that is not possible, non-commercial cultivars of plants can be transformed, and the trait for expression of plant CPA-FAS moved to commercial cultivars by breeding techniques well-known in the art.

A heterologous gene encoding a plant CPA-FAS, which includes mutants or variants of a plant CPA-FAS, includes any suitable sequence of the invention as described above. Preferably, the heterologous gene is provided within an expression vector such that transformation with the vector results in expression of the polypeptide; suitable vectors are described above and following.

A transgenic organism is grown under conditions sufficient to effect production of CPA-FAs. In some embodiments of the present invention, a transgenic organism is supplied with exogenous substrates of the plant CPA-FAS (as for example as in a fermenter). Such substrates comprise unsaturated fatty acids; the number of double bonds is from one to more than one, and the chain length of such unsaturated fatty acids is variable, but is preferably about 14 to 22 carbons in length. The fatty acid substrate may also comprise additional functional groups, including but not limited to acetylenic bonds, conjugated acetylenic and ethylenic bonds, allenic groups, furan rings, and epoxy-, and keto-groups; two or more of these functional groups may be found in a single fatty acid. The substrates are either free fatty acids, or their salts. Substrates may be supplied in various forms as are well known in the art; such forms include aqueous suspensions prepared by sonication, aqueous suspensions prepared with detergents and other surfactants, dissolution of the substrate into a solvent, and dried powders of substrates. Such forms may be added to organisms or cultured cells or tissues grown in fermenters.

In yet other embodiments of the present invention, a transgenic organism comprises a heterologous gene encoding a plant CPA-FAS operably linked to an inducible promoter, and is grown either in the presence of the an inducing agent, or is grown and then exposed to an inducing agent. In still other embodiments of the present invention, a transgenic organism comprises a heterologous gene encoding a plant CPA-FAS operably linked to a promoter which is either tissue specific or developmentally specific, and is grown to the point at which the tissue is developed or the developmental stage at which the developmentally-specific promoter is activated. Such promoters include seed specific promoters.

In alternative embodiments, a transgenic organism as described above is engineered to produce greater amounts of the unsaturated substrate. In one embodiment, a transgenic organism is co-transformed with a heterologous gene encoding a protein which desaturates fatty acids, such that the fatty acid desaturase is expressed. More preferably, the plant CPA-FAS and the heterologous fatty acid desaturase are targeted to the same intracellular location; most preferably, such a location serves to synthesize oil, such as a microsome in plants. These co-transformants are then grown under conditions sufficient to effect production of CPA-FAs. In some embodiments of the present invention, a co-transformant is supplied with exogenous substrates of the fatty acid desaturase; such substrates comprise saturated and unsaturated fatty acids. The chain length of such unsaturated fatty acids is variable, but is preferably about 14 to 22 carbons in length. The fatty acid substrate may also comprise additional functional groups, including but not limited to acetylenic bonds, conjugated acetylenic and ethylenic bonds, allenic groups, and epoxy-, and keto-groups; two or more of these functional groups may be found in a single fatty acid. The substrates are either free fatty acids, or are fatty acids incorporated into a larger molecule, such as a glycerolipid. Most preferably, the fatty acid substrate is esterified to a phospholipid. Substrates may be supplied, added, or applied as described above.

In other embodiments, the heterologous genes are under control of promoters which are either inducible, tissue-specific, or developmentally specific, and the organism is grown as described above, such that the heterologous genes encoding polypeptides with the fatty acid desaturase and the plant CPA-FAS activities are expressed.

In yet further embodiments of the invention, an organism is transformed with a nucleotide sequence coding for a fusion protein comprising both a fatty acid desaturase and a plant CPA-FAS, as described above, such that both enzymatic activities are expressed. Such transgenic organisms are grown as described above.

In other embodiments of the present invention, a host organism is one which produces large amounts of the substrate. For example, it is contemplated that oleate is a preferred substrate of Sterculia CPA-FA; thus, a particularly suitable host in one which produces a high proportion of oleic acid. Such hosts include plant lines bred to produce high oleic oils, such as sunflower or corn; such lines are produced from individual plants in which FAD2 of naturally low levels is selected, as well as those plants subjected to mutagenesis and subsequently selected for decreased FAD2 activity, and those plants subjected to knock-out technology, in which FAD2 is silenced by antisense or co-suppression. In other lines, the synthesis of shorter chain fatty acids is also decreased, by any of the means described above, resulting in increased expression of oleic acid. Any of these modifications may also be combined, to produce plant lines with even higher amounts of oleic acid.

In other embodiments of the present invention, the methods for producing large quantities of CPA-FAs further comprise collecting the CPA-FAs produced. Such methods are known generally in the art, and include harvesting the transgenic organisms and extracting the CPA-FAs (see, for example, Christie, W. W. (1982) *Lipid Analysis*, $2^{nd}$ Edition (Pergamon Press, Oxford); and Kates, M (1986) *Techniques of Lipidology* (Elsevier, Amsterdam)). Extraction procedures preferably include solvent extraction, and typically include disrupting cells, as by chopping, mincing, grinding, and/or sonicating, prior to solvent extraction. In one embodiment, lipids are extracted from the tissue according to the method of Bligh and Dyer (1959) (Can J Biochem Physiol 37: 911-917); fatty acids esterified to glycerolipids can be hydrolyzed under acidic or alkaline conditions and collected by solvent extraction. In yet other embodiments of the present invention, the CPA-FAs are further purified, as for example by thin layer liquid chromatography, gas-liquid chromatography, or high pressure liquid chromatography.

1. Transgenic Plants, Seeds, and Plant Parts

Plants are transformed with a heterologous gene encoding a plant CPA-FAS or co-transformed with a first heterologous gene encoding plant CPA-FAS and with a second heterologous gene encoding fatty acid desaturase or transformed with a fusion gene encoding a fusion polypeptide expressing a plant CPA-FAS and fatty acid desaturase activities according to procedures well known in the art. It is contemplated that the heterologous genes are utilized to increase the level of the enzyme activities encoded by the heterologous genes.

a. Plants

The methods of the present invention are not limited to any particular plant. Indeed, a variety of plants are contemplated, including but not limited to tomato, potato, tobacco, pepper, rice, corn, barley, wheat, Brassica, Arabidopsis, sunflower, soybean, poplar, and pine. Preferred plants include oil-producing species, which are plant species which produce and store triacylglycerol in specific organs, primarily in seeds. Such species include but are not limited to soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling *Brassica* species, and *Arabidopsis thaliana*, and wild species which may be a source of unique fatty acids. Preferred plant lines include those which are high monounsaturates, and in particular high oleates, as described previously. Particularly preferred plant lines are oilseed crop lines with a high oleate background. The high oleate background can be generated, for example, by using existing plant lines which are derived through breeding and/or mutagenesis (for example, high oleic sunflower lines and high oleate rapeseed lines), or by using genetically engineered lines, such as the high oleate soybean generated by fad2 co-suppression, or the OLE1 gene to reduce saturates b. Vectors The methods of the present invention contemplate the use of a heterologous gene encoding a plant CPA-FAS, as described above. The methods of the present invention further contemplate the use of a second heterologous gene which encodes a fatty acid desaturase; such polypeptides are known (See, for example, Polashock J J, Chin C-K, Martin C E (1992) Plant Physiol. 100: 894-901, which describes expression of the yeast delta-9 fatty acid desaturase in *Nicotiana tabaccum*. The yeast delta-9 fatty acid desaturase is the OLE1 gene, which can increase 16:1 and 18:1 levels in plant tissues.) Heterologous genes encoding mutants and variants of fatty acid desaturases are prepared as described above for plant CPA-FAS. Heterologous genes encoding a fusion CPA-FAS/fatty acid desaturase is prepared as described above.

Heterologous genes intended for expression in plants are first assembled in expression cassettes comprising a promoter. Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See for example, Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y).

In general, these vectors comprise a nucleic acid sequence of the invention encoding a plant CPA-FAS (as described above) operably linked to a promoter and other regulatory sequences (for example, enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," Chao et al. (1999) Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (for example, phaseolin, napin, oleosin, and a promoter for soybean beta conglycin (Beachy et al. (1985) EMBO J. 4: 3047-3053)). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tm1 terminator, the pea rbcS E9 terminator, and the nopaline and octopine synthase terminator (See for example, Odell et al. (1985) Nature 313:810; Rosenberg et al. (1987) Gene, 56:125; Guerineau et al. (1991) Mol. Gen. Genet., 262:141; Proudfoot (1991) Cell, 64:671; Sanfacon et al. Genes Dev., 5:141; Mogen et al. (1990) Plant Cell, 2:1261; Munroe et al. (1990) Gene, 91:151; Ballad et al. (1989) Nucleic Acids Res. 17:7891; Joshi et al. (1987) Nucleic Acid Res., 15:9627).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize AdhI gene have been found to significantly enhance the expression of the wild-type gene under its cognate promoter when introduced into maize cells (Calais et al. (1987) Genes Develop. 1: 1183). Intron sequences have been routinely incorporated into plant transformation vectors, typically within the non-translated leader.

In some embodiments of the present invention, the construct for expression of the nucleic acid sequence of interest also includes a regulator such as a nuclear localization signal (Calderone et al. (1984) Cell 39:499; Lassoer et al. (1991) Plant Molecular Biology 17:229), a plant translational consensus sequence (Joshi (1987) Nucleic Acids Research 15:6643), an intron (Luehrsen and Walbot (1991) Mol. Gen. Genet. 225:81), and the like, operably linked to the nucleic acid sequence encoding plant CPA-FAS.

In preparing the construct comprising a nucleic acid sequence encoding plant CPA-FAS, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304:184), the bar gene which confers resistance to the herbicide phosphinothricin (White et al. (1990) Nucl Acids Res. 18: 1062; Spencer et al. (1990) Theor. Appl. Genet. 79: 625), the hph gene which confers resistance to the antibiotic hygromycin (Blochlinger and Diggelmann (1984) Mol. Cell. Biol. 4:2929), and the dhfr gene, which confers resistance to methotrexate (Bourouis et al. (1983) EMBO J., 2:1099).

In some preferred embodiments, the vector is adapted for use in an *Agrobacterium* mediated transfection process (See for example, U.S. Pat. Nos. 5,981,839; 6,051,757; 5,981,840;

5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA 1-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Generally, the inserted plant CPA-FAS polynucleotide of the present invention can be expressed from these vectors as a fusion protein (for example, coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

In some embodiments of the present invention, where the nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (WO 93/07278).

c. Transformation Techniques

Once a nucleic acid sequence encoding a plant CPA-FAS is operatively linked to an appropriate promoter and inserted into a suitable vector for the particular transformation technique utilized (for example, one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See for example, U.S. Pat. Nos. 5,451,513; 5,545,817; 5,545,818; PCT application WO 95/16783). The basic technique for chloroplast transformation involves introducing regions of cloned plastid DNA flanking a selectable marker together with the nucleic acid encoding the RNA sequences of interest into a suitable target tissue (for example, using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) PNAS, 87:8526; Staub and Maliga, (1992) Plant Cell, 4:39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202:179). In still other embodiments, the vector is transferred into the plant cell by using polyethylene glycol (Krens et al. (1982) Nature, 296:72; Crossway et al. (1986) BioTechniques, 4:320); fusion of protoplasts with other entities, either minicells, cells, lysosomes or other fusible lipid-surfaced bodies (Fraley et al. (1982) Proc. Natl. Acad. Sci., USA, 79:1859); protoplast transformation (EP 0 292 435); direct gene transfer (Paszkowski et al. (1984) EMBO J., 3:2717; Hayashimoto et al. (1990) Plant Physiol. 93:857).

In still further embodiments, the vector may also be introduced into the plant cells by electroporation. (Fromm, et al. (1985) Pro. Natl Acad. Sci. USA 82:5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (for example, available from Agracetus, Inc., Madison, Wis. and Dupont, Inc., Wilmington, Del.). (See for example, U.S. Pat. No. 4,945,050; and McCabe et al. (1988) Biotechnology 6:923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8:833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338: 274 (rice); Christou et al. (1991) Biotechnology, 9:957 (rice); Datta et al. (1990) Bio/Technology 8:736 (rice); European Patent Application EP 0 332 581 (orchardgrass and other Pooideae); Vasil et al. (1993) Biotechnology, 11: 1553 (wheat); Weeks et al. (1993) Plant Physiol., 102: 1077 (wheat); Wan et al. (1994) Plant Physiol. 104: 37 (barley); Jahne et al. (1994) Theor. Appl. Genet. 89:525 (barley); Knudsen and Muller (1991) Planta, 185:330 (barley); Umbeck et al. (1987) Bio/Technology 5: 263 (cotton); Casas et al (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat) and Nehra et al. (1994) The Plant Journal, 5:285 (wheat).

In addition to direct transformation, in some embodiments, the vectors comprising a nucleic acid sequence encoding a plant CPA-FAS of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237: 1176). Species which are susceptible infection by *Agrobacterium* may be transformed in vitro. Alternatively, plants may be transformed in vivo, such as by transformation of a whole plant by *Agrobacteria* infiltration of adult plants, as in a "floral dip" method (Bechtold N, Ellis J, Pelletier G (1993) Cr. Acad. Sci. III-Vie 316:1194-1199).

d. Regeneration

After selecting for transformed plant material which can express the heterologous gene encoding a plant CPA-FAS, whole plants are regenerated. Plant regeneration from cultured protoplasts is described in Evans et al. (1983) Handbook of Plant Cell Cultures, Vol. 1: (MacMillan Publishing Co. New York); and Vasil I. R. (ed.), Cell Culture and Somatic Cell Genetics of Plants, Acad. Press, Orlando, Vol. I (1984), and Vol. III (1986). It is known that many plants can be regenerated from cultured cells or tissues, including but not limited to all major species of sugarcane, sugar beet, cotton, fruit and other trees, legumes and vegetables, and monocots (for example, the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos geminate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

e. Generation of Transgenic Lines

Transgenic lines are established from transgenic plants by tissue culture propagation. The presence of nucleic acid sequences encoding exogenous a plant CPA-FAS of the present invention (including mutants or variants thereof may be transferred to related varieties by traditional plant breeding techniques.

These transgenic lines are then utilized for evaluation of oil production and other agronomic traits.

B. In Vitro Systems

In other embodiments of the present invention, CPA-FAs are produced in vitro, from either nucleic acid sequences encoding a plant CPA-FAS or from polypeptides exhibiting plant cyclopropane fatty acid synthase activity.

1. Using Nucleic Acid Sequences Encoding Plant Cyclopropane Fatty Acid Synthase

In some embodiments of the present invention, methods for producing large quantities of CPA-FAs comprise adding an isolated nucleic acid sequence encoding a plant CPA-FAS to in vitro expression systems under conditions sufficient to cause production of CPA-FAs. The isolated nucleic acid sequences encoding a plant cyclopropane is any suitable sequence of the invention as described above, and preferably is provided within an expression vector such that addition of the vector to an in vitro transcription/translation system results in expression of the polypeptide. The system further comprises the substrates for plant CPA-FAS, as previously described. Alternatively, the system further comprises the means for generating the substrates for plant CPA-FAS. Such means include but are not limited to the provision of at least one protein exhibiting fatty acid desaturase activity, and substrates for fatty acid desaturase, as described above.

In other embodiments of the present invention, the methods for producing large quantities of CPA-FAs further comprise collecting the CPA-FAs produced. Such methods are known generally in the art. In yet other embodiments of the present invention, the CPA-FAs are further purified, as for example by thin layer liquid chromatography, gas-liquid chromatography, or high pressure liquid chromatography.

2. Using Plant Cyclopropane Synthase Polypeptides

In some embodiments of the present invention, methods for producing large quantities of CPA-FAs comprise incubating a plant CPA-FAS under conditions sufficient to result in the synthesis of CPA-FAs; generally, such incubation is carried out in a mixture which comprises the plant CPA-FAS.

A plant CPA-FAS, as described previously, is obtained by purification of either naturally occurring plant CPA-FAS or recombinant plant CPA-FAS from an organism transformed with heterologous gene encoding a plant CPA-FAS, as previously described. A source of naturally occurring plant CPA-FAS is contemplated to include but not limited to plants, as for example Malvaceae, sterculiaceae, Bombaceae, Tilaceae, Mimosaceae and Sapindaceae. A source of recombinant plant CPA-FAS is either plant, bacterial or other transgenic organisms, transformed with heterologous gene encoding plant CPA-FAS as described above. The recombinant plant CPA-FAS may include means for improving purification, as for example a 6x-His tag added to the C-terminus of the protein as described above. Alternatively, plant CPA-FAS is chemically synthesized.

The incubation mixture further comprises the substrates for plant CPA-FAS, as described above. Alternatively, the mixture further comprises the means for generating the substrates for plant CPA-FAS. Such means include but are not limited to the provision of at least one protein exhibiting fatty acid desaturase activity, and appropriate substrates for fatty acid desaturase, as described above. Additional substrates include but are not limited substrates for the synthesis of phospholipids, such as lyso-phospholipid and phospholipid acyl-transferase, as well as phospholipid liposomes with lipid transfer proteins; particularly preferred phospholipids are phosphatidylcholines.

In other embodiments of the present invention, the methods for producing large quantities of CPA-FAs further comprise collecting the CPA-FAs produced; such methods are described above.

VII. Production of Cyclopropane Fatty Acids Where Not Normally Present

In another aspect of the present invention, methods are provided for producing CPA-FAs in organisms and/or tissues where CPA-FAs are not usually present or are present in very low levels. In this aspect, CPA-FAs are produced in organisms transformed with a heterologous gene encoding a polypeptide exhibiting plant cyclopropane fatty acid synthase activity and grown under conditions sufficient to effect production of CPA-FAs. In some embodiments, the methods comprise production of CPA-FAs in specific tissues or organs, such as in plant roots. In other embodiments, the methods comprise production of CPA-FAs at specific developmental phases. In yet other embodiments, the methods comprise production of CPA-FAs in specific tissues or organs and at specific developmental phases.

In this aspect, the CPA-FAs are contemplated to serve a physiological role. For example, it is contemplated that CPA-FAs provide fungal resistance to plant roots. Thus, expression of CPA-FAS in plant roots which normally do not possess CPA-FAs, or possess CPA-FAs at insignificant levels, provides increased fungal resistance.

In some embodiments of the present invention, the methods comprise providing a transgenic organism comprising a heterologous gene encoding a plant CPA-FAS operably linked to an inducible promoter, and growing the transgenic organism either in the presence of the an inducing agent, or growing the organism and then exposing it to an inducing agent, thereby expressing CPA-FAS resulting in the production of CPA-FAs. In still other embodiments of the present invention, the methods comprise providing a transgenic organism comprising a heterologous gene encoding a plant CPA-FAS operably linked to a promoter which is either tissue specific or developmentally specific, and growing the transgenic organism to the point at which the tissue is developed or the developmental stage at which the developmentally-specific promoter is activated, thereby expressing CPA-FAS resulting in the production of CPA-FAs. Exemplary promoters include but are not limited to seed specific promoters.

A heterologous gene encoding a plant CPA-FAS, which includes mutants or variants of a plant CPA-FAS, includes any suitable sequence of the invention as described above. Preferably, the heterologous gene is provided within an expression vector such that transformation with the vector results in expression of the polypeptide; suitable vectors are described above and following.

Methods of producing transgenic organisms, and in particular transgenic plants, are described above.

VIII. Manipulation of Plant Cyclopropane Fatty Acid Synthase Activity in Plants

As noted above, CPE-FAs are considered an anti-nutritional factor in food oils, yet many seed lipids containing CPE-FAs are extensively consumed by humans, especially in tropical areas, and by animals as well (for example, cottonseed meal is a typical animal feed product, and is a by-product of cottonseed processing to obtain the oil). Because of these health concerns, vegetable oils containing CPE-FAs must be treated with high temperature or hydrogenation before consumption. These treatments add to the oil processing costs, and also result in the presence of a certain percentage of trans fatty acids produced due the hydrogenation; the presence of such trans fatty acids are also undesirable. Therefore, the present invention provides methods to eliminate CPE-FAs from seed oils, as well as plants which produce oils with reduced levels of CPE-FAs, and oils with reduced levels CPE-FAs which are not treated with high temperature or hydrogenation to reduce CPE-FAs levels and which have low levels of trans fatty acids. These aspects of the invention have great utility in significantly reducing oil processing costs, decreasing the presence of undesirable hydrogenated fatty acids, and enhancing the value of both the seed oils, of unprocessed seed and of processed seed meal for food consumption. Some embodiments of the present invention provides methods to decrease the amount of CPE-FAs from plant seed oils by cyclopropane synthase gene silencing technology. Other embodiments provide methods of decreasing the amount of CPE-FAs from cotton seed oils by cyclopropane synthase gene silencing technology It is further contemplated that the nucleic acids encoding a plant CPA-FAS of the present invention may be utilized to either increase or decrease the level of plant CPA-FAS mRNA and/or protein in transfected cells as compared to the levels in wild-type cells. Such transgenic cells have great utility, including but not limited to further research as to the effects of the overexpression of plant CPA-FAS, and as to the effects as to the underexpression or lack of plant CPA-FAS.

Accordingly, in some embodiments, expression in plants by the methods described above leads to the overexpression of plant CPA-FAS in transgenic plants, plant tissues, or plant cells.

In other embodiments of the present invention, the plant CPA-FAS polynucleotides are utilized to decrease the level of plant CPA-FAS protein or mRNA in transgenic plants, plant tissues, or plant cells as compared to wild-type plants, plant tissues, or plant cells. One method of reducing plant CPA-FAS expression utilizes expression of antisense transcripts. Antisense RNA has been used to inhibit plant target genes in a tissue-specific manner (for example, van der Krol et al. (1988) Biotechniques 6:958-976). Antisense inhibition has been shown using the entire cDNA sequence as well as a partial cDNA sequence (for example, Sheehy et al. (1988) Proc. Natl. Acad. Sci. USA 85:8805-8809; Cannon et al. (1990) Plant Mol. Biol. 15:39-47). There is also evidence that 3' non-coding sequence fragment and 5' coding sequence fragments, containing as few as 41 base-pairs of a 1.87 kb cDNA, can play important roles in antisense inhibition (Ch'ng et al. (1989) Proc. Natl. Acad. Sci. USA 86:10006-10010).

Accordingly, in some embodiments, a plant CPA-FAS encoding-nucleic acid of the present invention (for example, SEQ ID NO: 1, and fragments and variants thereof) are oriented in a vector and expressed so as to produce antisense transcripts. To accomplish this, a nucleic acid segment from the desired gene is cloned and operably linked to a promoter such that the antisense strand of RNA will be transcribed. The expression cassette is then transformed into plants and the antisense strand of RNA is produced. The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

Furthermore, for antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of the target gene or genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, Solanum nodiflorum mottle virus and subterranean clover mottle virus. The design and use of target RNA-specific ribozymes is described in Haseloff, et al. (1988) Nature 334:585-591. Ribozymes targeted to the mRNA of a lipid biosynthetic gene, resulting in a heritable increase of the target enzyme substrate, have also been described (Merlo A O et al. (1998) Plant Cell 10: 1603-1621).

Another method of reducing CPA-FAS expression utilizes the phenomenon of cosuppression or gene silencing (See for example, U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (for example, Napoli et al. (1990) Plant Cell 2:279-289; van der Krol et al. (1990) Plant Cell 2:291-299; Smith et al. (1990) Mol. Gen. Genetics 224: 477-481). Accordingly, in some embodiments the nucleic acid sequences encoding a plant CPA-FAS of the present invention (for example including SEQ ID NOs: 1, and fragments and variants thereof) are expressed in another species of plant to effect cosuppression of a homologous gene.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For cosuppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

An effective method to down regulate a gene is by hairpin RNA constructs. Guidance to the design of such constructs for efficient, effective and high throughput gene silencing have been described (Wesley S V et al. (2001) Plant J. 27: 581-590). Another method to decrease expression of a gene (either endogenous or exogenous) is via siRNAs. siRNAs can be applied to a plant and taken up by plant cells; alternatively, siRNAs can be expressed in vivo from an expression cassette.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); :m (micromolar); mol (moles); mmol (millimoles); :mol (micromoles); nmol (nanomoles); pmol (picomoles); g (grams); mg (milligrams); :g (micrograms); ng (nanograms); l or L (liters); ml (milliliters); :l (microliters); cm (centimeters); mm (millimeters); :m (micrometers); nm (nanometers); ° C. (degrees Centigrade); PCR (polymerase chain reaction); RT-PCR (reverse-transcriptase-PCR); TAIL-PCR (thermal asymmetric interlaced-PCR); EST, expressed sequence tag; BLAST; FAME, fatty acid methyl ester; GC/MS, gas chromatography/mass spectrometry; TLC, thin layer chromatography; SC medium; NT medium; MES; 2,4-D; CPA-FA, cyclopropane fatty acids; CPE-FA, cyclopropene fatty acids; DHSA, dihydrosterculic acid; SCPA-FAS, *Sterculia* cyclopropane fatty acid synthase; MSU, Michigan State University;

EXAMPLE 1

Experimental Procedures

Materials

Developing Seeds

*Sterculia foetida* developing seeds were collected from Jul. 20 to Oct. 15, 1998 at Miami Montgomery Botanical Center (Florida USA 33156-4242). Upon receipt of the fresh seeds, the seed coats were removed and the cotyledons and embryos were either immediately used fresh for labeling experiments or frozen and stored at −80° C. for subsequent RNA extraction and lipids analysis.

Tobacco Suspension Cells

Tobacco suspension cells (*Nicotiana tabaccum* L. cv. Bright yellow 2) were maintained in liquid medium containing Murashige and Skoog basal salts (Gibco, Grand island, NY), 3% sucrose, 2.5 mM MES/KOH pH 5.7, 1 mg/ml thiamine, 1 mg/ml myo-inositol, and 1:M 2,4-D. Cultures were sub-cultured weekly with 5% (v/v) inoculum from a 7-day old culture and shaken at 28° C. in 200 ml flasks.

Chemicals

Radio-isotopes, L-[methyl-$^{14}$C] methionine (55 mCi/mmol), [1-$^{14}$C] acetate (55 mCi/mmol) and [1-$^{14}$C] oleic acid (50 mCi/mmol) were purchased from American Radiolabeled Chemicals, Inc.).

Lipid Analysis

To determine the fatty acid accumulation during *Sterculia* seed development, 2 mg triacylglycerol (13:0-1.89 mg) were added as an internal standard to 200 mg seed tissue (fresh weight) before the lipid extraction. Lipids were extracted at each developmental stage according to the method of Bligh and Dyer (1959) Can J Biochem Physiol 37, 911-917). Fatty acid methyl esters (FAMES) were prepared by transferring an aliquot of the lipid extract into a new tube and drying the extract under nitrogen. 2.5 ml of 1% sodium methoxide in methanol and 2.5 ml of heptane were added to each tube, and the mixture vortexed at room temperature for 2 to 3 minutes. 2.5 ml of water was added to each tube, and the mixture vortexed briefly. The FAMES were extracted by washing the mixture three times with 2.5 ml of hexane, and the combined organic phases were then washed two times with 3.0 ml of water, and dried under nitrogen. The FAMES were then analyzed by GC-MS, using a Hewlett Packard 5890 gas chromatography configured with an autosampler and HP MSD 5972 mass analyzer (quadruple, operating in electron impact mode). Separation of the FAMEs was carried out on a DB 23 column of 30 m long with diameter of 0.25 mm.

Lipid extraction, preparation of fatty acid methyl esters, and their analysis by GC/MS for yeast and tobacco suspension cells followed the same procedure as described above for *Sterculia* seeds, except that no internal fatty acid standard was added. In order to accurately determine the identity of dihydrosterculic acid (DHSA) in transgenic tobacco suspension cells, the saturated and unsaturated fatty acid methyl esters were separated by argentation TLC (Norris et al. (1967) J Chromatography 31: 69-76). Argentation plates (15% silver nitrate) were developed sequentially at −20° C. to heights of 8, 13, and 19 cm in toluene. The fatty acid methyl esters on the plates were located by spraying with 0.2% (w/v) 2',7'-Dichlorofluorescein in ethanol. The saturated fatty acid methyl-ester bands on top of the argentation plates were scraped into test tubes, recovered by elution with 6 ml of hexane: ethyl ether (2:1, v/v), and analyzed by GC/MS.

Assay of Cyclopropane Fatty Acid Synthesis

Cyclopropane fatty acid synthase in tissue homogenates was assayed in a reaction mixture containing 0.1 ml of cell free homogenate, 0.02-0.05 mM oleoyl-CoA, and 0.02 mM [$^{14}$C-methyl]S-adenosylmethionine substrate, in a total volume of 0.2 ml. The presence of oleoyl-CoA enhances activity about two-fold over its absence, but higher concentrations of oleoyl-CoA are inhibitory. The Km for S-adenosylmethionine in the crude extract is 0.02 mM. The assay cocktail was incubated at 30° C. for 1 hour. The assay was terminated by the addition of 0.5 ml of aqueous KOH and 1.0 ml of ethanol, and allowed to stand overnight to give complete saponification of the lipids. On acidification, the labeled free fatty acids were extracted into hexane, then the hexane phase washed with water and evaporated to dryness. An aliquot of the organic phase was assayed for radioactivity. The remainder of the product was analyzed by TLC. A portion of the fatty acid products may also be derivatized with ethereal diazomethane.

Radiolabeling *Sterculia* Developing Seeds and Transgenic Tobacco Cells

Developing seeds from the collection of August 25 were used for labeling experiments. One cotyledon was sliced into 8 pieces, incubated in 0.5 ml of labeling buffer (50 mM phosphate pH 7.0 with 5:Ci of radio-isotope) at room temperature shaking constantly. The labeling was terminated at 30, 60, and 120 minutes by immediate lipid extraction. The fatty acid methyl-esters from these samples were separated on C18 reverse phase TLC in the solvent system of acetonitrile:methanol:water (75:25:0.5, v/v). The radioactivity was visualized with Instant-Imager.

Independent transgenic callus was transferred back into liquid medium and the cells sub-cultured as described above. After three days of subculture, 5:Ci of L-[methyl-$^{14}$C] methionine or [1-$^{14}$C] oleic acid was added to the medium, and the cells were incubated for an additional 24 hours. The cells were then collected by brief centrifugation, followed by lipid extraction and preparation of fatty acid methyl-esters. Saturated fatty acids were separated from unsaturated fatty acids by argentation TLC, the individual saturated fatty acids were separated from each other by C18 reverse phase TLC, and the radio-active spots were recovered for GC/MS analysis.

Library Construction and Sequencing

Equal amounts of developing seeds from the seeds collected on August 5, August 25, September 10, and September 30 were pooled together. During this period of time, the deposition of oil showed a linear increase (see Example 2). Ten grams of the pooled developing seeds were ground into a fine powder in liquid nitrogen. The RNA was extracted as described by Schultz et al (1994). The quality of the isolated total RNA was analyzed by separation on 1% formaldehyde agarose gel. The cDNA library was prepared from the total isolated RNA of *Sterculia* developing seeds by Stratagene (11011 North Torrey Pines Road, La Jolla, Calif. 92037). The cDNAs were directionally cloned into Uni-ZAP® at EcoRI and XhoI sites. Mass excisions were performed according the protocol provided by Stratagene. A total of 21,120 clones were picked and grown in 220 '96-well plates. Twenty-eight out the 220 plates were directly sequenced at the MSU sequencing facility. The remaining 192 plates (18432 clones) were spotted on filters by Genome System for library subtraction. Based on the information obtained from the first 1,500 sequences from the non-subtracted library, three most abundant sequences were chosen to subtract from the library on the filters. A total of seventy 96-well plates were re-racked and sequenced.

Constructs For Tobacco and Yeast Expression

A putative *Sterculia* cyclopropane synthase (SCPA-FAS) gene was identified based on sequence homology with bacterial cyclopropane synthase. The complete cDNA of the putative (SCPA-FAS) is 2977 bp long and was compiled from two overlapping clones R50-D5 (1-1732 bp) and C15-C3 (933-2977 bp). Both clones were sequenced from both strands. In order to put the complete putative SCPA-FAS together, the sequence encoding amino acids 1-335 was amplified from clone R50-D5 with primers JO886 (TCCTCTAGACTCGAGCCCGGGATGGGAGTGGCT GTGATCGGTGGTGGGATC (SEQ ID NO:27)) and JO883 (GTTGTAAGACGTCGTGTAACTCGGTC ATACAATTCG SEQ ID NO:28)), and the sequence encoding amino acids 336-864 and containing the stop codon was amplified from clone C15-C3 with primers JO884 (CAATGTGCTGCAGAATGTTGGGAAAACAAGTCAGCC (SEQ ID NO:29) and JO885 (GGGAGATCTCGAGCCTATTTACTTTTGATAAAGTTAATAGGC (SEQ ID NO:30). For ease of cloning, a null mutation was made at the third position of the codon for amino acid 335 lysine, which changed the lysine codon from CTA to CTG, so that a Pst I site could be created. The upstream fragment was inserted into pBluescript KS at XhoI and PstI sites, and the downstream fragment was inserted at PstI and XbaI. The resulting construct was named pBluescript KS-SCPAS; this construct was re-sequenced from both strands, and found to be error-free. The complete SCPA-FAS was released from pBluescript KS at SmaI and XbaI sites and inserted into the binary vector pE1776 between SmaI and XbaI site. pE 1776 carries the constitutive promoter "Super Promoter" and an ags terminator. The resulting construct was named as pE1776-SCPAS and transferred into *Agrobacterium* strain LBA4404 for tobacco suspension cell transformation.

For the yeast construct, in order to create an EcoRI site upstream, amino acid 1-335 was amplified from clone R50-D5 with primer JO968 (GCCCTCGAGAATTCTAAAATGTCTGTGGCTGTGATCGGTGGTGGGATCCAAGGGCTGG) (SEQ ID NO:31) and JO883R (GTTGTAAGAC GTCGTGTAACTCGGTCATACAATTCG (SEQ ID NO:28). The PCR fragment was digested with XhoI and PstI, and used to replace the corresponding section in the construct of pBluescript KS-SCPAS. The SCPA-FAS was released with EcoRI and XbaI, and inserted into the yeast vector pYES2/CT (Invitrogen). The resulting construct was named as pYES2/CT-SCPAS.

Expression of SCPA-FAS in Yeast and Tobacco Suspension Cells

The construct pYES2/CT-SCPAS was transformed into yeast strain InvSc1 using the S.c.EasyComp™ Transformation Kit (Invitrogen Cat# K5050-01). To express SCPA-FAS, a yeast colony containing pYES2/CT-SCPAS was inoculated into 50 ml of SC medium with 2% galactose and 200 mg/L oleic acid. The culture was grown at 28° C. shaking at 150 rpm. After 48 hr growth, yeast cells were collected by brief centrifugation; the yeast lipids extracted were extracted from the pellet, and fatty acid methyl-esters prepared from the extracted lipids and analyzed by GC/MS.

*Agrobacterium* mediated tobacco transformation was carried out as described by Rempel and Nelson (1991). The agrobacterial culture was grown overnight, and 100 ul of culture containing the proper construct was added to 4 ml samples of 3-day-old tobacco suspension cells. The cells were then cultured at 28° C. for three days, and then pelleted by brief centrifugation and washed three more times with NT medium containing 100 ug/ml kanamycin and 500 ug/ml carbenicillin. The washed cells were spread on selection plates (NT medium with addition 0.7% phytagar, 100 mg/L kanamycin, and 500 mg/L carbenicillin). After three to four weeks, independent transformants were transferred to new plates. Once enough tissue was collected, the lipids were extracted and the fatty acid composition analyzed by GC/MS.

EXAMPLE 2

Identification of Cyclopropane Synthase from *Sterculia foetida* Developing Seeds Assay of Cyclopropane Fatty Acid Synthase Frozen endosperm tissue, harvested from developing seeds of *Sterculia foetida* and stored at −70° C., was ground to a fine powder in liquid nitrogen. One weight of powder was thawed in two volumes of buffer containing 0.1 M Na tricine, pH 7.0, 1% w/v defatted BSA, 1% w/v PVP40, 15% v/v glycerol and 1 mM 2-mercaptoethanol. The slurry was briefly homogenized and filtered through miracloth. The filtrate was stored on ice. The residual paste was re-homogenized in two volumes of the above buffer, refiltered and the filtrate combined with the first filtrate. The combined filtrate, designated as "cell free homogenate" can be used for enzyme assay or subsequently fractionated. The use of tricine buffer (compared to tris or phosphate buffer), the use of pH 7.0 (compared to pH 6.4 or 7.8), and the addition of BSA and PVP40 (compared to no additions) each enhanced activity recovered in the cell free homogenate by approximately two-fold.

The activity of cyclopropane fatty acid synthase was assayed as described above. When analyzed without derivitization, labeled free fatty acid was the major constituent in the saponified product (>90%). When analyzed after derivitization with ethereal diazomethane, labeled fatty acid methyl ester was the major product (>90%). When the labeled fatty acid methyl esters were analyzed by C18 reversed-phase TLC there was a single radioactive spot co-eluting with the methyl dihydrosterculate standard. Thus the radioactivity recovered in the hexane phase after saponification is a good measure of the total label in [14C-methyl]dihydrosterculate.

Maximum cyclopropane fatty acid synthase activities of the order of 0.5-1 nmole/min/gram fresh weight of seed tissue were measured. The activity was susceptible to inhibition by a wide range of detergents (CHAPS, Triton-X100, octyl glucoside, sodium deoxycholate, cetylpyridinium chloride and lysophosphatidylcholine). In fractionation studies most of the activity remained in the supernatant plus fat layer fraction after centrifugation at 10,000×g for 5 minutes. Subsequent centrifugation at 100,000×g for one hour produced a microsomal pellet that contained 72% of the total cyclopropane fatty acid synthase activity found in the cell free homogenate, but only 1.5% of the total protein, to give a specific activity enhancement of 48-fold. The action of detergents and the behavior of activity during centrifugation are consistent with the cyclopropane fatty acid synthase being either a membrane-associated or an integral membrane protein. When the reaction with the cell free homogenate was terminated by lipid extraction, most of the labeled dihydrosterculate was found in the phosphatidylcholine fraction. This suggests that oleoyl-phosphatidylcholine is a substrate for the enzyme.

Thus, the initial assay for cyclopropane fatty acid synthase and characterization of the activity indicates that developing seeds of *Sterculia foetida* are able to synthesize CPA-FA. Moreover, the enzyme appears to be a membrane-associated or integral membrane protein, and the substrate appears to be oleoyl-phosphatidylcholine.

Lipid Deposition During Seed Development

Developing seeds from *Sterculia foetida* were collected at 7 time points spanning a period of 100 days, from Jul. 20 to Oct. 15, 1998, at the Miami Montgomery Botanical Center. Each pod contained 10 to 20 seeds. The pods were dark green and the seeds were white in July; as the seeds developed, the color of the pod gradually turned red, while seeds turned brown. The cotyledons of the first collection, on July 20, were still very watery, and the seeds from the last collection, on October 28, were almost completely dried. The fatty acids from all of the seed collections, with the exception of the last collection in which the seed were quite dry, were analyzed as described above.

Figure 2:
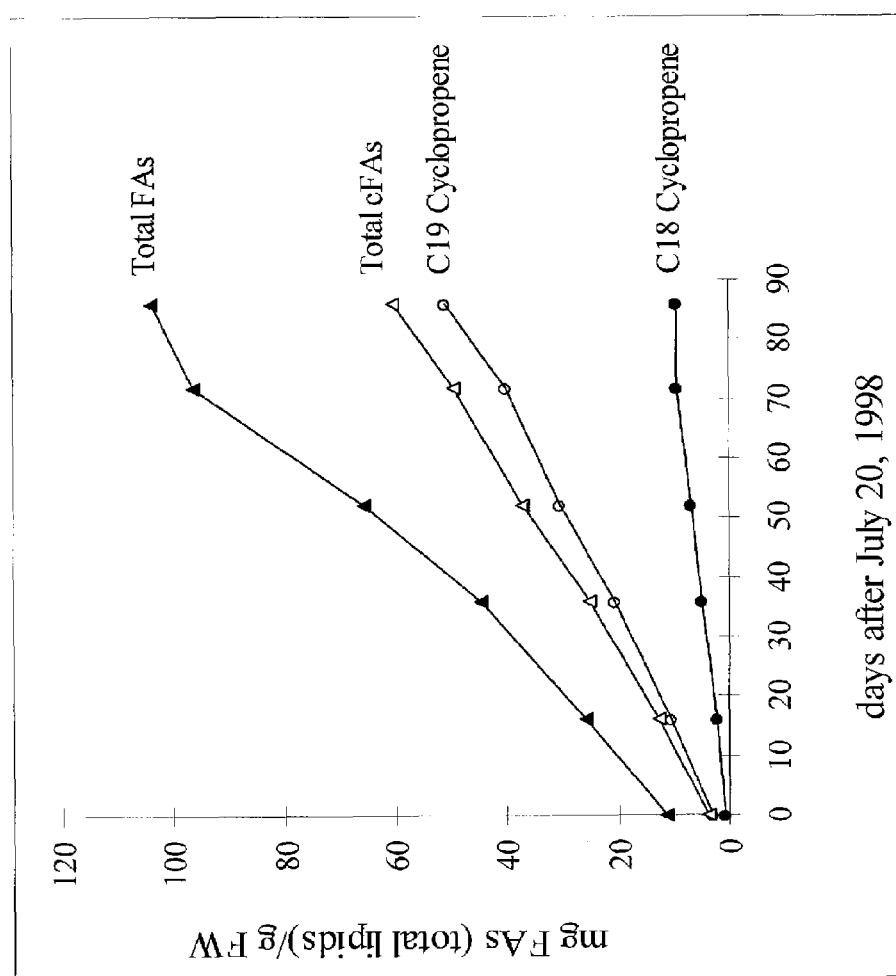
FIG. 2 shows the profile of fatty acid accumulation during *Sterculia* seed development.

The profile of fatty acid accumulation of the developing seeds is shown in FIG. 2. The results show that the total fatty acids and CPE-FAs accumulated at a linear rate from August 5 to October 14. During the same period of time, the percent of the CPE-FAs increased from 40% to 60% of the total fatty acids. The fatty acid composition at 90 days was very similar to data reported for mature seeds (Bohannon and Kleiman (1978) Lipids 13(4): 270-273).

These results also suggested that if the original hypothesis is correct, that CPE-FAs are derived from CPA-FAs, developing seed of *Sterculia foetida* have high activities of cyclopropane fatty acid synthase, and should be a good source of mRNA encoding this enzyme.

Identification and Isolation of cDNA Encoding of Cyclopropane Synthase

In order to maximize the presence of cyclopropane synthase and desaturase in the cDNA library, developing *Sterculia foetida* seeds at stages when CPE-FAs accumulate at the highest rate should be used to prepare a cDNA library. As shown in FIG. 2, CPE-FAs accumulated at essentially a linear rate from August 5 to October 14. Therefore, equal amount of developing seeds from the collections of August 5, August 25, September 10, September 30, and October 14 pooled together and used for RNA extraction.

The RNA was shipped to Stratagene for cDNA library construction. The primary plaques were $2.6 \times 10^7$ pfu with average insert size of 1.7 kb. After mass excision, performed as described above, a total of 21,120 clones were picked and grown in 220 96-well plates. Twenty-eight plates were directly sequenced at the Michigan State University sequencing facility. About 1,500 sequences were obtained with an average reading length of 500 bp. Blast searches (Translated BLAST Searches: Nucleotide query—Protein db [blastx]) at NCBI of these 1,500 un-subtracted sequences identified Legumin A, Legumin B, and a non-specific lipid transfer protein as the three most abundant sequences; these sequences were selected for subsequent library subtraction. The remaining 192 (18,432 clones) plates were spotted on filters by Genome System for library subtraction. The three selected sequences represented about 30% of the clones on the filters. A total of seventy 96-well plates (with the positive clones removed, or subtracted) were re-racked; all of these 70 plates have been sequenced. Approximately 3,800 sequences with 500 bp were obtained. Blast searches of these sequences were also performed.

Based on the blast results, 23 ESTs showed some level of similarity with bacterial cyclopropane synthase. After compiling these EST sequences, it was very clear that all the 23 ESTs were derived from the same gene. The distribution of the ESTs along the gene is shown in FIG. 3. A full length clone was assembled, for which the nucleic acid sequence of the gene is shown in FIG. 4. The predicted putative cyclopropane synthase is 864 amino acids long, as shown in FIG. 5. The bacterial cyclopropane synthase is 382 amino acids long, which is less than half the size of *Sterculia* cyclopropane synthase. A comparison of the *Sterculia* enzyme to the *E. coli* enzyme revealed that the *Sterculia* sequence is 49% similar (188/376) and 32% identical (122/376) to the *E. coli* sequence over the region of overlap, which is the carboxy terminal (see FIG. 6). The *Sterculia* enzyme has an additional approximately 470 amino acids at the amino terminal.

EXAMPLE 3

Characterization of Cyclopropane Fatty Acid Synthase From *Sterculia*

Functional Analysis of the Putative SCPA-FAS in Yeast

Yeast cells possess several characteristics which make it a particularly useful test organism for evaluating whether the putative SCPA-FAS gene isolated from developing *Sterculia* seeds did in fact encode SCPA-FAS. These characteristics include the facts that yeast is a eucaryotic organism and that its fatty acid composition is very simple and consists only of 16:0, 16:1, 18:0, and 18:1. Thus, if dihydrosterculic acid could be detected in yeast transfected with a gene encoding SCPA-FAS, it would confirm that the SCPA-FAS is functioning as a cyclopropane synthase.

The yeast expression vector pYES2/CT was used, and the SCPA-FAS coding sequence was placed under the under the control of a galactose inducible promoter, as described above. Yeast was transfected with the expression vector and grown also as described above. Under the assumption that oleic acid ($18:1^{\Delta 9}$) is the most likely precursor of this enzyme, oleic acid was added to the medium to final concentration of 200 mg/L. The fatty acids of 15 yeast colonies containing pYES2/CT-SCPAS and 5 control colonies with the pYES2/CT-LacZ were analyzed, and the results shown in FIG. 6.

Figure 6:
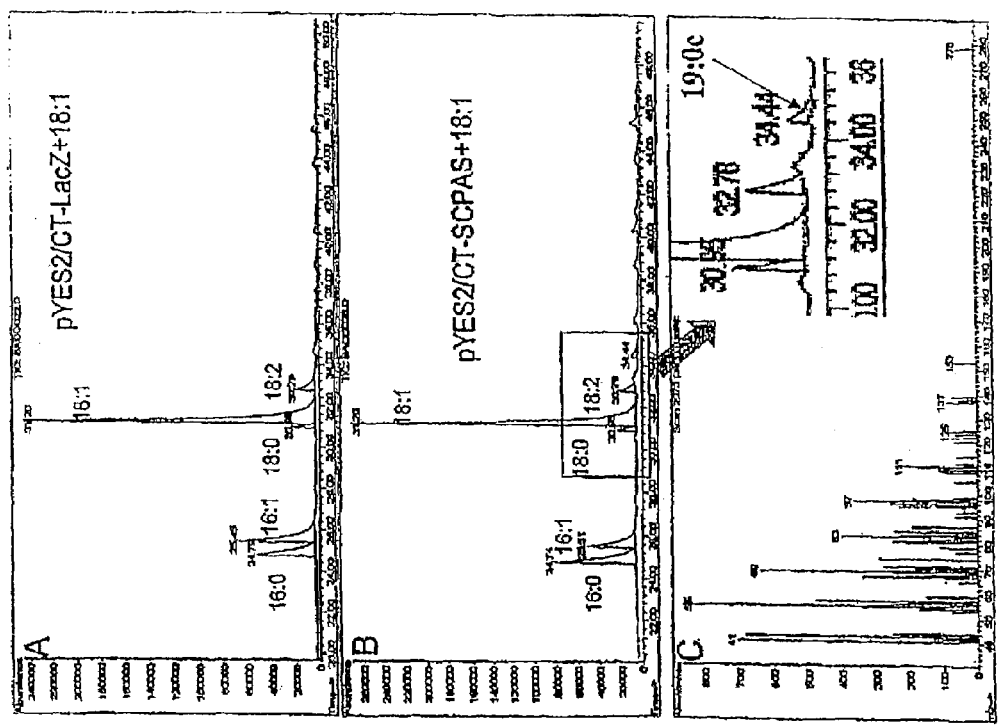
FIG. 6 shows the GC/MS analysis of FAMEs from yeast grown for 48 hr in medium supplemented with 200 mg/L oleic acid. Panel (A) shows the total ion chromatogram of FAMEs from control transgenic yeast containing the construct pYES2/CT-LacZ. Panel (B) shows the total ion chromatogram of FAMEs from yeast containing the construct comprising a coding sequence for *Sterculia* cyclopropane synthase, pYES2/CT-SCPAS. An additional peak with the retention time of 34.44 min can be seen in this chromatogram. Panel (C) shows the mass spectrum of the unique additional peak observed in the chromatogram of FAMES from panel (B). The mass spectrum is the same as that of the dihydrosterculic acid standard (see FIG. 8(A)). The insert is the enlarged image containing the additional peak.

As shown in FIG. 6 (A), oleic acid was effectively incorporated in yeast lipids. Some contamination of the oleic acid used in the feeding experiments by linolenic acid (18:2) was also apparent, as the presence of linolenic showed up in the GC spectrum at 32.78 minutes. As shown in FIG. 6(B), a tiny unique peak with a retention time 34.44 minutes was present in all the 15 colonies of cells transfected with the SCPA-FAS gene but was absent in all the control samples. This peak was identified as dihydrosterculic fatty acid methyl ester based upon two lines of evidences. First, the retention time of this peak is the same as that of the dihydrosterculic acid methyl ester standard. Second, the mass spectrum of this peak was identical to the dihydrosterculic acid methyl ester standard as shown in FIG. 6(C). Therefore, the putative SCPA-FAS enzyme from *Sterculia* does function as cyclopropane synthase.

Functional Analysis of the Putative SCPA-FAS Tobacco Suspension Cells

Although the function of SCPA-FAS was confirmed in yeast system, it was important to evaluate its function in plant tissues. Tobacco suspension cells (Bright Yellow 2) possess several characteristics particularly useful as a test plant system for evaluating the function of the SCPA-FAS gene isolated from developing *Sterculia* seeds in transgenic plant cells. The cell line is well characterized cell line and very easily to transformed. The suspension cells don't contain any CPA-FAs, and provide sufficient tissue for lipid analysis within 40 days of after transformation. Of even greater importance, it has been well documented that tobacco callus are more tolerant to unusual fatty acids.

Figure 7:
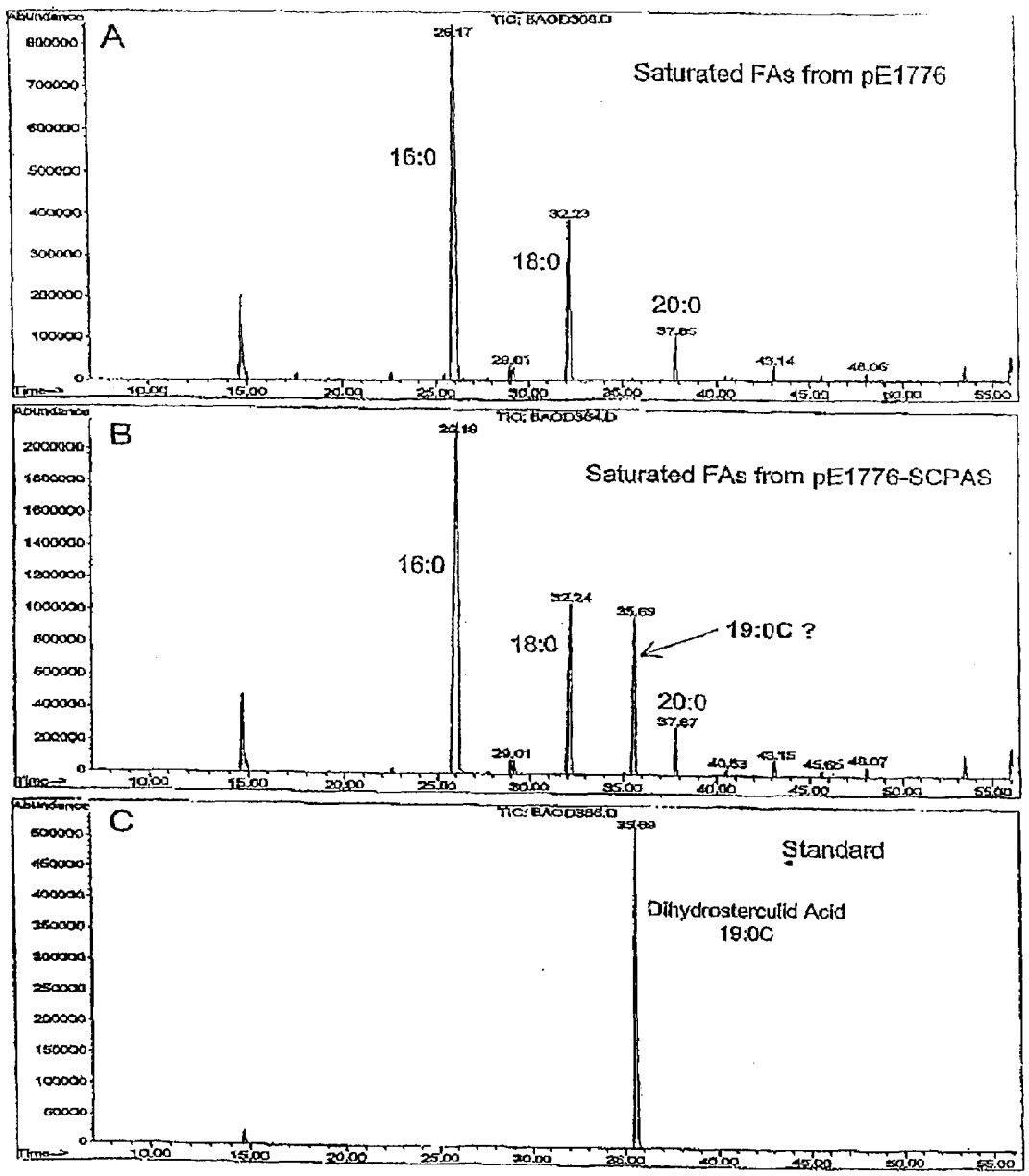
FIG. 7 shows the total ion chromatograms of FAMEs from transgenic tobacco cells. Panel (A) shows the saturated FAMEs from control transgenic tobacco cells transformed with the empty construct pE1776. Panel (B) shows the saturated FAMEs from transgenic tobacco cells transformed with the construct containing a coding sequence for *Sterculia* cyclopropane synthase, pE1776-SCPAS. A major additional peak with a retention time of 35.69 min can be seen in this sample. Panel (C) shows the dihydrosterculic acid methyl-ester standard with a retention time of 35.69 min.
Figure 8:
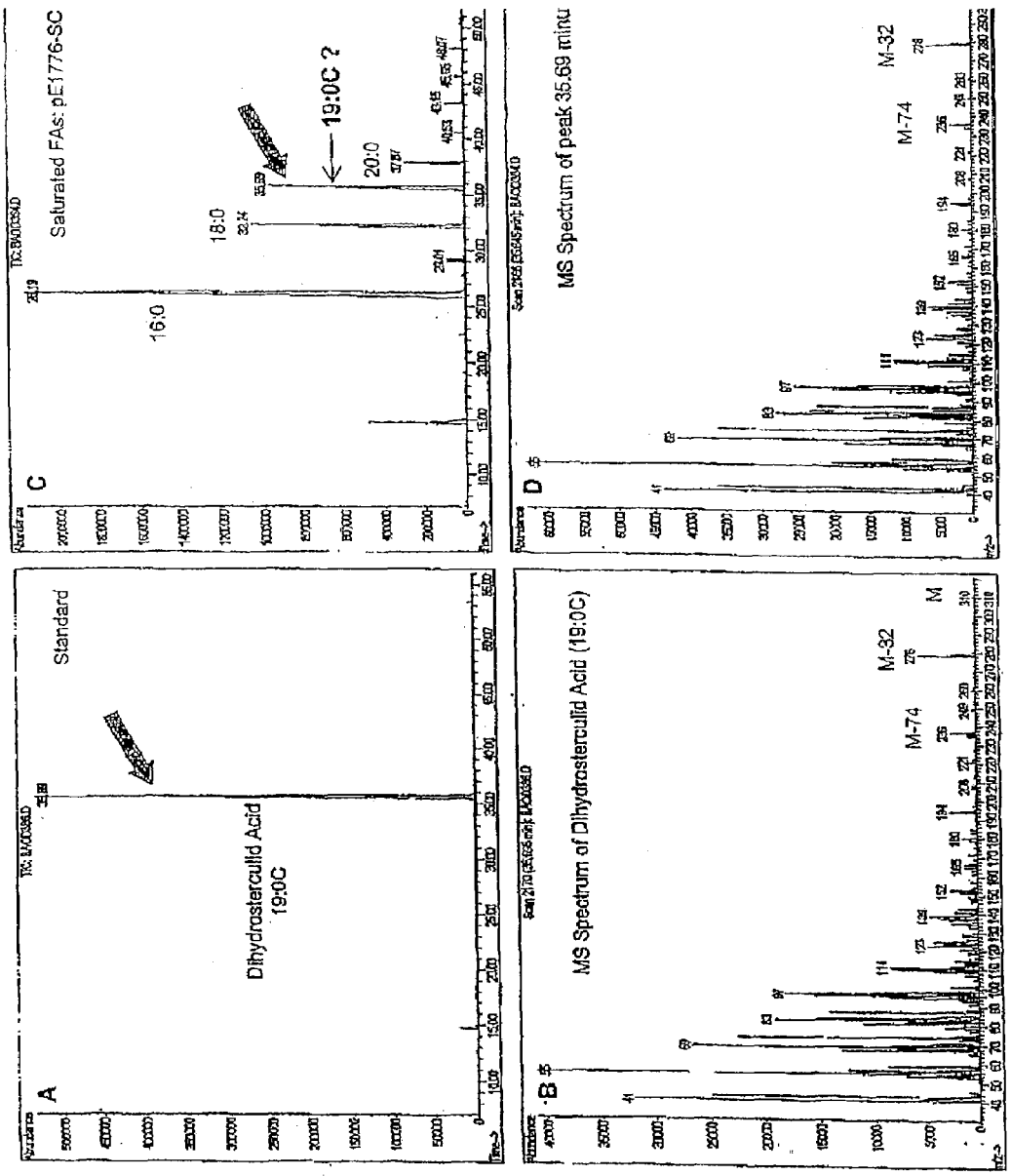
FIG. 8 shows a comparison of the mass spectra of the dihydrosterculic acid standard and the additional peak found in transgenic cells transformed with a coding sequence for *Sterculia* cyclopropane synthase. Panel (A) shows the total ion chromatogram of the dihydrosterculic acid methyl-ester standard. Panel (B) shows the mass spectrum of the dihydrosterculic acid methyl-ester standard. Several ions are unique to dihydrosterculic acid methyl-ester, including the molecular ions m/z=310, M-32 is 278, and M-74 is 236. Panel (C) shows the total ion chromatogram of saturated FAMEs from transgenic tobacco cells transformed with a construct containing the coding sequence for the *Sterculia* cyclopropane synthase, pE1776-SCPAS. Panel (D) shows the mass spectrum of the peak with the retention time of 35.69 min seen in panel (C). The mass spectrum of this peak is nearly identical to that of the dihydrosterculic acid methyl-ester standard, with a signature of molecular ions 310, M-32 of 278, and M-74 of 236.
Figure 9:
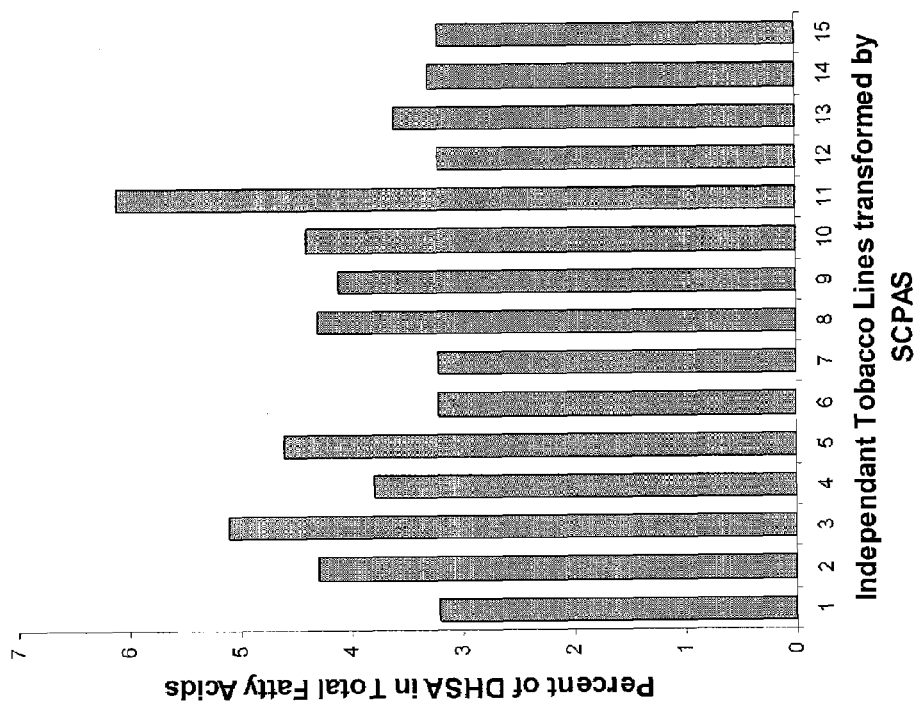
FIG. 9 shows the dihydrosterculic acid content of 15 independent transgenic tobacco lines transformed with a coding sequence for *Sterculia* cyclopropane synthase.

The SCPA-FAS-encoding nucleic acid was transformed into tobacco suspension cells under the control of a constitutive promoter; at the same time, an empty vector was also transformed into tobacco cells as control. After the transformation, independent transformants were transferred to new plates and subcultured with 20-day intervals. Lipids were extracted from 15 test transformants with pE1776-SCAPS, and from 12 control transformants with the empty vector pE1776. The lipids were extracted and the fatty acid methyl-esters prepared from these samples as described above. Saturated FAMEs were separated from other FAMEs with argentation TLC; then the saturated FAMEs were analyzed by GC/MS along with methyl-ester of DHSA standard. The results are shown in FIG. 7. The major saturated fatty acids in control tobacco callus transformed with the empty vector of pE1776 were 16:0, 18:0, and some 20:0, as is shown in FIG. 7(A). In test tobacco callus transformed with putative *Sterculia* cyclopropane synthase (SCPA-FAS), the same fatty acids were present as were in the control samples, with an additional prominent peak with retention time of 35.69 minutes, as is shown in FIG. 7(B). This additional peak was identified as dihydrosterculic acid by comparison to a dihydrosterculic acid standard, which had the same retention time as the additional peak, 35.69 minutes, as is shown in FIG. 7(C). To confirm its identity, the additional peak was further analyzed by mass spectrometry; the results are shown in FIG. 8. The mass spectrum of control dihydrosterculic acid is characterized by be a molecular ion of 310 along with other unique ions like 278 (M-32) and 236 (M-74), as shown in FIG. 8(B). The mass spectrum of the additional peak with a retention time of 35.69 minutes, as shown in FIG. 8(D), was nearly identical to that of the dihydrosterculic acid standard. Therefore, based upon both the retention time and mass spectra comparisons, the additional fatty acid found in tobacco callus transformed with nucleic acid encoding *Sterculia* CPA-FAS was identified as dihydrosterculic acid. The fatty acid compositions of 15 independent transformants with nucleic acid encoding SCPA-FAS were analyzed, and the dihydrosterculic acid contents in these transformants ranged from 3% to 6%, as shown in FIG. 9. The average amount of dihydrosterculic acid present was approximately 4%.

Elucidation of the Cyclopropene Ring Formation

The pathway for the synthesis of sterculic acid proposed by Yano et al. ((1972) Lipids 7: 35-45), based upon radioisotope labeling experiments, was an initial formation of dihydrosterculic acid from oleic acid, with subsequent of desaturation dihydrosterculic acid to sterculic acid. Yano et al further suggested that the ring methylene group was derived from the methyl group of methionine. This proposal was confirmed by preliminary labeling studies with *Sterculia* developing seeds. When developing seeds were labeled with $^{14}C$-methionine, the majority of radioactivity was first found in DHSA, with small amounts present in sterculic acid; with longer periods of incubation, more radioactivity accumulated in the sterculic acid.

Additional labeling experiments were carried out with tobacco suspension cells transformed with either nucleic acid encoding SCPA-FAS (SCPAS-2 and SPAS-11, two independent transgenic lines transformed with pE1776-SCPAS) or an the empty vector. The suspension cells were incubated with either [$1$-$^{14}C$] oleic acid or L-[methyl-$^{14}C$]methionine for 24 hours. The FAMEs from the labeled cells were then separated by argentation TLC and the distribution of radioactivity was visualized with Instant Imager. When incubated with [$1$-$_{14}C$] oleic acid, the test transformants carrying nucleic acid encoding SCPA-FAS yielded about 3.5% of the total radioactivity in the top band containing only saturated fatty acids, whereas control transformants carrying the empty vector pE1776 resulted in no radioactivity associated with saturated fatty acids. These results demonstrate that the presence of SCPA-FAS resulted in the conversion of oleic acid (18:1) into saturated fatty acid, which was most likely dihydrosterculic acid. Moreover, the majority of [$1$-$^{14}C$] oleic acid taken up was further desaturated to linoleic (18:2). When cells were incubated with L-[methyl-$^{14}C$] methionine, radioactivity was found in the saturated fatty acid band only from the cells transformed with nucleic acid encoding SCPA-FAS, but not in the control cells. From the previous analyses of the saturated fatty acids of both the test and control transformants, the only difference between the two was that DHSA was found exclusively in transformants with nucleic acid encoding SCPA-FAS. Therefore, the radioactivity associated with the saturated fatty acids is most likely DHSA.

To confirm that the radioactive fatty acid was in fact DHSA, the saturated FAMEs obtained from pE1776-SC-PAS-2 after incubation with either [$1$-$_{14}C$] oleic acid or L-[methyl-$^{14}C$] methionine were eluted from the argentation plate, and the individual saturated FAMEs were separated by C18 reverse phase TLC. The radioactive FAMEs labeled from either [$1$-$^{14}C$] oleic acid or L-[methyl-$^{14}C$] methionine were located at the same position as the DHSA standard. The radioactive spots were then eluted from the C18 plate and analyzed by GC/MS. The radioactive FAMEs were therefore identified as DHSA based upon both the retention time and the mass spectra.

Taken together, these results demonstrate that SCPA-FAS synthesizes dihydrosterculic acid by transferring a methylene group from S-adenosyl-methionine to oleic acid.

EXAMPLE 4

Preparation Of Antibody Against *Sterculia* Cyclopropane Synthase

Antibody was prepared to *Sterculia* cyclopropane fatty acid synthase (CPA-FAS) expressed in a bacterial expression system. The conserved carboxyl terminal region (about 390 amino acids) of the protein was chosen for antibody production, and was amplified by PCR and expressed in *E. coli* with a HIS tag. An alignment between the *Sterculia* and the bacterial CPA-FAS is shown in FIG. 11; the portion of the *Sterculia* CPA-FAS from about amino acid 470 to amino acid 864 was used to prepare antibody.

The vector utilized was pET28a(+) (Novagen, inc., 601 Science Drive, Madison, Wis. 53711), where the site of insertion is EcoR I and Sac I.

The PCR primers used to amplify the partial *Sterculia* cyclopropane synthase were as follows:

```
JO873  CCGGAATTCTGTTCTCTTAAAACAGCTCTGAAAGTGC
(SEQ ID NO:32)

JO885  CCCTCTAGAGCTCGGATAAATGAAAACTATTTCAATTATCCG
(SEQ ID NO:33)
```

The location of primers in the *Sterculia* cyclopropane synthase are shown in FIG. 12. PCR reactions were performed under the following conditions:

| | |
|---|---|
| Template [R15-C3] | 5.0 ul |
| Buffer [10 X] | 10.0 ul |
| dNTP [10 mM] | 2.0 ul |
| JO873 [4.1 pM/ul] | 9.0 ul |
| JO885 [7.3 pM/ul] | 5.0 ul |
| Water | 68.5 ul |
| PWO | 0.5 ul |
| 94° C. | 5 min |
| 94° C. | 30 seconds |
| 55° C. | 30 seconds |
| 72° C. | 30 seconds |
| 30 Cycles | |

72° C. 7 min

Three separate samples were subjected to PCR, designated EA-I, EA-II, and EA-III. After the reactions, the PCR fragments were purified with a Qiagen PCR purification kit. The PCR fragments and the vector were then digested with the restriction enzymes EcoRI and SacI. The PCR fragments were inserted into the vectors by ligation overnight at 4° C. with T4 DNA ligase, at an insert: vector ratio of 4:1. The resulting constructs, designated pET28a-EA-I, pET28a-EA-II, and pET28a-EA-III, were transformed into DH5∀. The colonies were screened to identify the correct constructs; spin-preps were prepared from pET28a-EA-II-4 and pET28a-EA-III-5. These two constructs were transformed into BL21 for protein expression. The expressed protein is shown in FIG. 13, where the portion of the amino acid sequence highlighted is derived from the vector, which contains a 6-histidine tag for purification.

The expression of the partial *Sterculia* CPA-FAS was then induced as follows: BL21 containing pET28a-EA-114 or pET28a-EA-III-5 were inoculated into 2 ml of LB with 50 ug/ml kanamycin, and grown at 37° C. overnight with shaking. The next morning, 1.5 ml of the overnight culture was inoculated into 500 ml LB with 50 ug/ml kanamycin; the cells were grown for 2.5 hours. IPTG was then added to a final concentration of 0.5 mM. The cells were grown for an additional 5 hours, and collected by centrifuging at 5,000 g for 10 min. The collected cells were either stored at −20° C. or used directly for protein extraction.

Protein was extracted from collected cells as follows: Cells from 500 ml culture were resuspended into 60 ml of cell lysis buffer (20 mM Tris-HCl, pH7.4; 0.2 mM NaCl; 10 mMβ-mercaptoethanol; 1 mM Benzamidine; 1% (v/v) Triton X-100; and 1 mM PMSF). The cells were disrupted by ultrasonic treatment using three 20-second pulses at 50 watts on ice, and the suspension centrifuged at 10,000 g for 20 min. The soluble fraction was the supernatant, and the insoluble fraction contained the inclusion bodies.

Inclusion bodies were purified from the insoluble fraction as follows: The insoluble fraction was resuspended in 8 ml of buffer (50 mM Tris-HCl, pH 8.0; 1 mM EDTA; 25% (w/v) Sucrose; and 25 mg Lysozyme). $MgCl_2$, $MnCl_2$, and DNase I were then added to final concentrations 10 mM, 1 mM, and 10 ug/ml, respectively. The mixture was incubated at room temperature for 30 min, and 20 ml of the following buffer was added (0.2 M NaCl; 1% Deoxycholic acid; 1.6% (v/v) Triton X-100; 20 mM Tris-HCl, pH7.5; and 2 mM EDTA). The mixture was centrifuged at 5000×g for 10 minutes, and the pellet resuspended in 0.5% triton X-100/1 mM EDTA and recentrifuged. This procedure was repeated until a tight pellet was obtained.

The inclusion bodies were then subjected to 10% SDS PAGE, and the predominant band of the partial *Sterculia* CPA-FAS was cut out and stored at −20° C. The frozen gel slices were sent to Cocalico Biologicals, Inc. (Reamstown, Pa.) for antibody preparation in rabbits.

EXAMPLE 5

Identification and Characterization of Cyclopropane Fatty Acid Synthase from Cotton Identification of Sequences Coding Cotton CPA-FAS The amino acid sequence of *Sterculia* CPA-FAS was used to blast NCBI EST database. Three ESTs were found from cotton. All three are from the same library (fibers isolated from bolls harvested 7-10 dpa) and were sequenced at Clemson University Genomics Institute. These ESTs are designated and described as follows, and are shown in FIG. 14.

EST1
gi|13351381|gb|BG441729.1|BG441729
GA_Ea0014H01f 7-10 dpa fiber library
*Gossypium arboreum* cDNA clone GA_Ea0014H01f.
EST2
gi|21094588|gb|BQ406901.1|BQ406901
GA_Ed0100C02f *Gossypium arboreum* 7-10 dpa fiber library
*Gossypium arboreum* cDNA clone GA_Ed0100C02f.
EST3 Complementary
gi|18099677|gb|BM358931.1|BM358931
GA_Ea0014H01r *Gossypium arboreum* 7-10 dpa fiber library
*Gossypium arboreum* cDNA clone GA_Ea0014H01r.

Figure 15:
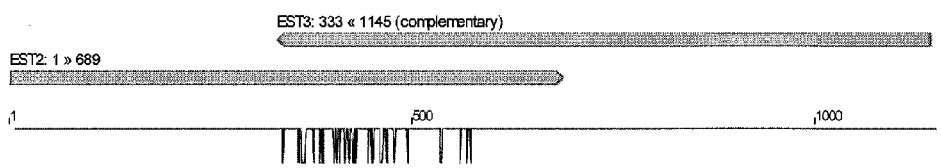
FIG. 15 shows results of a contig analysis of the three cotton ESTs shown in FIG. 14, which demonstrates that EST 2 and 3 are overlap ESTs. Panel A shows the results graphically; panel B shows a nucleic acid sequence alignment of EST2 (SEQ ID NO:4), EST3 (SEQ ID NO:5), and Contig 1 (SEQ ID NO:24), and panel C shows the nucleic acid sequence of Contig 1 (SEQ ID NO:6).

From a contig analysis, it was determined that EST2 and EST3 are overlap ESTs, designated EST2-3, as shown in FIG. 15. The predicted amino acid sequences of the two contigs, EST1 and EST2-3, as well as of EST2 and of EST3, are shown in FIG. 16. An alignment of the predicted amino acid sequences of the two contigs, EST2 and EST2__3, with that of the *Sterculia* CPA-FAS is shown in FIG. 17.

The prevalence of sequencing errors in EST sequences frequently invites an additional analysis of predicted amino acid sequences encoded by ESTs. In some instances, this is due to the fact that errors in sequencing result in frameshift, which result in non-coherent amino acid sequences; in other words, a direct translation of the encoded sequence in an EST may not result in a full length polypeptide fragment. Thus, a predicted amino acid sequence can be aligned with a known sequence, such that errors can be observed; these errors are corrected, and a coherent amino acid sequence reconstructed. An analysis of the three cotton ESTs revealed that EST3 contained several apparent sequencing errors. By comparing the encoded sequence with the analogous region of the *Sterculia* CPA-FAS amino acid sequence, two apparent reading frames were observed, reading frame+2 and reading frame+3, as follows:

Reading frame +2:

FLLTVHTNPPGAFPSNP*QPAGFLKRIHIPWWTPAFFG*AFISHGCCHKIQCAAGGTH
RNVLLPPTEMVEKTFPENTSKVLALGFPQKEIRTWFYXFLDYGAAQLKLGGLLDSQV
VFSRAGNFGTLGDPYKGFPSAYSFMDD*TKCLNI*SPYHDSPSWIQLVPVFPQSPAF
V*LWFSFRSEKEISQ*CMLIMKCLYLVYLYWLDFMYGDAVCFLKKKPHHP

Reading Frame +3:

SFLPFTPIPLELSLAIPSNPLVFLSVYIFPGGPLLSLDRHLSAMAAATRFSVQQVEHIG
MCYYHPLRWWRKLFLKTQAKFWLWGSPRSSSGHGNTISITVLLVLRQEPL*IPRLY
FLEPVISVHLEIHTKVSLLHIPSWMIEQSV*IYDPHTMIHPAGSNWYQCFPSPLLLFSY
GFRFVPKKK*ANNVC***NVCIWYIYTGWILCMEMLFAF*RRNPTTP

Combining the two reading frames result in the amino acid sequence below; this sequence (SEQ ID NO:9) comprises the highlighted portions of reading frames +2 and +3 above, and is shown in FIG. 16.

Combined reading frames:

FLSVYIFPGGPLLSLDRHLSAMAAATRFSVQQVEHIGMCYYHPLRWWRKLFL... (SEQ ID NO:9)

Characterization of Cotton CPA-FAS

Western Blot analysis with Antibody to *Sterculia* CPA-FAS

Antibody to *Sterculia* CPA-FAS, prepared as described in Example 4, was used to stain protein extracts obtained from cotton and *Sterculia* protein extracts by the following procedure. *Sterculia* was grown as described previously, and embryo tissue extracted. Cotton plants (*Gossypium hirsutum* L.) were grown in a growth room with 14-hour light and 10 hour dark cycle. Root, stem and leaf tissues were harvested from these plants two weeks after germination. Embryo tissues were harvested from cotton plants grown in a greenhouse under the natural light and temperature conditions about 10 days after flowering. The same types of tissues were used for both Western Blot and fatty acid analyses.

Tissue samples were obtained from cotton embryos, leaves, stems, and roots, and from *Sterculia* embryos. Protein extracts were obtained by homogenizing 0.5 gm of tissue in 2 ml ice-cold buffer (20 mM Tris-HCl, pH7.5, 0.2 M NaCl, 10 mM β-mercaptoethanol). The concentration of the protein in the homogenate was determined, and then 150 :g of cotton tissue proteins and 20 :g of proteins from *Sterculia* embryos were loaded onto 8% SDS polyacrylaminde gel. After electrophoresis, the separated proteins were transferred to a nitrocellulose membrane for Western Blot analysis, with the antibody against *Sterculia* CPA-FAS.

Figure 18:
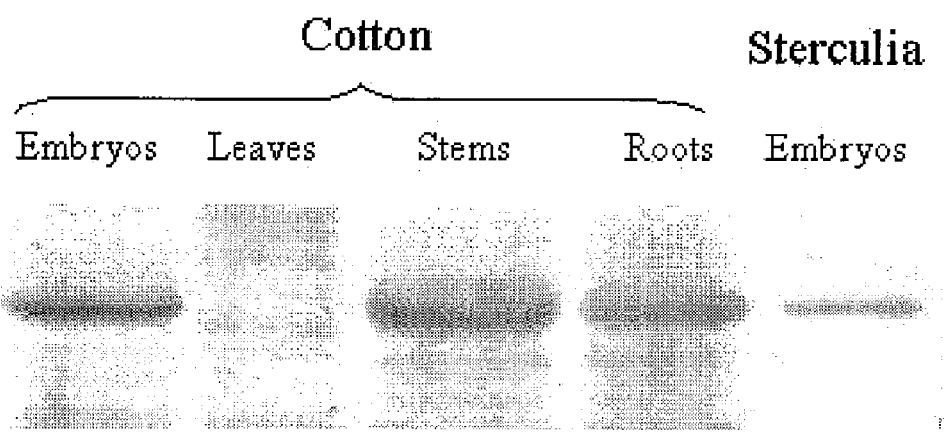
FIG. 18 shows a Western blot analysis of different tissues (embryos, leaves, stems, and roots) from cotton and of embryo tissue from *Sterculia* with an antibody against *Sterculia* cyclopropane fatty acid synthase (CPSA-FAS).

The results of the Western Blot analysis are shown in FIG. 18, where a protein in the cotton tissue extracts binds the *Sterculia* antibody; based upon its antibody binding, and the presence of the EST sequences in cotton tissues, this protein was identified as a cotton CPA-FAS. The results demonstrate that antibody against *Sterculia* CPA-FAS cross-reacts with the cotton CPA-FAS extremely well, indicating that the two proteins are very similar. Moreover, the size of cotton CPA-FAS is almost the same as its counterpart in *Sterculia*. In cotton, CPA-FAS is highly expressed in young embryo, stem, and root tissues, but not in leaf tissues. These observations are in general agreement with the production of carbocyclic fatty acids in these tissues, as described below.

Fatty Acid Analysis

Fatty acids were analyzed from embryo, leaf, stem, and root tissues from cotton, and the results shown below.

Total cyclopropene fatty acids, which include 18:1c+19:1c:

| Root | 34% |
|---|---|
| Stem | 27.5% |
| Leaf | 0.00% |
| Embryo | 0.3% |

Total cyclopropane fatty acids, which include 19:0c:

| Root | 0.88% |
|---|---|
| Stem | 0.48% |
| Leaf | 0.00% |
| Embryo | 0.23% |

TABLE 1

Fatty acid analysis of Cotton Tissues

| Fatty Acid | Root | Stem | Leaf | Embryo |
|---|---|---|---|---|
| 16:0 | 25.9 | 22.1 | 21.0 | 28.4 |
| 16:1 | 0 | 0 | 0 | 0.5 |
| 18:1c | 25.1 | 18.3 | 0 | 0.3 |
| 18:0 | 0.5 | 0.5 | 2.9 | 1.6 |
| 18:1 | 2.9 | 7.0 | 14.7 | 12.2 |
| 18:2 | 21.5 | 27.5 | 39.5 | 56.7 |
| 19:1c | 8.9 | 9.2 | 0 | 0 |
| 19:0c | 0.9 | 0.5 | 0 | 0.2 |
| 18:3 | 14.3 | 15.0 | 21.92 | 0.1 |

These results demonstrate that in cotton root and stem tissues, cyclopropane and cyclopropene fatty acids compose about 30% and about 35% of total fatty acids, respectively. But these fatty acids compose only about 2% of the total fatty acids in more mature embryo tissues, and none in leaf tissues. Of these fatty acids in root and stem tissues, malvalic acid is the most abundant, accounting for about 25% and about 20% of total fatty acids in root and stem tissues, respectively.

Thus, in cotton tissues, the abundance of CPA-FAS in different tissues, as demonstrated by Western Blot analysis as described above, is generally in agreement with the percentage of cyclic fatty acid. It should be noted that in plants in which cyclic fatty acids have been observed, cyclopropane and cyclopropene fatty acids are synthesized very early in seed development, where they can initially represent a relatively high proportion of the total fatty acids; however, the synthesis of these fatty acids decreases as the seeds mature, so that the proportion of these fatty acids decreases to a much lower level in mature seed tissue.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

The invention claimed is:

1. A gene comprising an isolated nucleic acid sequence encoding a plant cyclopropane fatty acid synthase, wherein said sequence is at least 90% identical to SEQ ID NO 1, and wherein said sequence encodes a protein having cyclopropane fatty acid synthase activity.

2. The gene of claim 1, wherein the plant is from the order Malvales.

3. The gene of claim 2, wherein the plant is a *Sterculia* plant or a cotton plant.

4. The gene of claim 3, wherein the *Sterculia* plant is a *Sterculia foetida* plant or the cotton plant is a *Gossypium arboreum* plant.

5. The gene of claim 4, wherein the nucleic acid sequence comprises SEQ ID NO: 1.

6. A gene comprising a nucleic acid sequence encoding a plant cyclopropane fatty acid synthase, wherein said sequence is at least 90% identical to SEQ ID NO 1, and wherein said sequence encodes a protein having cyclopropane fatty acid synthase activity operably linked to a heterologous promoter.

7. A composition comprising a vector comprising a nucleic acid sequence encoding a plant cyclopropane fatty acid synthase, wherein said sequence is at least 90% identical to SEQ ID NO 1, and wherein said sequence encodes a protein having cyclopropane fatty acid synthase activity.

8. A composition comprising a purified polypeptide encoded by a nucleic acid sequence encoding a plant cyclopropane fatty acid synthase, wherein said sequence is at least 90% identical to SEQ ID NO 1, and wherein said sequence encodes a protein having cyclopropane fatty acid synthase activity.

9. A composition comprising a purified plant cyclopropane fatty acid synthase, wherein said cyclopropane fatty acid synthase comprises an amino acid sequence SEQ ID NO:2, or a sequence at least 90% identical thereto.

10. The composition of claim 9, wherein the plant is of the order Malvales.

11. The composition of claim 10, wherein the plant is a *Sterculia* plant or a cotton plant.

12. The composition of claim 11, wherein the *Sterculia* plant is *Sterculia foetida* or the cotton plant is a *Gossypium arboreum* plant.

13. The composition of claim 12, wherein the purified cyclopropane fatty acid synthase comprises amino acid sequence SEQ ID NO:2.

14. A gene comprising an isolated nucleic acid sequence encoding a cyclopropane fatty acid synthase of claim 9.

* * * * *